US012760010B2

(12) United States Patent
Gavade et al.

(10) Patent No.: US 12,760,010 B2
(45) Date of Patent: Oct. 13, 2026

(54) 5-HYDROXY-1,4-NAPHTHALENEDIONE FOR USE IN THE TREATMENT OF CANCER

(71) Applicant: GODAVARI BIOREFINERIES LIMITED, Mumbai (IN)

(72) Inventors: Sandip Gavade, Mumbai (IN); Sangeeta Srivastava, Mumbai (IN); Prashant Kharkar, Mumbai (IN); Maithili Athavale, Mumbai (IN)

(73) Assignee: GODAVARI BIOREFINERIES LIMITED, Maharashtra (IN)

( * ) Notice: Subject to any disclaimer, the term of this patent is extended or adjusted under 35 U.S.C. 154(b) by 632 days.

(21) Appl. No.: 18/250,738

(22) PCT Filed: Oct. 26, 2021

(86) PCT No.: PCT/IN2021/051015
§ 371 (c)(1),
(2) Date: Apr. 26, 2023

(87) PCT Pub. No.: WO2022/091123
PCT Pub. Date: May 5, 2022

(65) Prior Publication Data

US 2024/0018132 A1 Jan. 18, 2024

(30) Foreign Application Priority Data

Oct. 26, 2020 (IN) ............................ 202021046675

(51) Int. Cl.

| | |
|---|---|
| ***C07D 413/12*** | (2006.01) |
| ***A61P 35/00*** | (2006.01) |
| ***C07C 217/24*** | (2006.01) |
| ***C07C 235/10*** | (2006.01) |
| ***C07D 265/30*** | (2006.01) |
| ***C07D 317/64*** | (2006.01) |

(52) U.S. Cl.
CPC ........... *C07D 413/12* (2013.01); *A61P 35/00* (2018.01); *C07C 217/24* (2013.01); *C07C 235/10* (2013.01); *C07D 265/30* (2013.01); *C07D 317/64* (2013.01)

(58) Field of Classification Search
None
See application file for complete search history.

(56) References Cited

FOREIGN PATENT DOCUMENTS

WO WO-2017106624 A1 * 6/2017 .......... C07C 205/46

OTHER PUBLICATIONS

Wolf et. al. "The effect of naphthalene and naphthoquinone derivatives on the activity of (alanine)-aminopeptidase from pig kidneys" Wissenschaftliche Zeitschrift Martin-Luther-Universitaet Halle-Wittenberg, Mathematisch-Naturwissenschaftliche Reihe 1977, 26, 1, 95-102. ISSN: 0138-1504 (Year: 1977).*
CAS 130-15-4. CAS Registry File Accessed Feb. 6, 2026 from STN, entered into STN Nov. 16, 1984. (Year: 1984).*
International Search Report, dated Feb. 18, 2022 for corresponding International Application No. PCT/IN2021/051015 (4 pages).
Written Opinion of ISA, dated Feb. 18, 2022 for corresponding International Application No. PCT/IN2021/051015 (6 pages).

* cited by examiner

*Primary Examiner* — Jennifer A Berrios
*Assistant Examiner* — Sophia Reilly
(74) *Attorney, Agent, or Firm* — INTELLECTUAL PROPERTY LAW GROUP LLP

(57) ABSTRACT

The present invention discloses compounds for inhibition of uncontrolled cell proliferation particularly cancer stem cells. Particularly, the invention relates to compounds of Formula (I) to (IV) for the treatment of cancer.

10 Claims, 28 Drawing Sheets

5-HYDROXY-1,4-NAPHTHALENEDIONE FOR USE IN THE TREATMENT OF CANCER

CROSS-REFERENCE TO RELATED APPLICATIONS

This application is a U.S. National Phase application, under 35 U.S.C. § 371, of International Application no. PCT/IN2021/051015, with an international filing date of Oct. 26, 2021, and claims benefit of India application No. 202021046675 filed on Oct. 26, 2020; each of which is hereby incorporated by reference for all purposes.

FIELD OF THE INVENTION

The present invention relates to compounds for the inhibition of uncontrolled cell proliferation, particularly cancer cells.

BACKGROUND OF THE INVENTION

Newer anticancer drugs act directly against abnormal proteins in cancer cells; this is termed targeted therapy. The majority of chemotherapeutic drugs can be divided into alkylating agents, antimetabolites, anthracyclines, plant alkaloids, topoisomerase inhibitors, and other antitumor agents. While molecularly-targeted therapies are available for treatment of cancer for a high price, majority of the world population rely on standard chemotherapy.

The standard anticancer regiment targets most of the dividing cancer cells and not quiescent or slow-dividing cancer stem cells (CSCs). Even though, CSCs have been identified a while ago, scientists around the globe are still looking to find CSC-targeted agents and unfortunately, until today, there is none available in the market to specifically target CSCs.

Therefore, it is important to develop CSC-specific therapeutics, which would effectively inhibit CSCs and work either alone or in combination with the standard therapies to provide effective treatment option for the cancer patients.

SUMMARY OF THE INVENTION

The present invention relates to compounds of Formula I for treating various conditions, particularly for inhibition of uncontrolled cell proliferation or unregulated cell growth. Particularly the compounds are effective against cancer cells. The compounds are also effective against cancer stem cells. The structure of Formula I is as follows:

Formula I

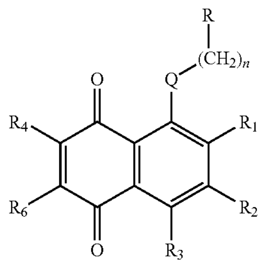

wherein, n is 1-10;

Q is O, S, —NY', wherein Y' is selected from —H, alkyl;

$R_1$, $R_2$, $R_3$ and $R_4$ each independently is selected from —H, alkoxy, alkyl, substituted or unsubstituted aromatic group, substituted or unsubstituted aromatic group with a fused ring formed by heterocycloalkyl group, —$NH_2$, —$NO_2$, —$NHCOCH_3$, —CN, —O—, halogen, —$OCF_3$, heterocycloalkyl group, —O—$(CH_2)_n$-heterocycloalkyl group;

R is selected from substituted or unsubstituted heterocycloalkyl, substituted or unsubstituted cycloalkyl, —$NR_{10}R_{11}$, —$NR_{10}R_{11}$·HCl or acid salt, —$OR_{10}R_{11}$, —$CONR_{10}R_{11}$, —$NR_{10}R_{11}CONR_{10}R_{11}$, —$NR_{10}R_{11}SOONR_{10}R_{11}$, —COOH, wherein $R_{10}$ and $R_{11}$ each independently is selected from —H, alkyl, substituted or unsubstituted aryl, heteroaryl, alkyl amine, substituted aryl amine, substituted or unsubstituted cycloalkyl group, —$CH_2$—$CH_2$—O-alkyl, or $R_{10}$ and $R_{11}$ together form a substituted or unsubstituted cycloalkyl or heterocycloalkyl or $R_{10}$ and $R_{11}$ together form a substituted or unsubstituted cycloalkyl or heterocycloalkyl ring with —N included in the ring;

$R_{10}$ is

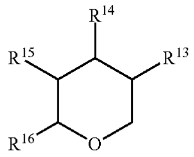

wherein, $R_{13}$ is selected from —OH, —$NH_2$, —$NHCOCH_3$, alkyl, acetyl, $C_3$-$C_8$ acyl group, X selected from F, Cl, Br;

$R_{14}$ is selected from alkoxy, —OMe, —OH, $NH_2$, —$NHCOCH_3$, alkyl, acetyl, $C_3$-$C_8$ acyl group, X selected from F, Cl, Br;

$R_{15}$ is selected from alkoxy, —OMe, —OH, —H, Br, $NH_2$, alkyl, acetyl, $C_3$-$C_8$ acyl group, X selected from F, Cl, Br;

$R_{16}$ is selected from —H, —$CH_2OH$, —OH, alkyl, alkoxy;

$R_6$ is selected from group R defined above, —H,

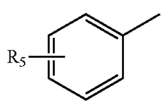
,
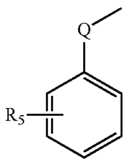

$R_5$ is located at any position and is present as a single or multiple group and is selected from —$CH_2$—O—$CH_2$, —COOH, alkyl, alkoxy, $NHCOCH_3$, —H, —OR, —NR, —X selected from F, Cl, Br, or $R_5$ forms a fused ring having —O—$CH_2$—O— group.

In an aspect of the invention, a compound of Formula II represented by the below structure is covered.

Formula II

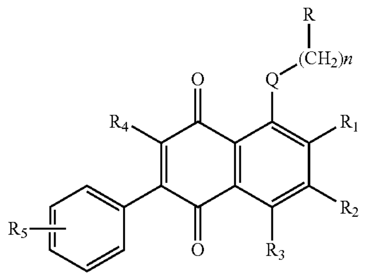

In an aspect, a compound of Formula III represented by the below structure is covered.

Formula III

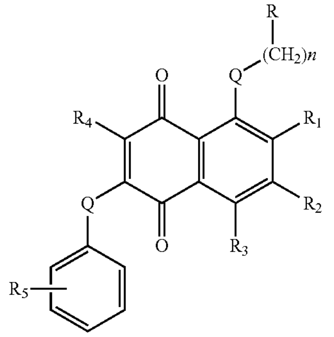

In an aspect of the invention, a compound of Formula IV represented by the below structure is covered.

Formula IV

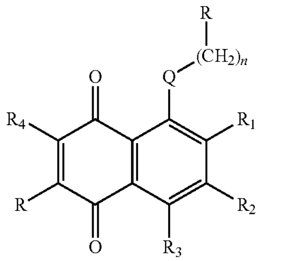

An aspect of the invention relates to a pharmaceutical composition comprising the above compounds, at least one pharmaceutically acceptable excipient and optionally at least one active agent.

An aspect of the present invention relates to compounds of Formula I to IV for use in the treatment or inhibition of uncontrolled cell growth such as cancer including use in targeting cancer cells such as cancer stem cells.

Another aspect of the invention discloses a method of treating or inhibiting uncontrolled cell growth. The method comprises of administering an effective amount of compound of Formula I to IV or a pharmaceutical composition of Formula I to IV or any of the above compounds to a patient.

DETAILED DESCRIPTION OF THE INVENTION

Figure 1:
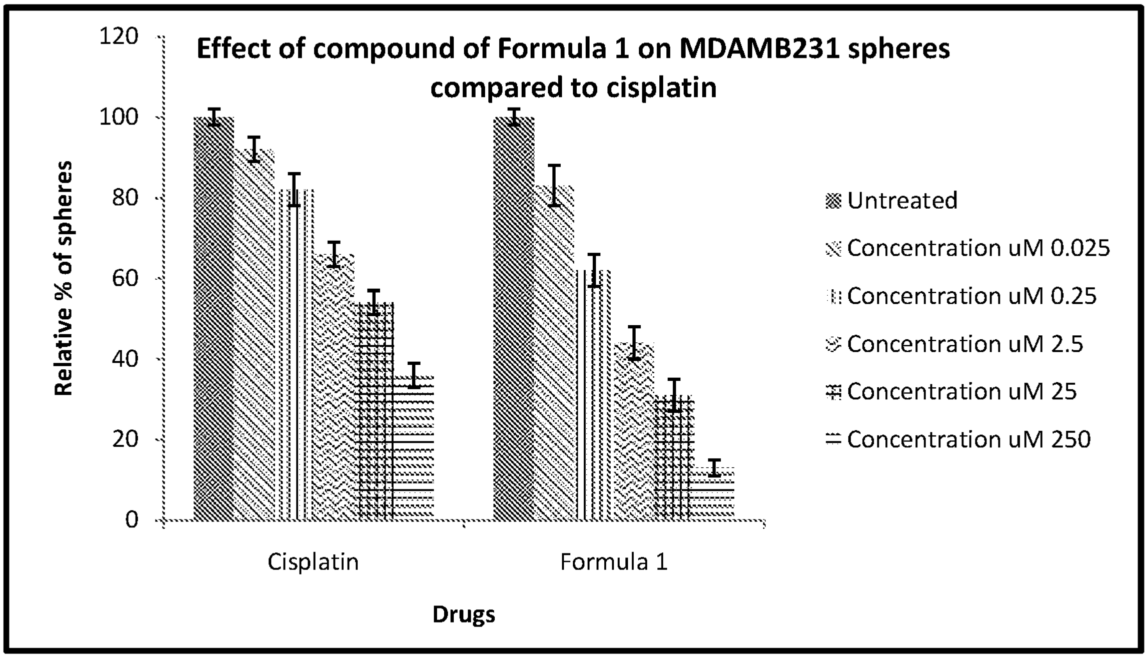
FIG. 1 illustrates the sphere analysis of MDAMB231 cell line in the presence of compound of Formula 1 and cisplatin.
Figure 2:
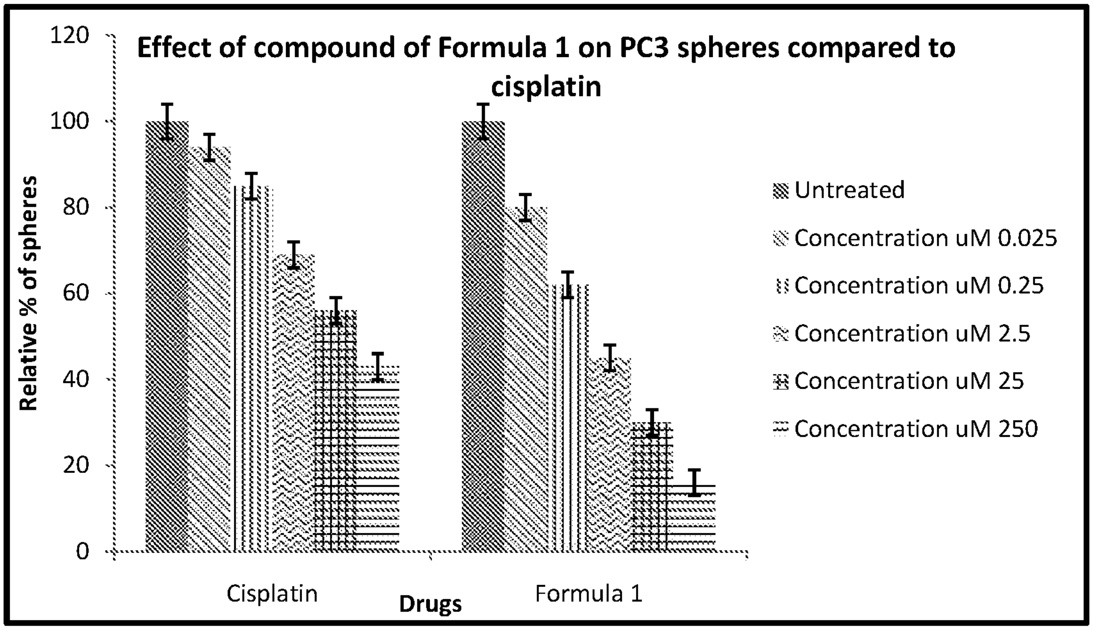
FIG. 2 illustrates the sphere analysis of PC3 cell line in the presence of compound of Formula 1 and cisplatin.
Figure 3:
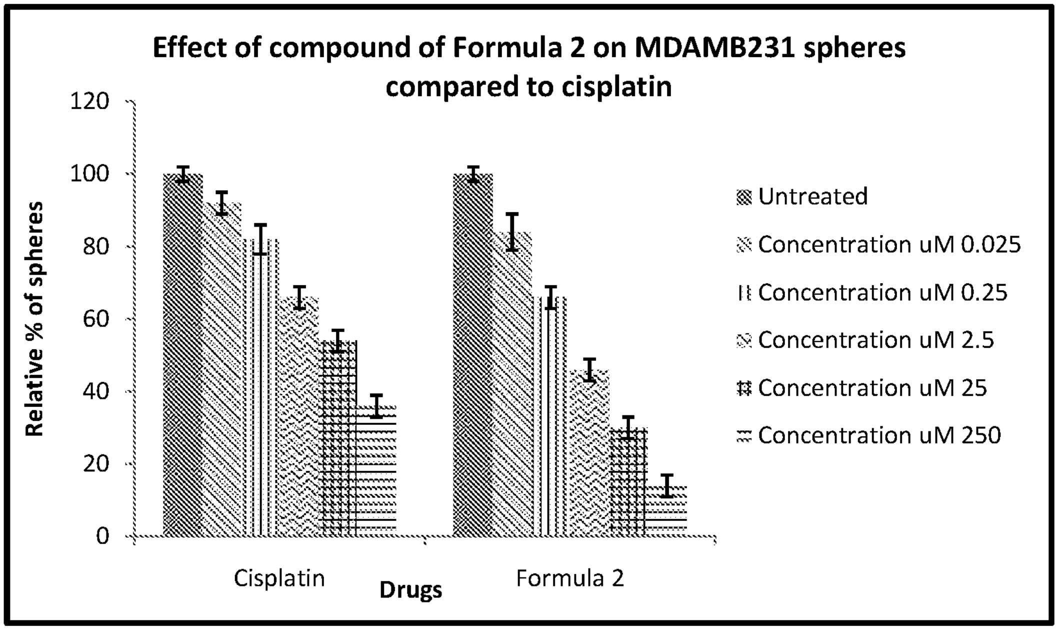
FIG. 3 illustrates the sphere analysis of MDAMB231 cell line in the presence of compound of Formula 2 and cisplatin.
Figure 4:
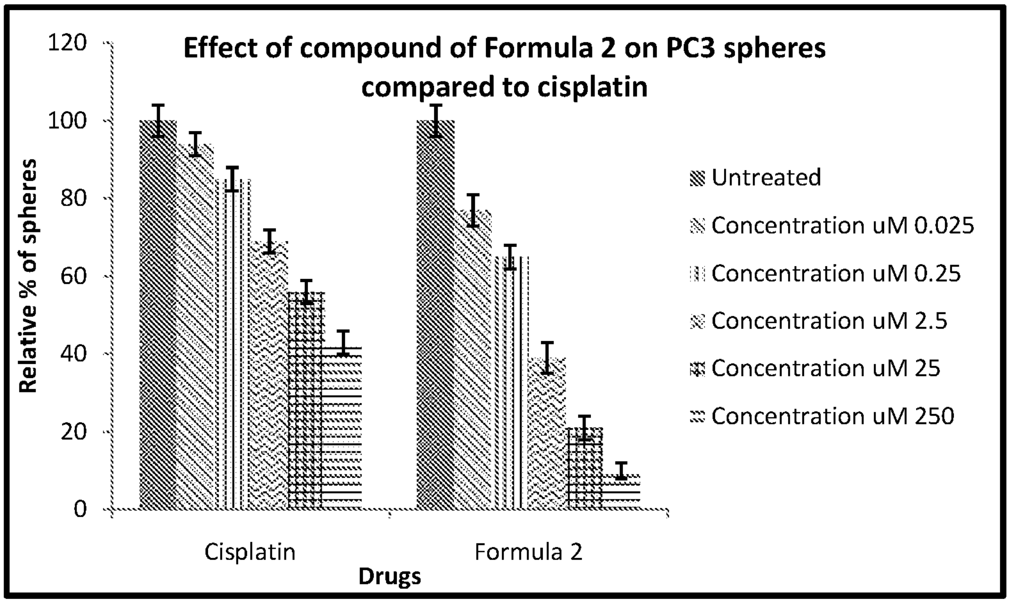
FIG. 4 illustrates the sphere analysis of PC3 cell line in the presence of compound of Formula 2 and cisplatin.
Figure 5:
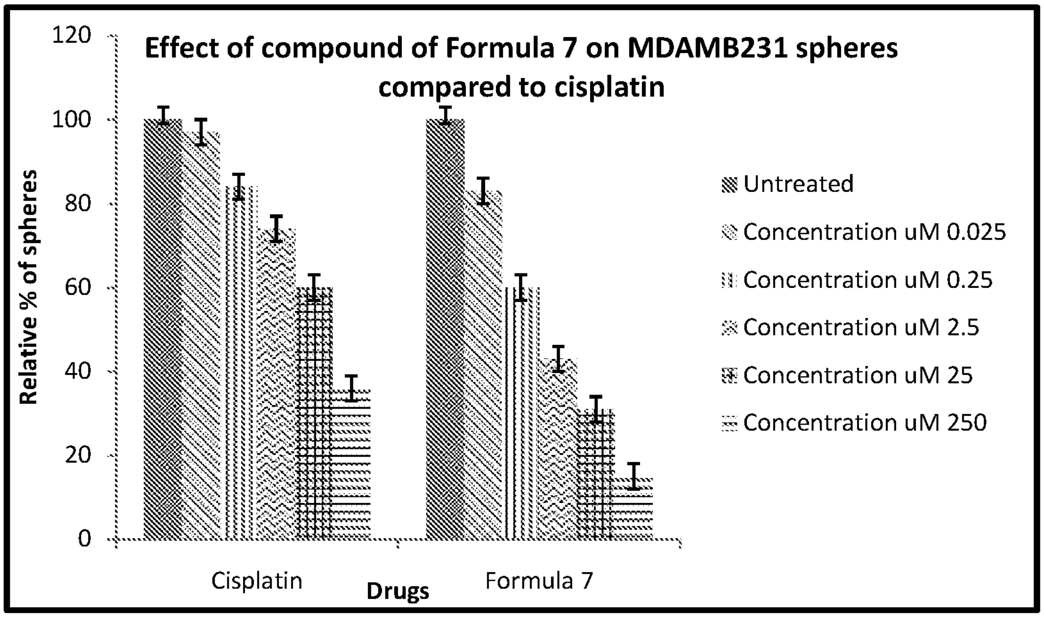
FIG. 5 illustrates the sphere analysis of MDAMB231 cell line in the presence of compound of Formula 7 and cisplatin.
Figure 6:
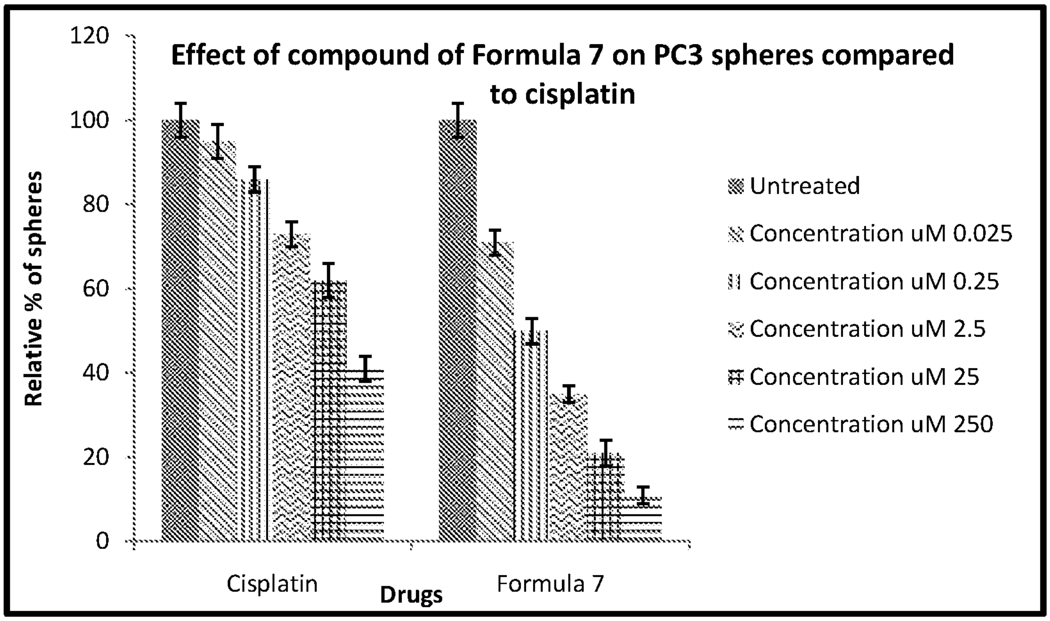
FIG. 6 illustrates the sphere analysis of PC3 cell line in the presence of compound of Formula 7 and cisplatin.
Figure 7:
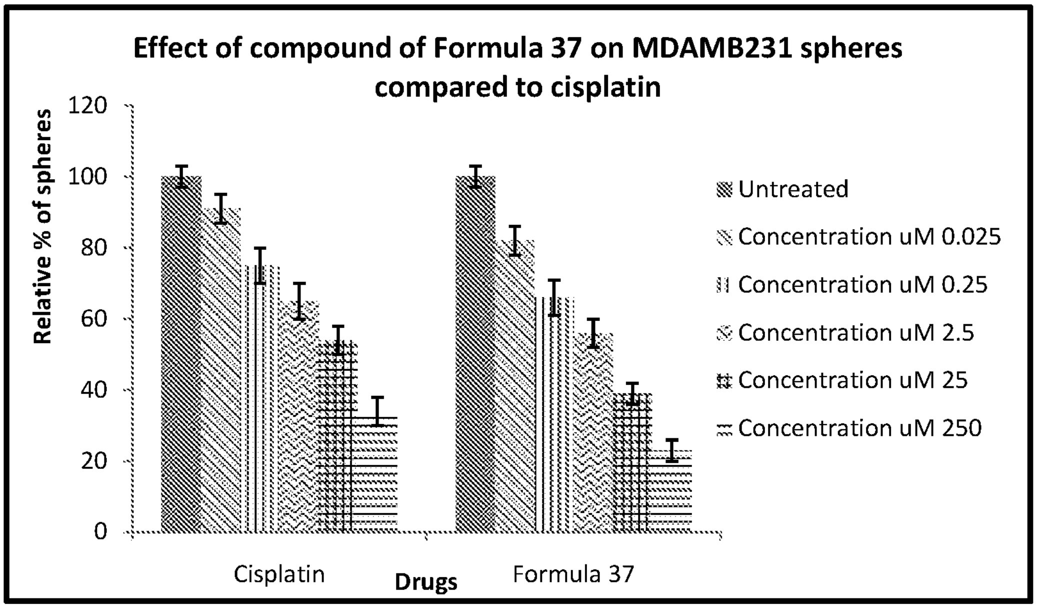
FIG. 7 illustrates the sphere analysis of MDAMB231 cell line in the presence of compound of Formula 37 and cisplatin.
Figure 8:
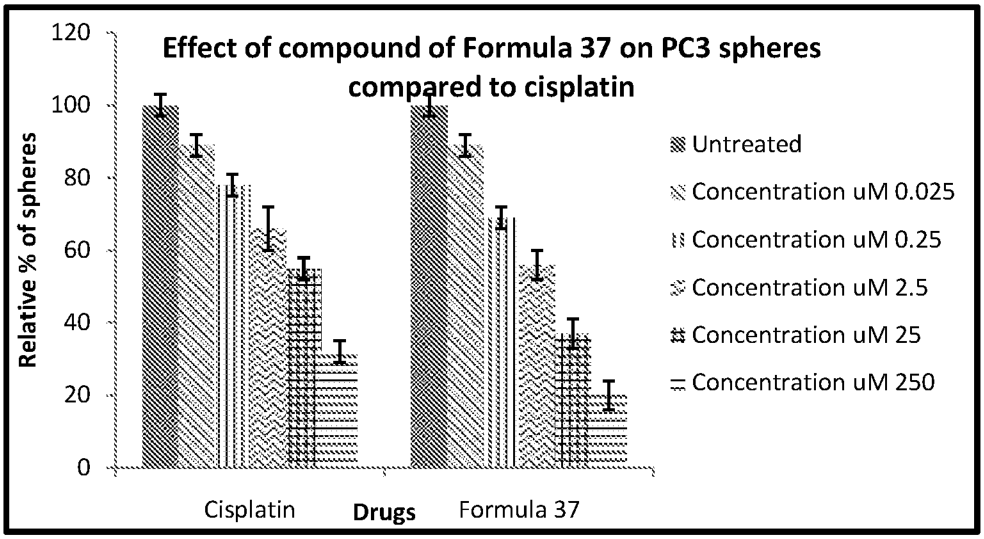
FIG. 8 illustrates the sphere analysis of PC3 cell line in the presence of compound of Formula 37 and cisplatin.
Figure 9:
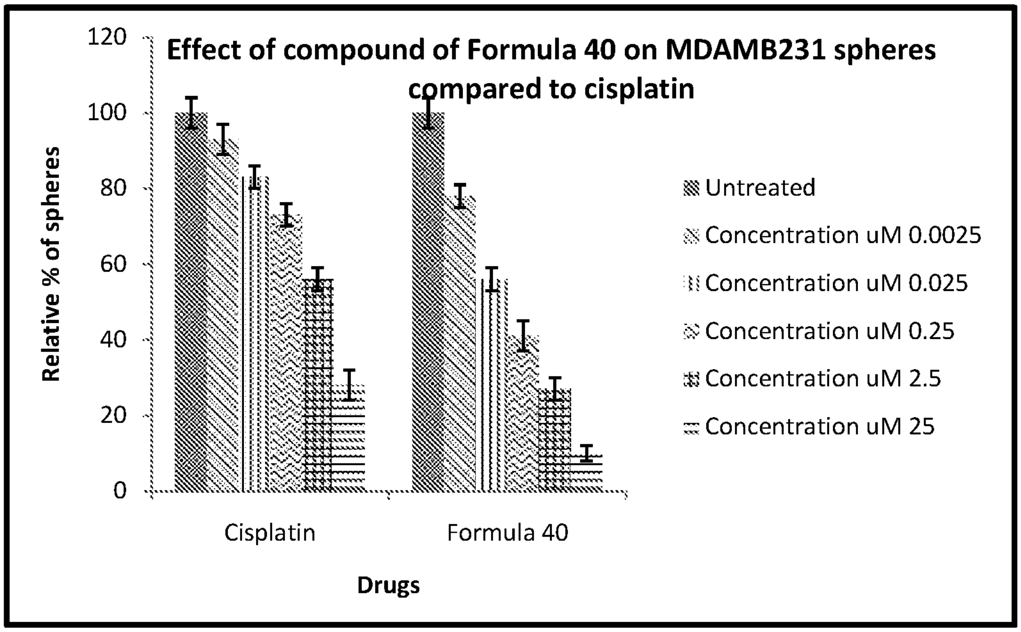
FIG. 9 illustrates the sphere analysis of MDAMB231 cell line in the presence of compound of Formula 40 and cisplatin.
Figure 10:
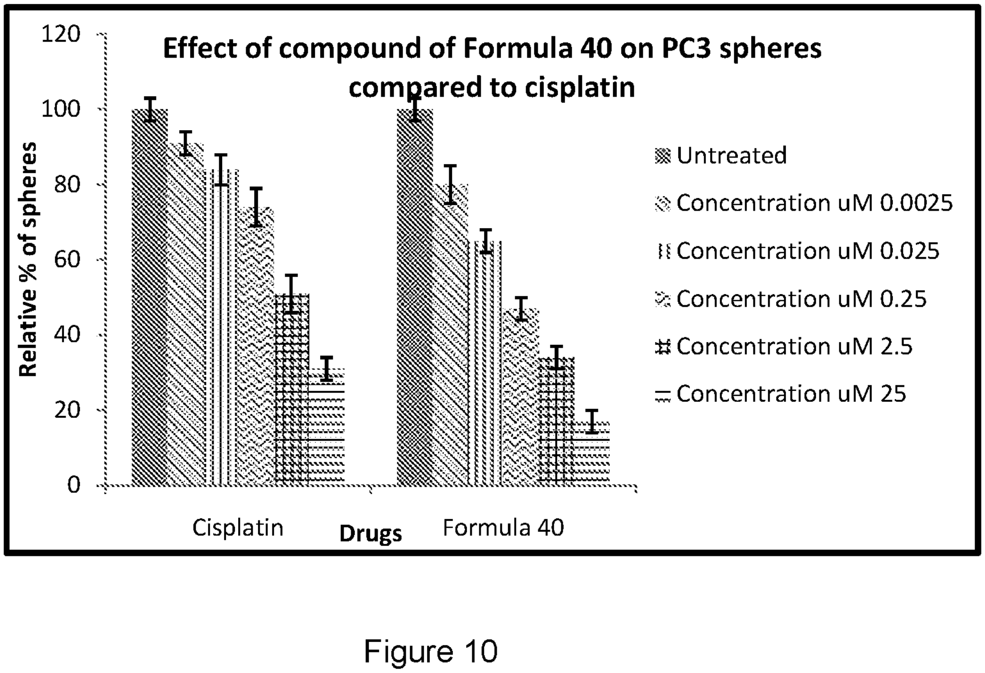
FIG. 10 illustrates the sphere analysis of PC3 cell line in the presence of compound of Formula 40 and cisplatin.
Figure 11:
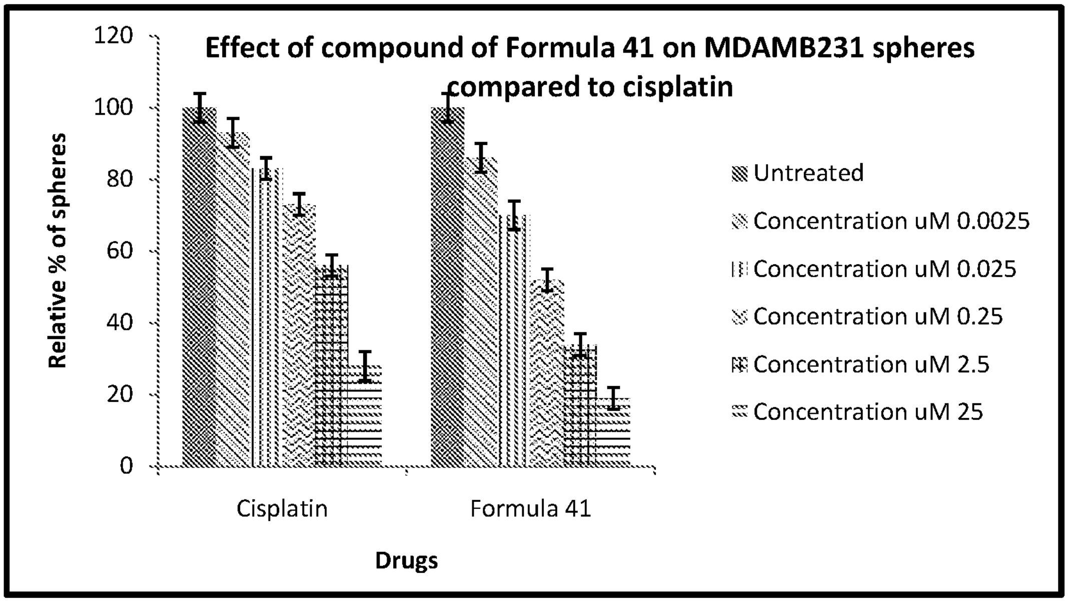
FIG. 11 illustrates the sphere analysis of MDAMB231 cell line in the presence of compound of Formula 41 and cisplatin.
Figure 12:
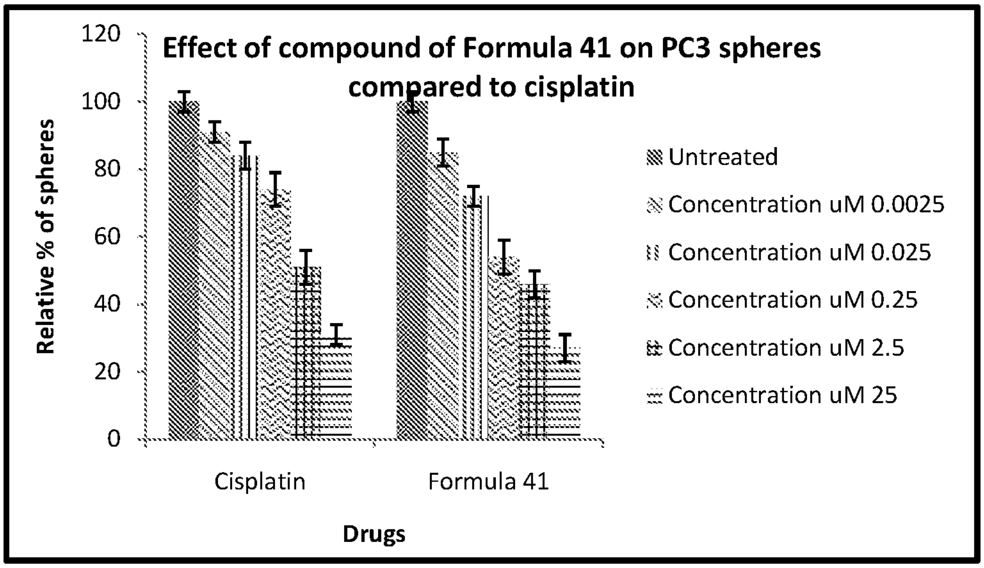
FIG. 12 illustrates the sphere analysis of PC3 cell line in the presence of compound of Formula 41 and cisplatin.
Figure 13:
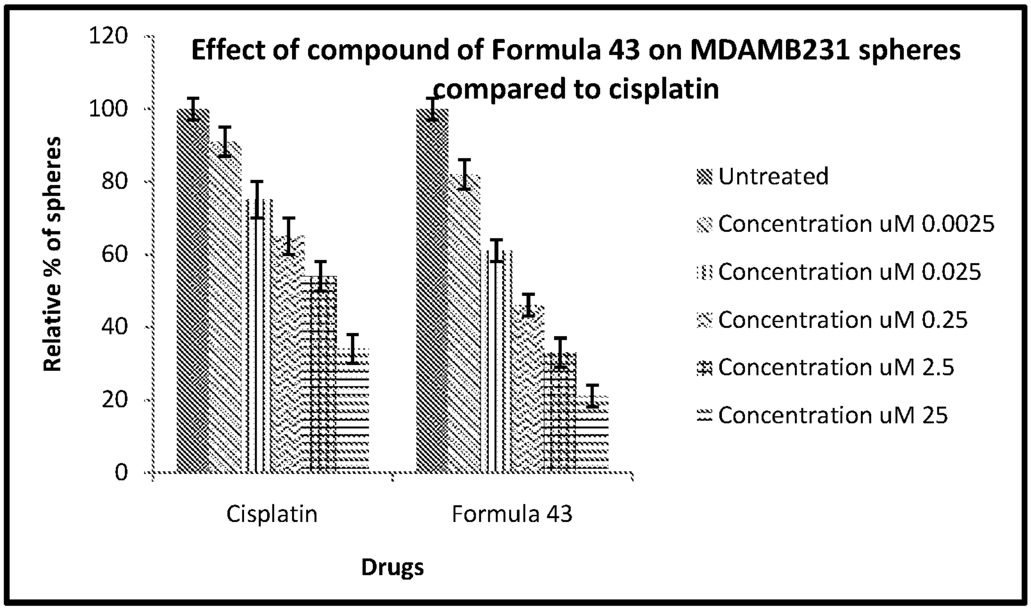
FIG. 13 illustrates the sphere analysis of MDAMB231 cell line in the presence of compound of Formula 43 and cisplatin.
Figure 14:
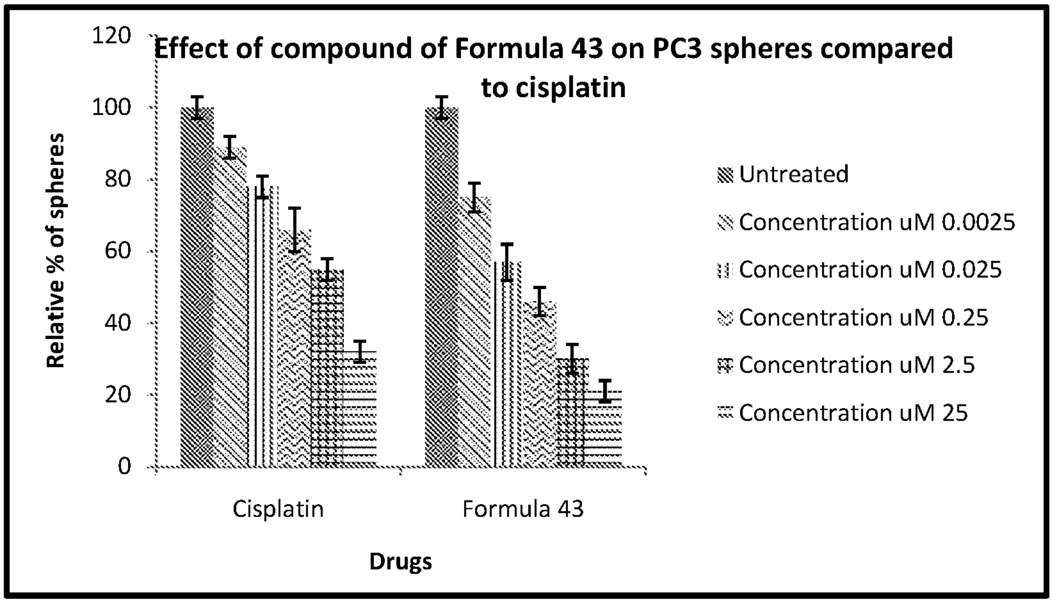
FIG. 14 illustrates the sphere analysis of PC3 cell line in the presence of compound of Formula 43 and cisplatin.
Figure 15:
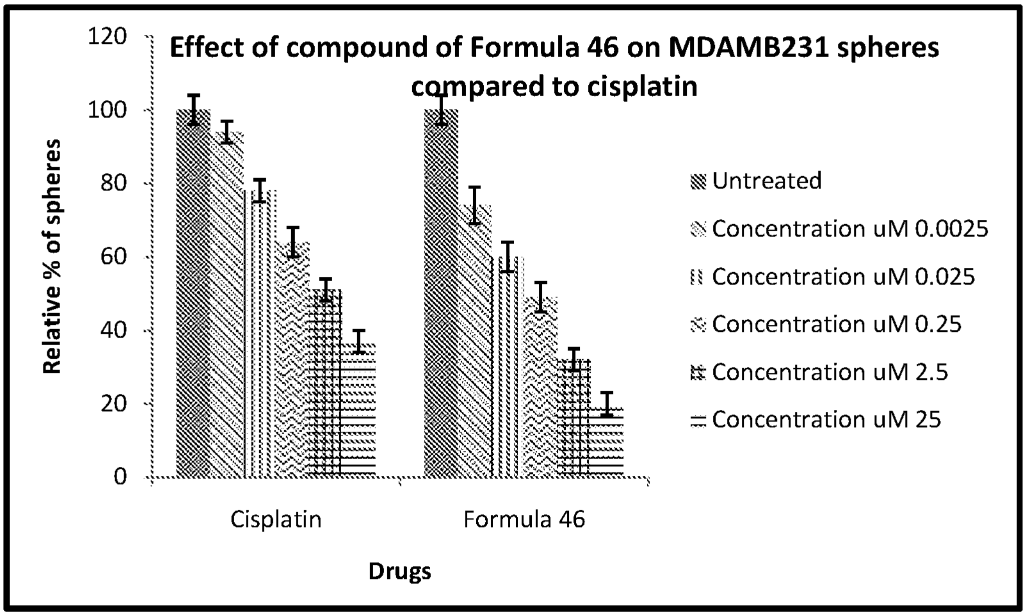
FIG. 15 illustrates the sphere analysis of MDAMB231 cell line in the presence of compound of Formula 46 and cisplatin.
Figure 16:
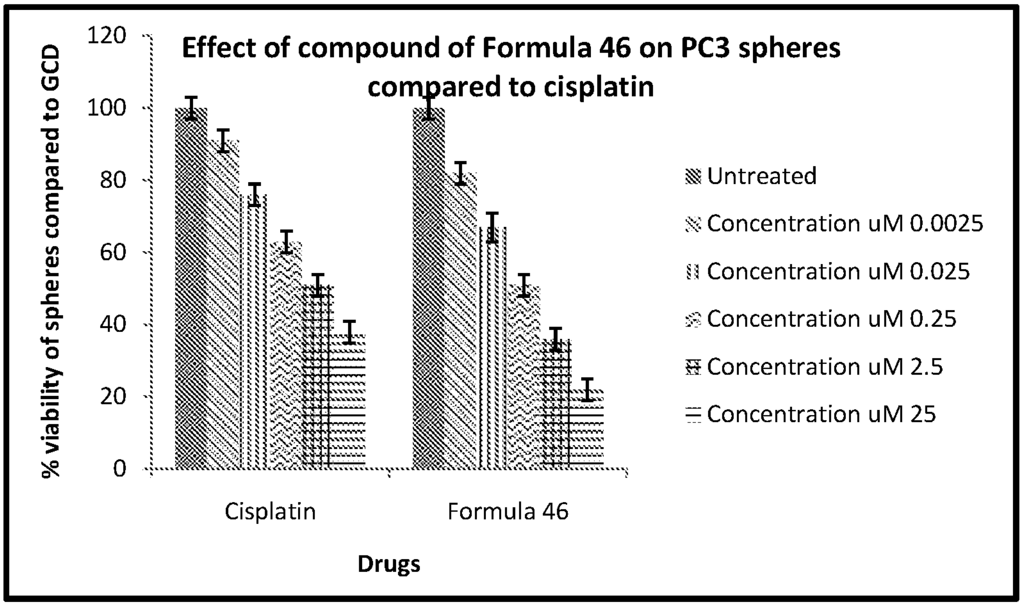
FIG. 16 illustrates the sphere analysis of PC3 cell line in the presence of compound of Formula 46 and cisplatin.
Figure 17:
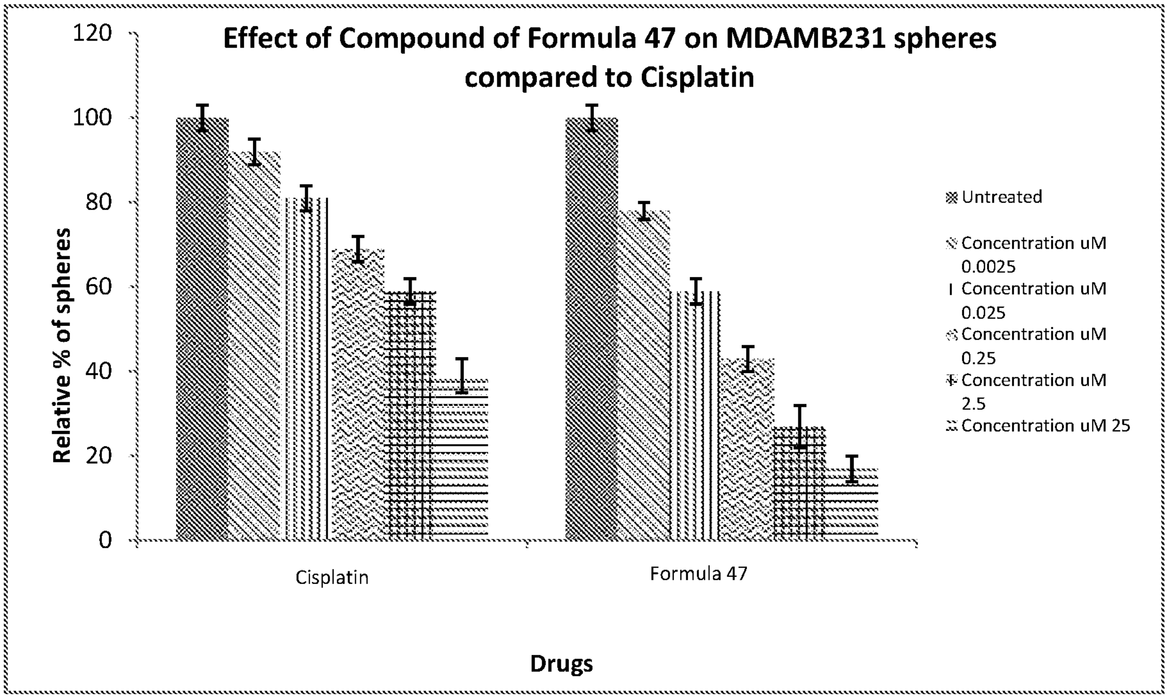
FIG. 17 illustrates the sphere analysis of MDAMB231 cell line in the presence of compound of Formula 47 and cisplatin.
Figure 18:
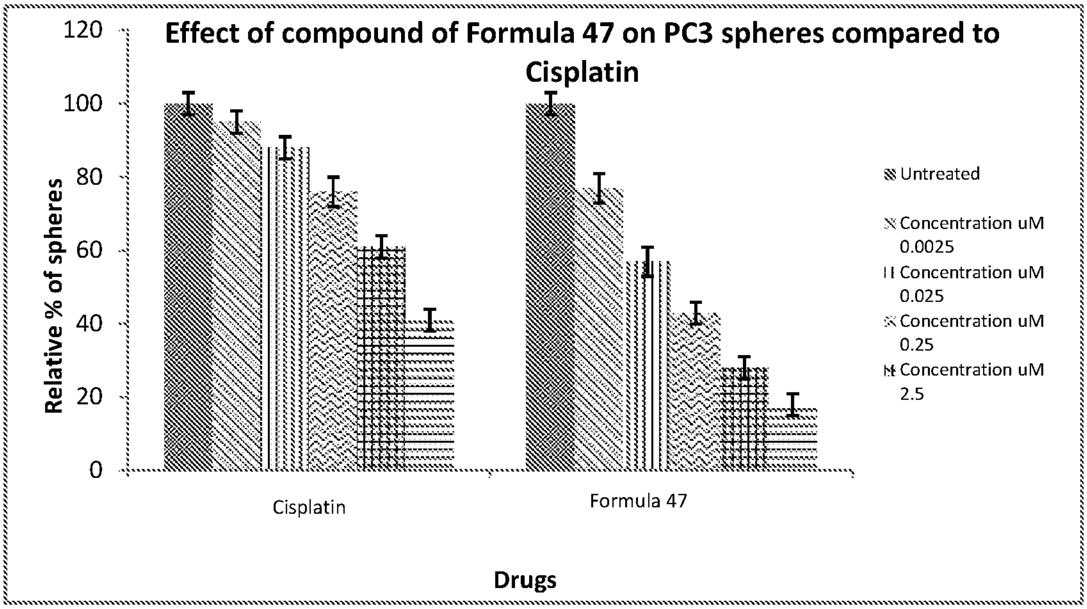
FIG. 18 illustrates the sphere analysis of PC3 cell line in the presence of compound of Formula 47 and cisplatin.
Figure 19:
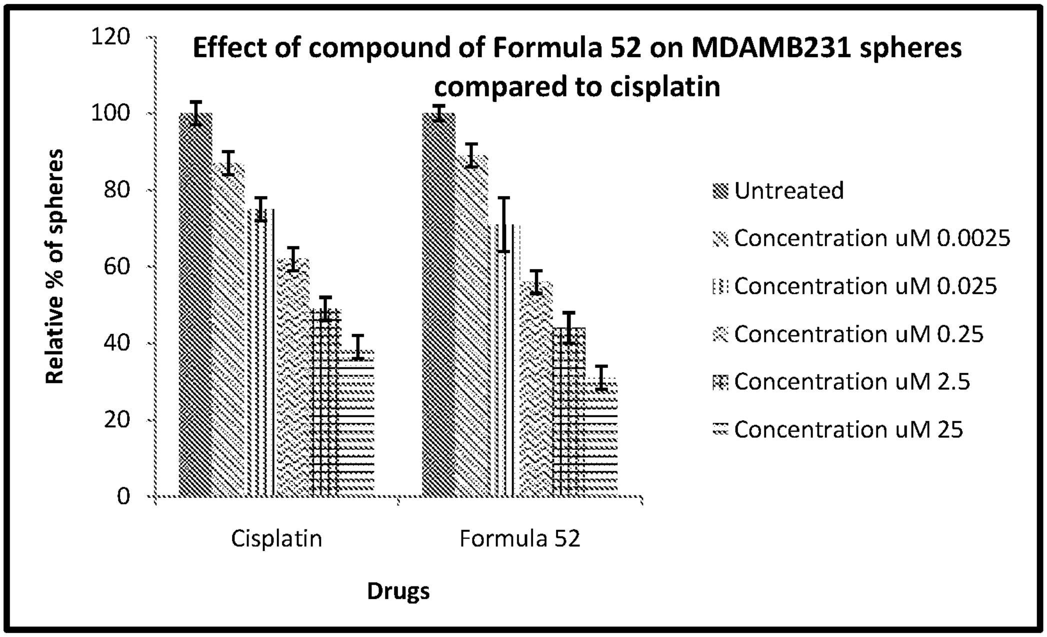
FIG. 19 illustrates the sphere analysis of MDAMB231 cell line in the presence of compound of Formula 52 and cisplatin.
Figure 20:
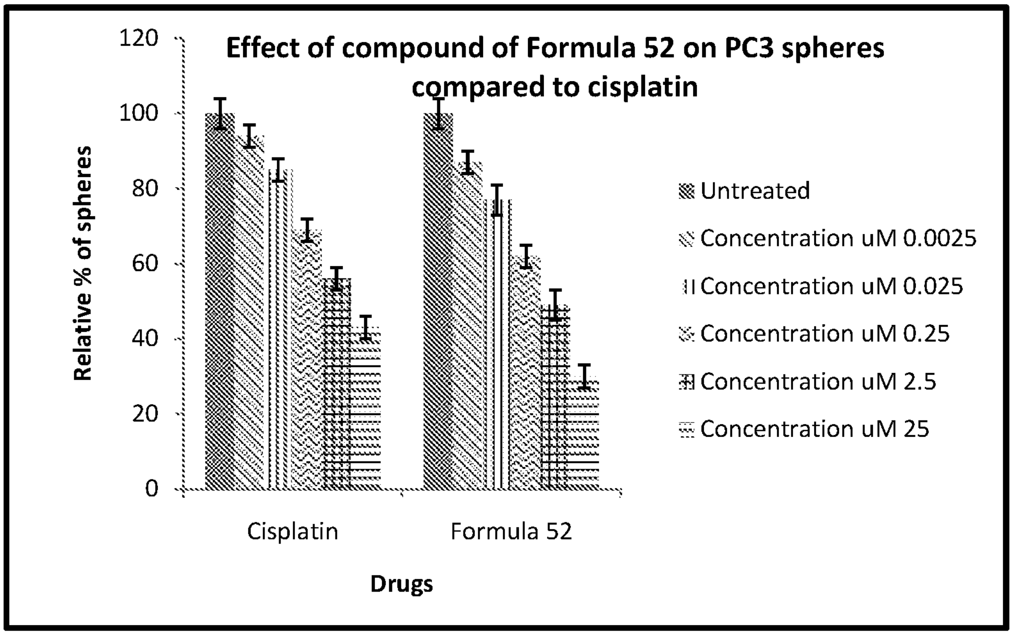
FIG. 20 illustrates the sphere analysis of PC3 cell line in the presence of compound of Formula 52 and cisplatin.
Figure 21:
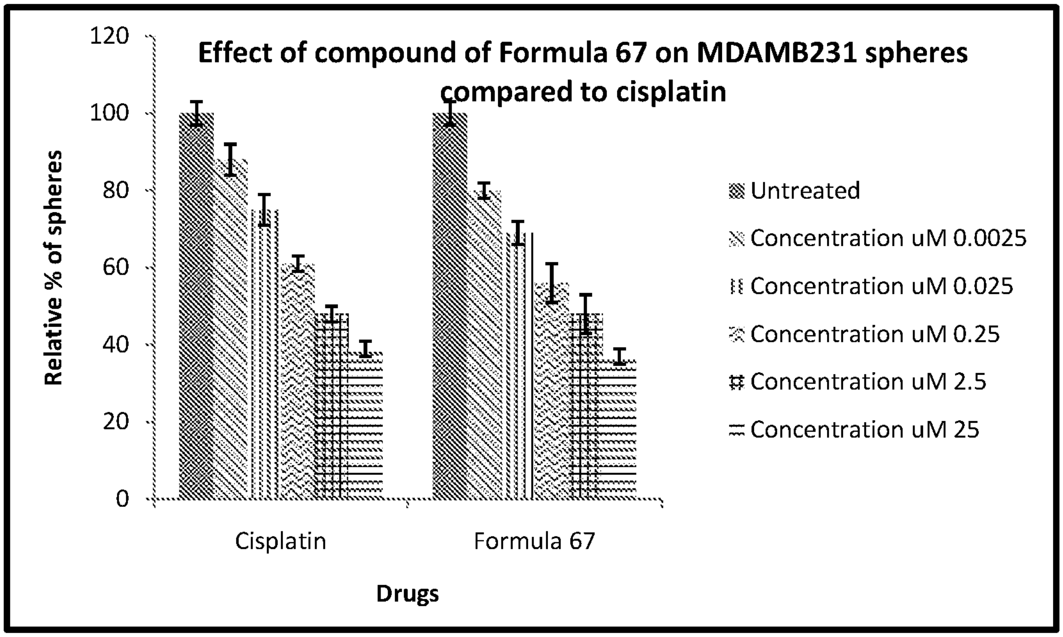
FIG. 21 illustrates the sphere analysis of MDAMB231 cell line in the presence of compound of Formula 67 and cisplatin.
Figure 22:
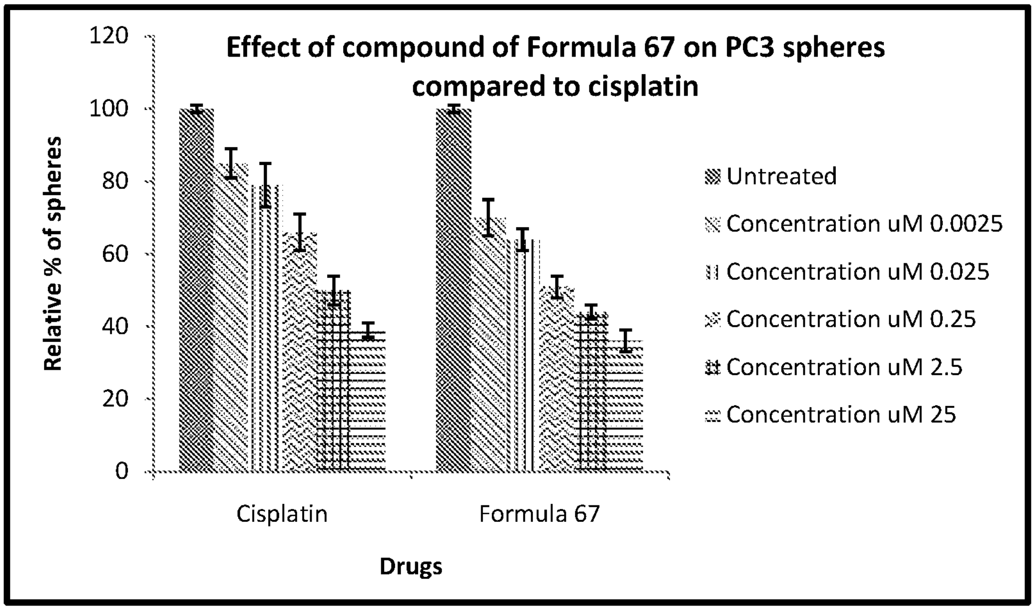
FIG. 22 illustrates the sphere analysis of PC3 cell line in the presence of compound of Formula 67 and cisplatin.
Figure 23:
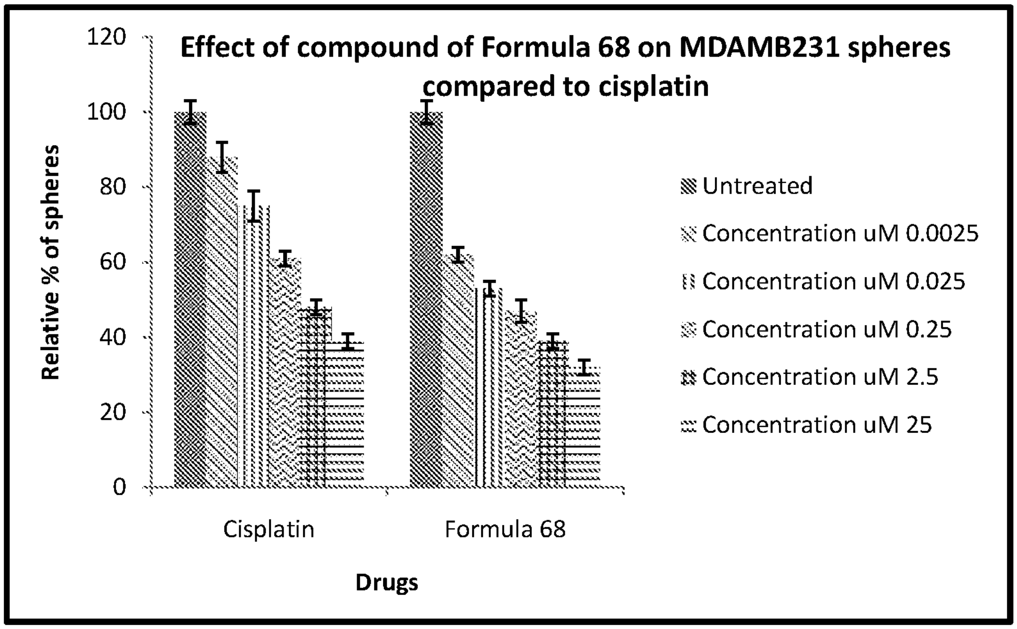
FIG. 23 illustrates the sphere analysis of MDAMB231 cell line in the presence of compound of Formula 68 and cisplatin.
Figure 24:
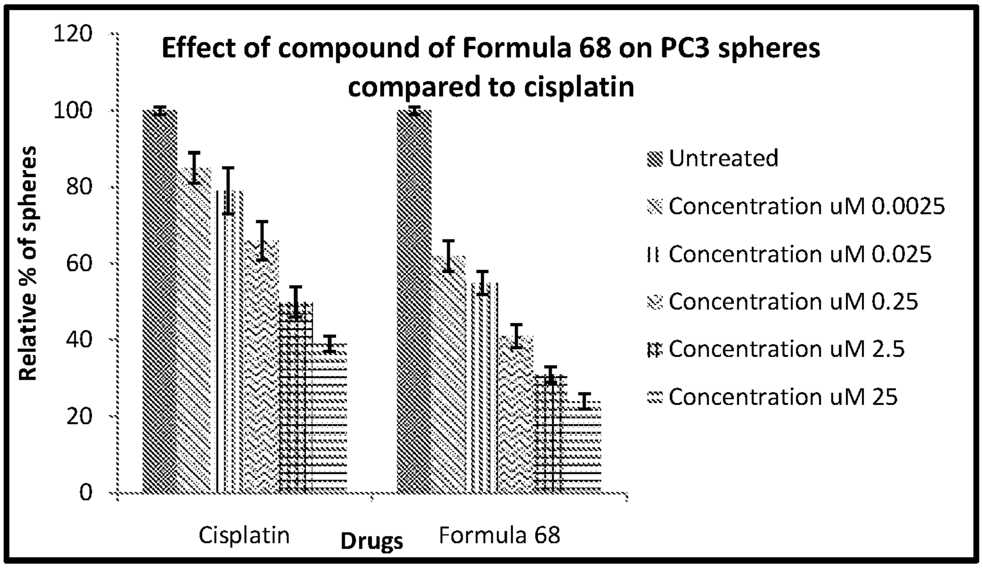
FIG. 24 illustrates the sphere analysis of PC3 cell line in the presence of compound of Formula 68 and cisplatin.
Figure 25:
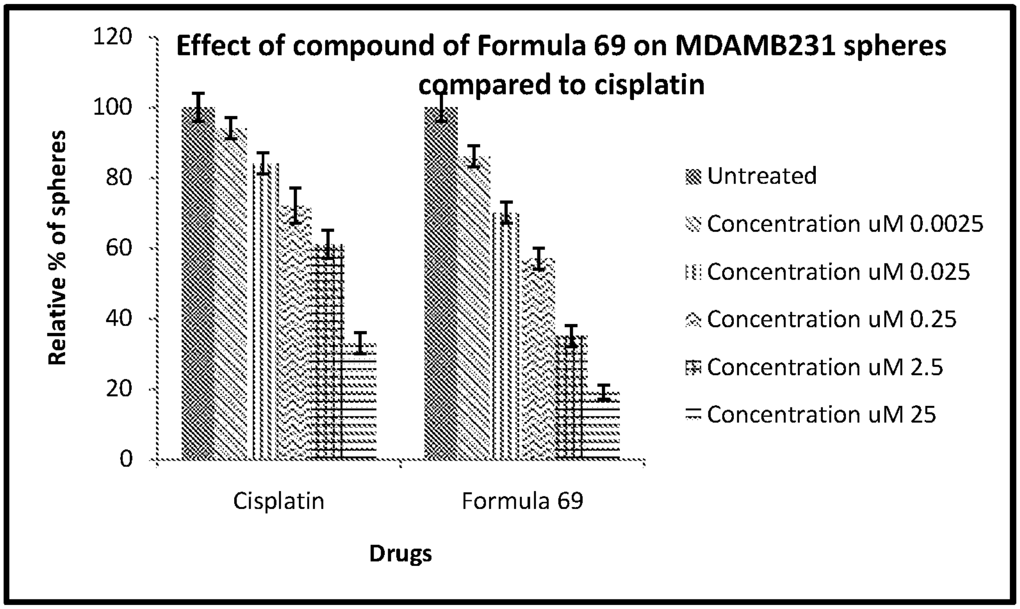
FIG. 25 illustrates the sphere analysis of MDAMB231 cell line in the presence of compound of Formula 69 and cisplatin.
Figure 26:
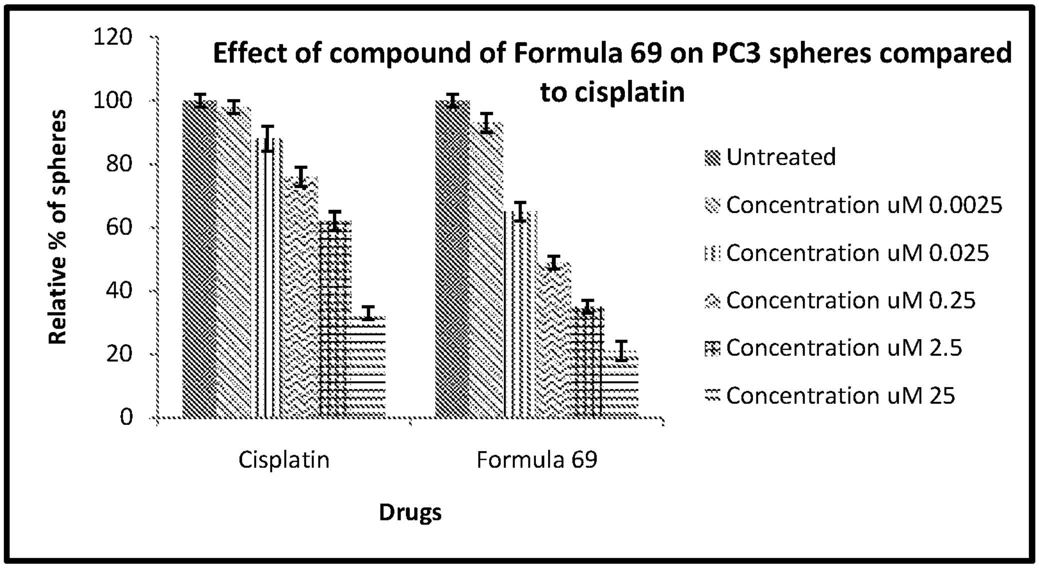
FIG. 26 illustrates the sphere analysis of PC3 cell line in the presence of compound of Formula 69 and cisplatin.
Figure 27:
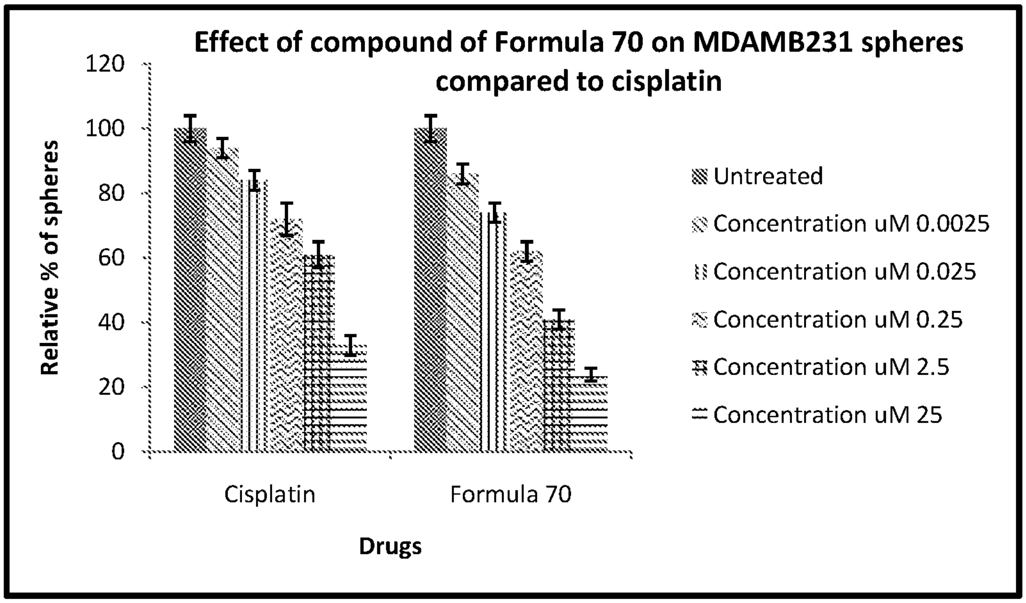
FIG. 27 illustrates the sphere analysis of MDAMB231 cell line in the presence of compound of Formula 70 and cisplatin.
Figure 28:
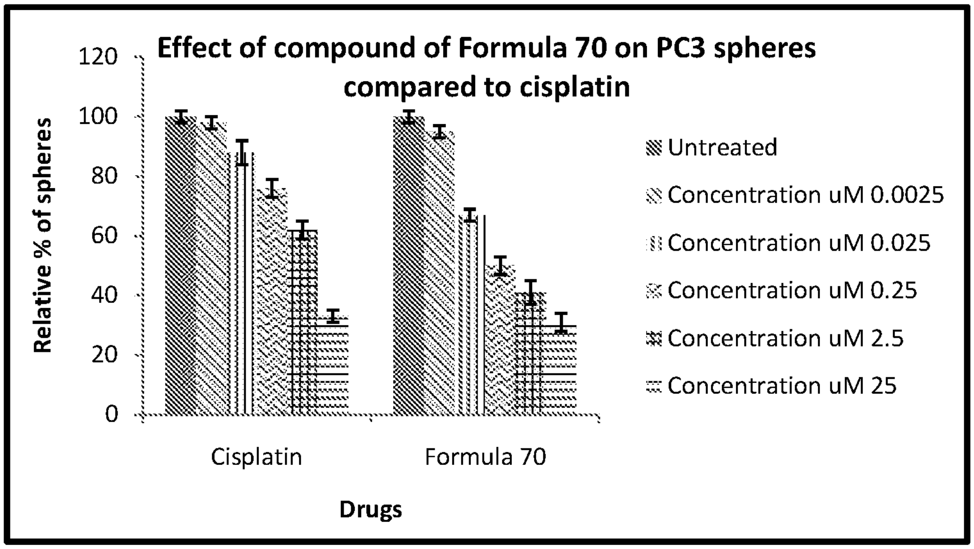
FIG. 28 illustrates the sphere analysis of PC3 cell line in the presence of compound of Formula 70 and cisplatin.
Figure 29:
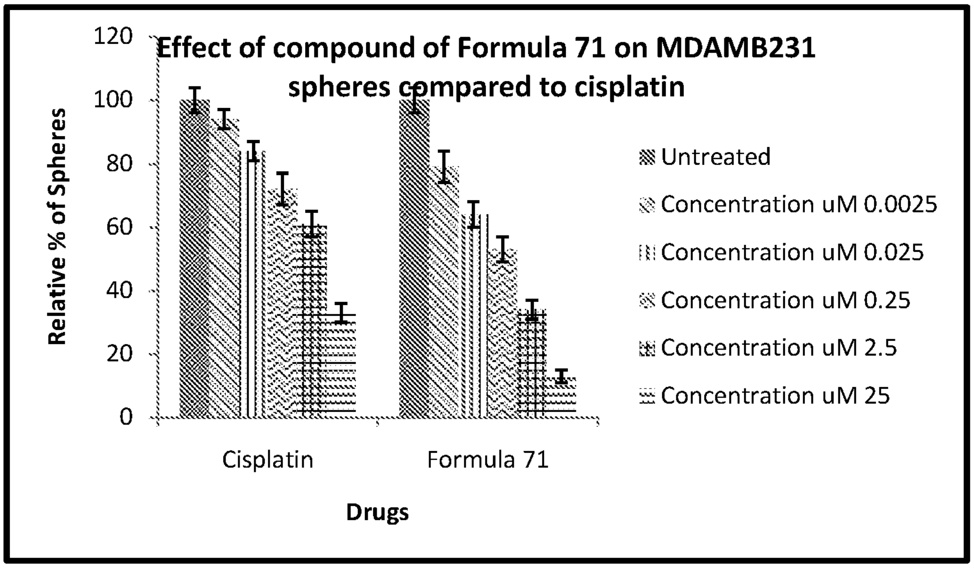
FIG. 29 illustrates the sphere analysis of MDAMB231 cell line in the presence of compound of Formula 71 and cisplatin.
Figure 30:
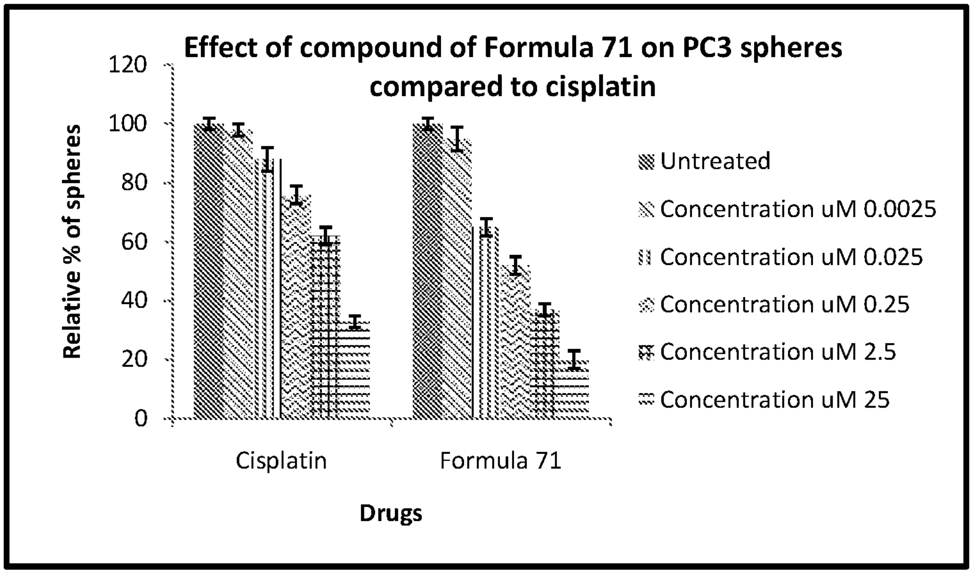
FIG. 30 illustrates the sphere analysis of PC3 cell line in the presence of compound of Formula 71 and cisplatin.
Figure 31:
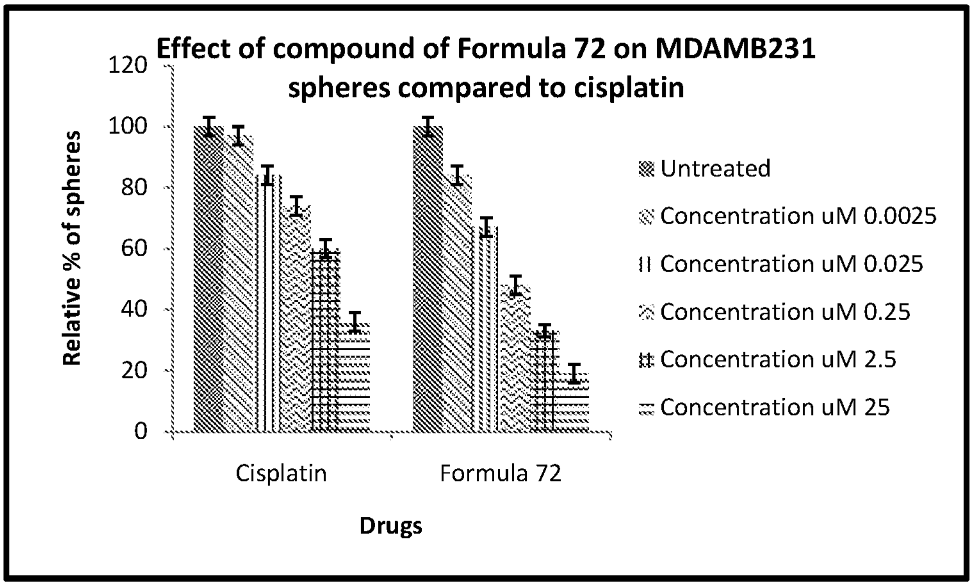
FIG. 31 illustrates the sphere analysis of MDAMB231 cell line in the presence of compound of Formula 72 and cisplatin.
Figure 32:
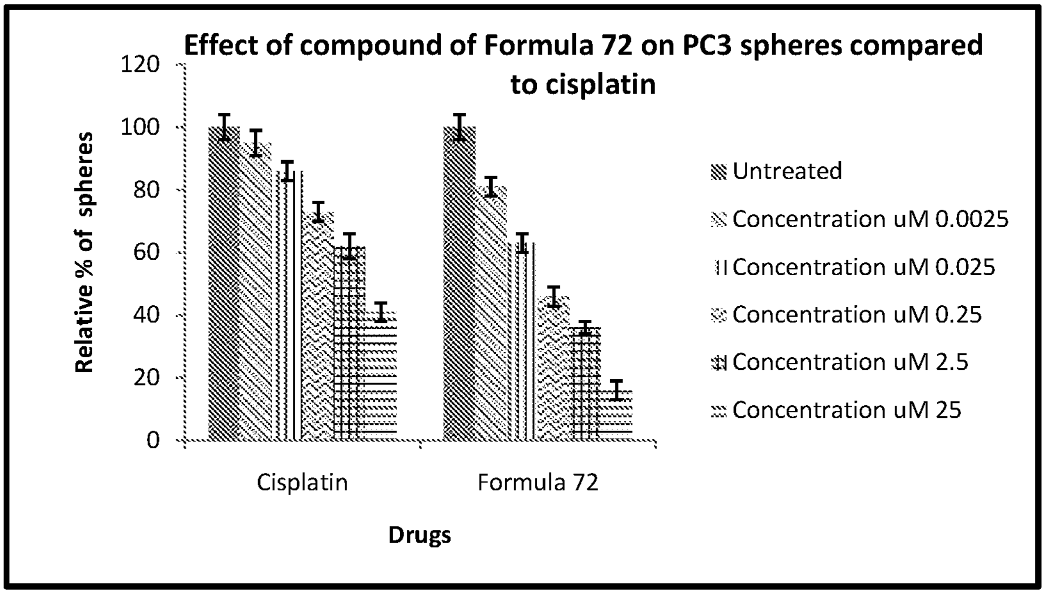
FIG. 32 illustrates the sphere analysis of PC3 cell line in the presence of compound of Formula 72 and cisplatin.
Figure 33:
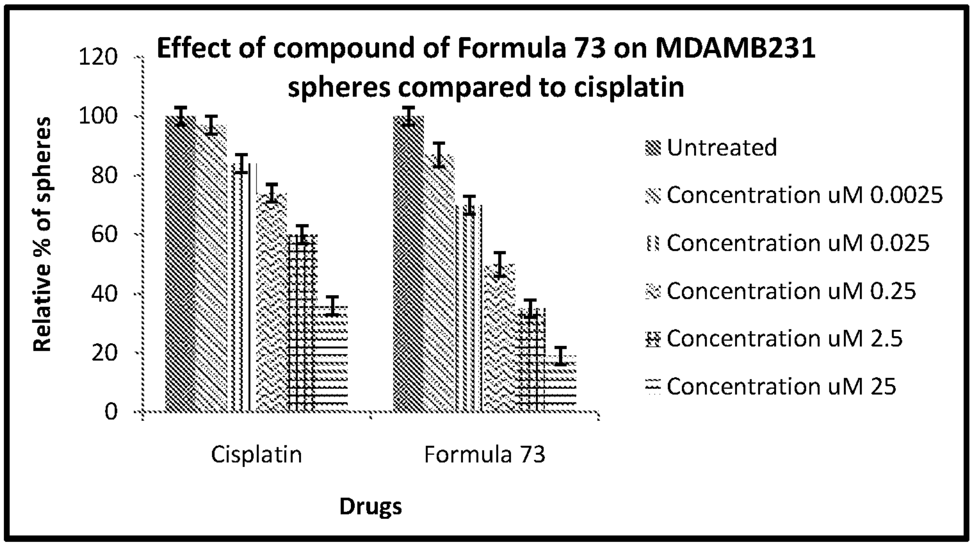
FIG. 33 illustrates the sphere analysis of MDAMB231 cell line in the presence of compound of Formula 73 and cisplatin.
Figure 34:
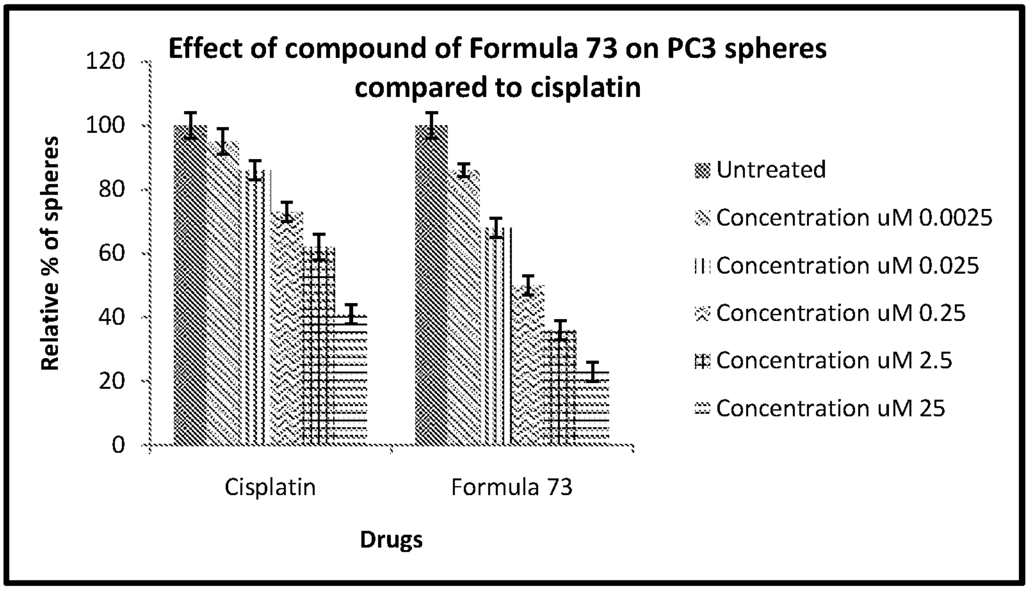
FIG. 34 illustrates the sphere analysis of PC3 cell line in the presence of compound of Formula 73 and cisplatin.
Figure 35:
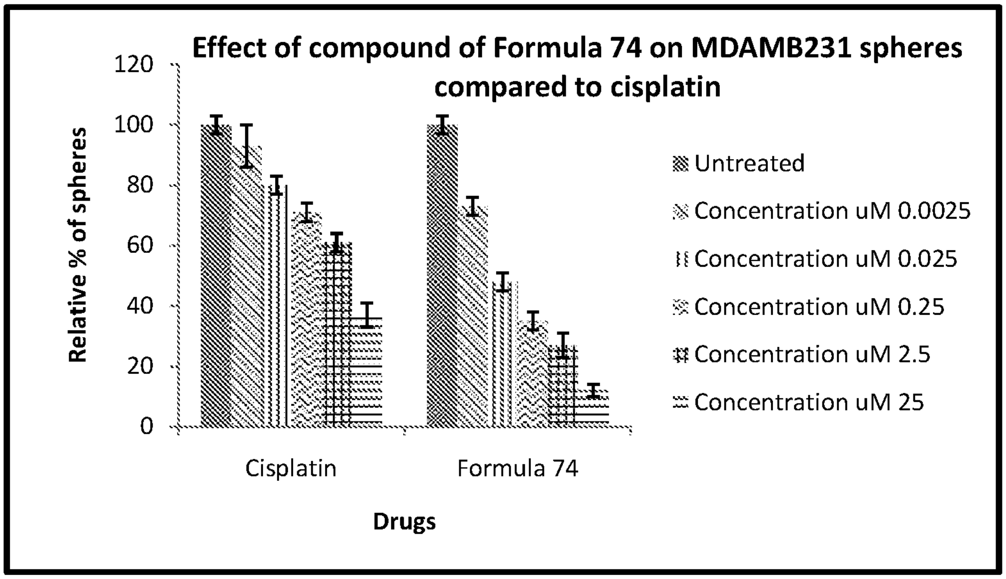
FIG. 35 illustrates the sphere analysis of MDAMB231 cell line in the presence of compound of Formula 74 and cisplatin.
Figure 36:
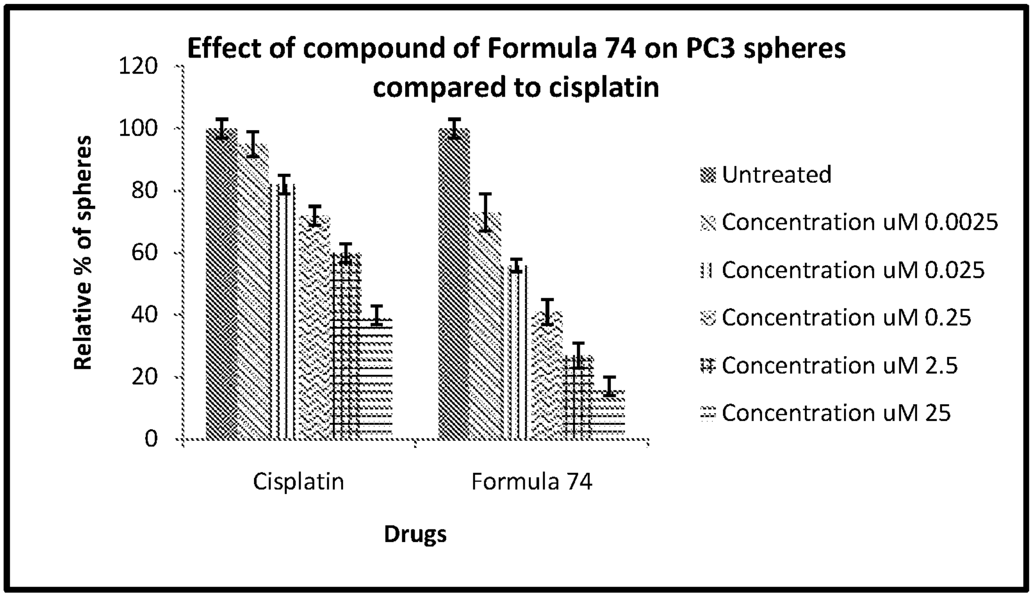
FIG. 36 illustrates the sphere analysis of PC3 cell line in the presence of compound of Formula 74 and cisplatin.
Figure 37:
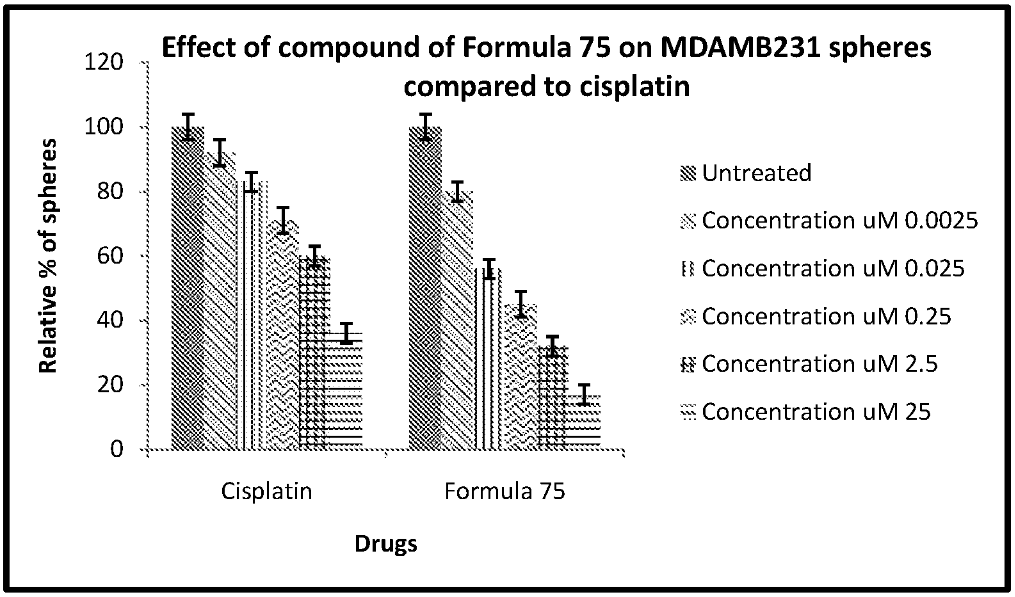
FIG. 37 illustrates the sphere analysis of MDAMB231 cell line in the presence of compound of Formula 75 and cisplatin.
Figure 38:
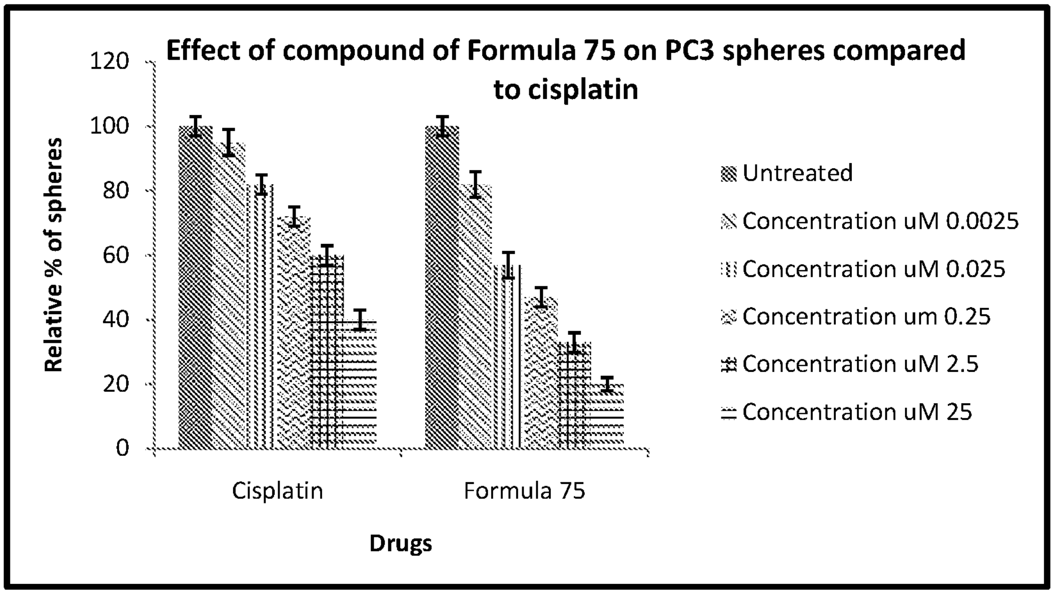
FIG. 38 illustrates the sphere analysis of PC3 cell line in the presence of compound of Formula 75 and cisplatin.
Figure 39:
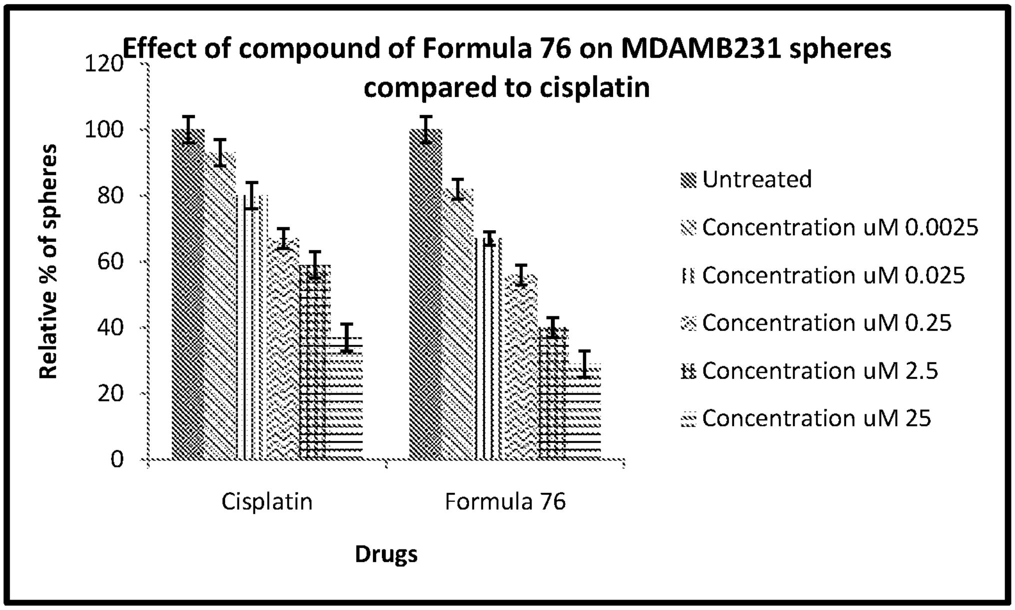
FIG. 39 illustrates the sphere analysis of MDAMB231 cell line in the presence of compound of Formula 76 and cisplatin.
Figure 40:
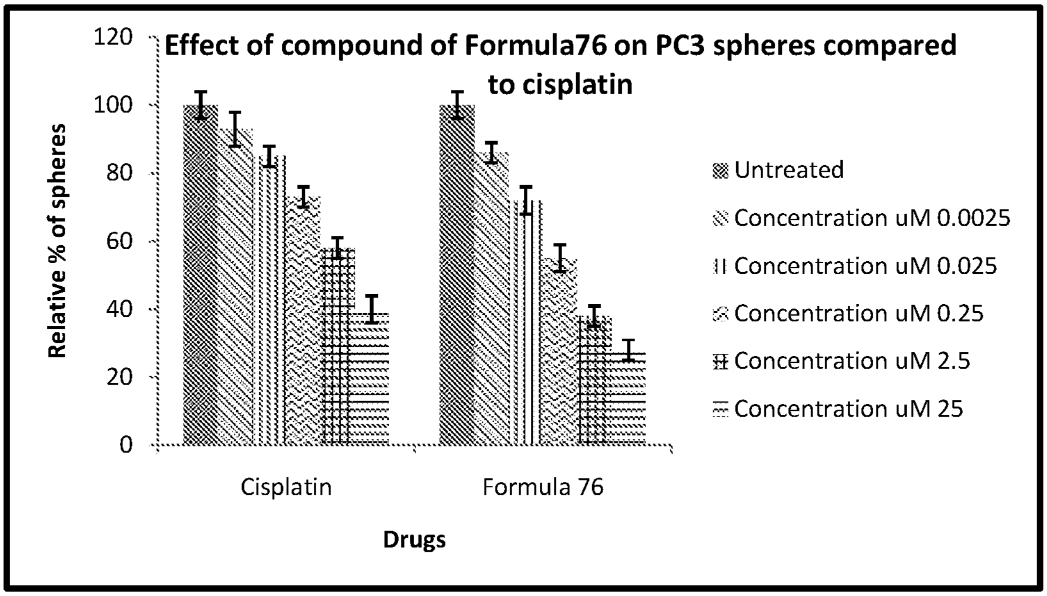
FIG. 40 illustrates the sphere analysis of PC3 cell line in the presence of compound of Formula 76 and cisplatin.
Figure 41:
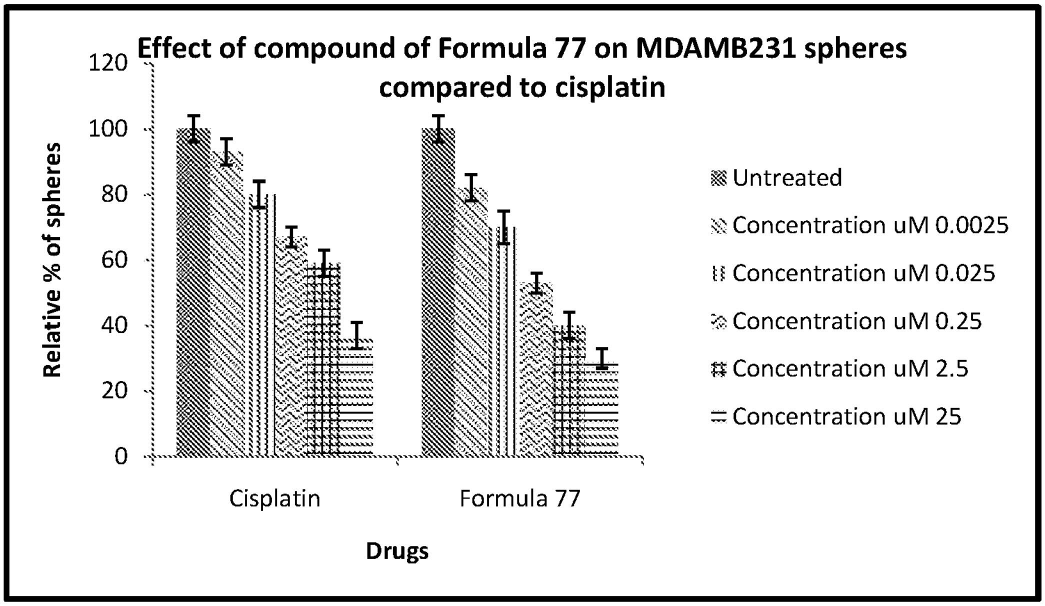
FIG. 41 illustrates the sphere analysis of MDAMB231 cell line in the presence of compound of Formula 77 and cisplatin.
Figure 42:
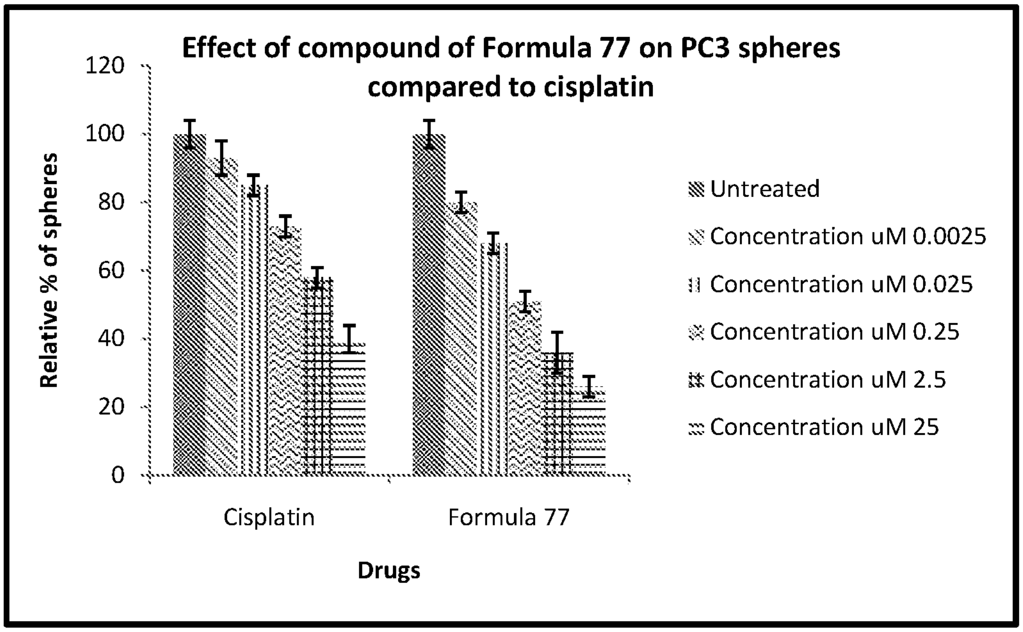
FIG. 42 illustrates the sphere analysis of PC3 cell line in the presence of compound of Formula 77 and cisplatin.
Figure 43:
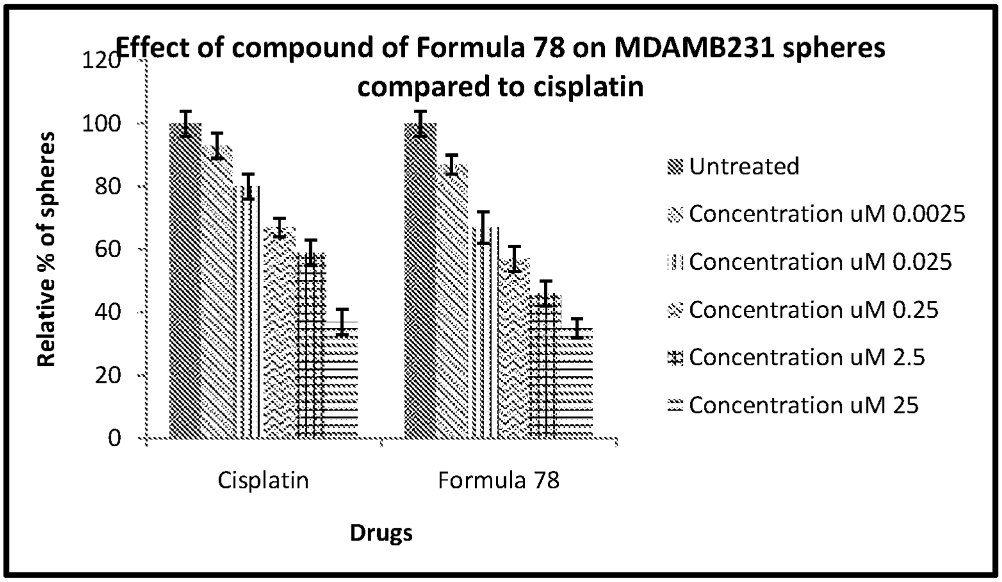
FIG. 43 illustrates the sphere analysis of MDAMB231 cell line in the presence of compound of Formula 78 and cisplatin.
Figure 44:
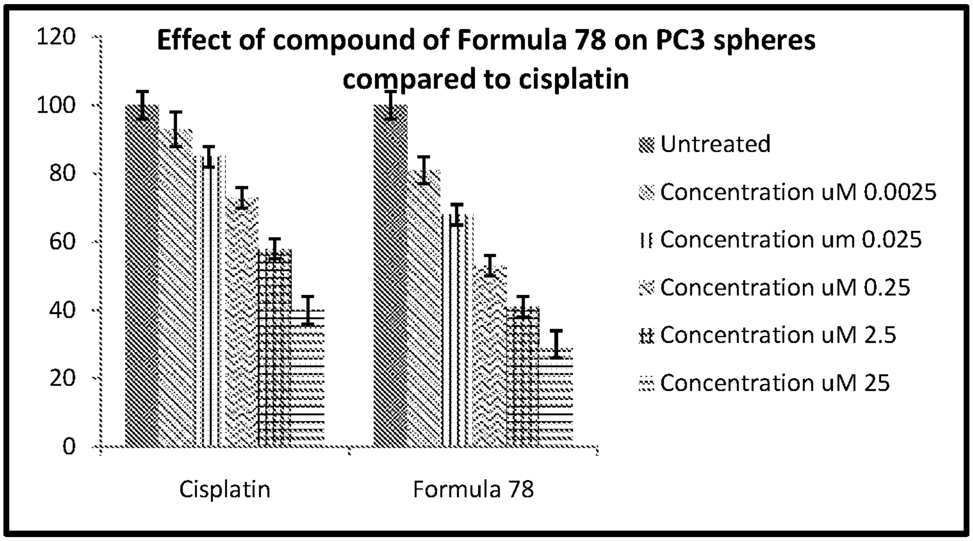
FIG. 44 illustrates the sphere analysis of PC3 cell line in the presence of compound of Formula 78 and cisplatin.
Figure 45:
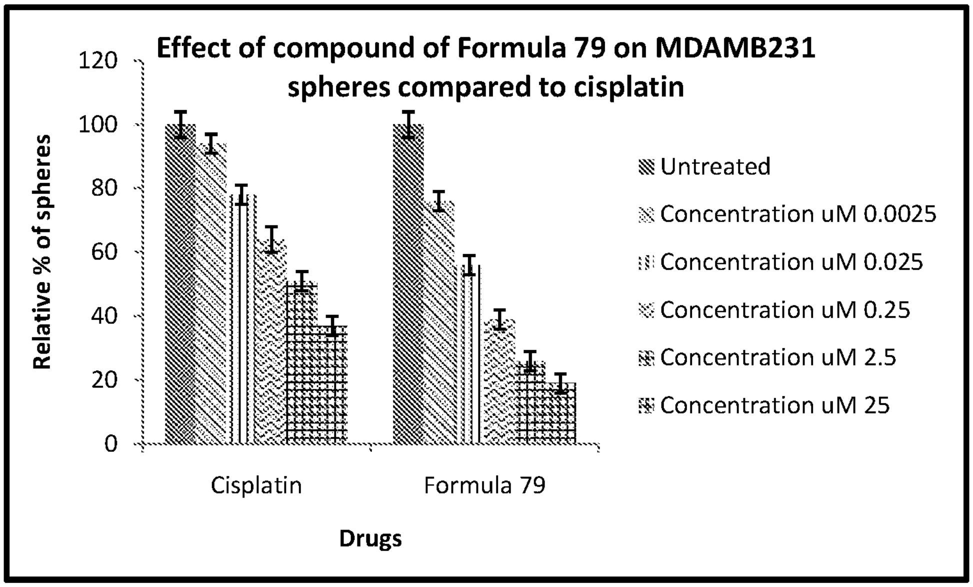
FIG. 45 illustrates the sphere analysis of MDAMB231 cell line in the presence of compound of Formula 79 and cisplatin.
Figure 46:
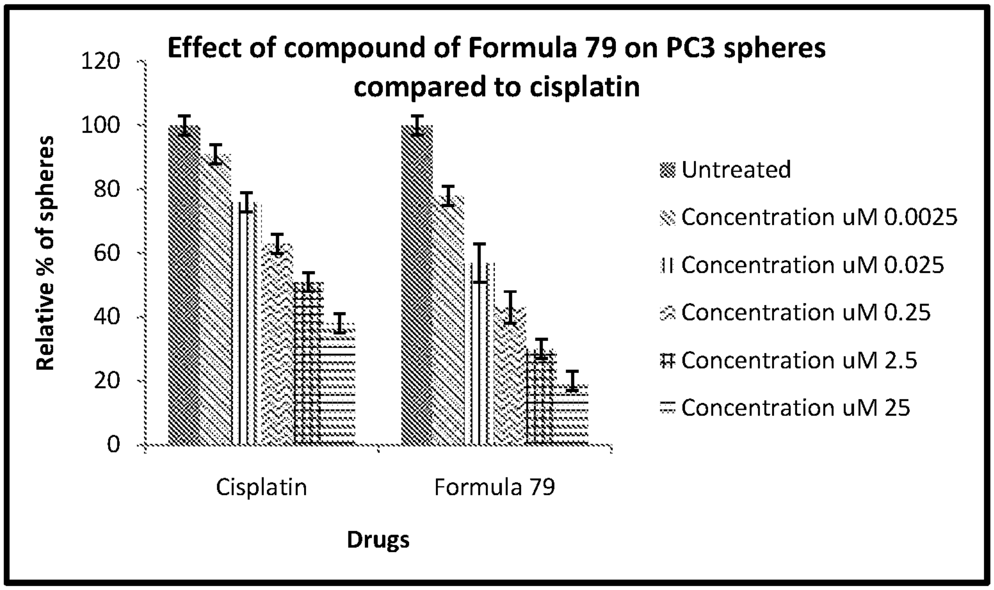
FIG. 46 illustrates the sphere analysis of PC3 cell line in the presence of compound of Formula 79 and cisplatin.
Figure 47:
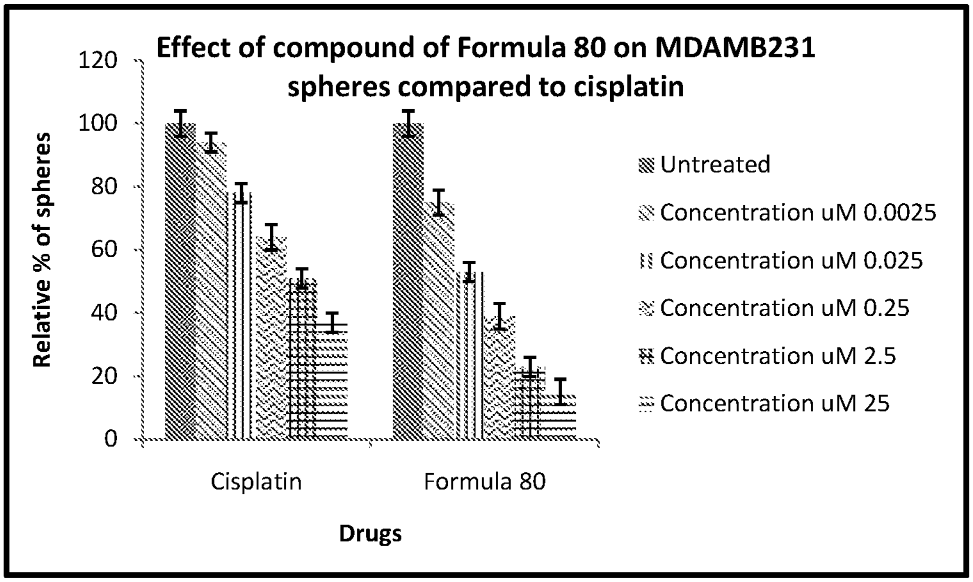
FIG. 47 illustrates the sphere analysis of MDAMB231 cell line in the presence of compound of Formula 80 and cisplatin.
Figure 48:
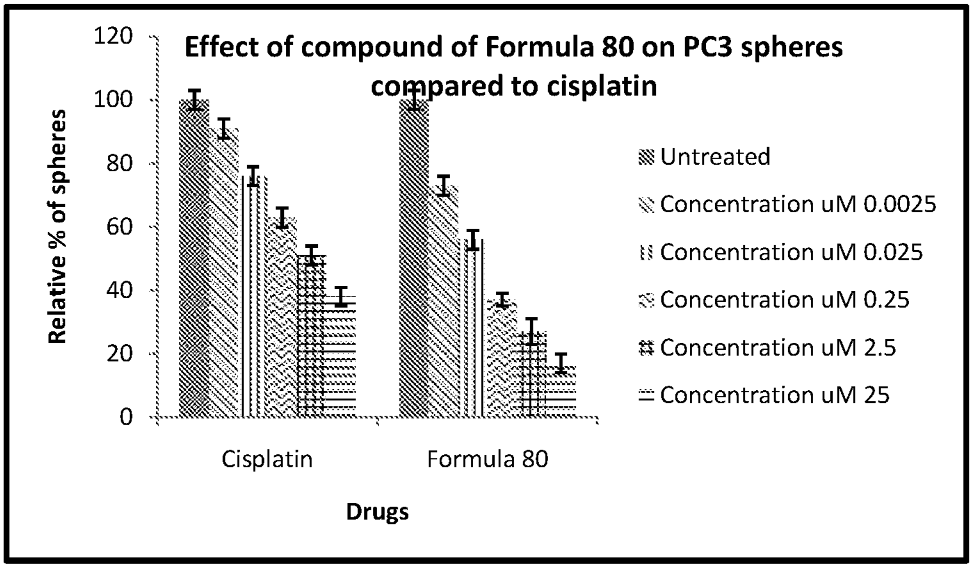
FIG. 48 illustrates the sphere analysis of PC3 cell line in the presence of compound of Formula 80 and cisplatin.
Figure 49:
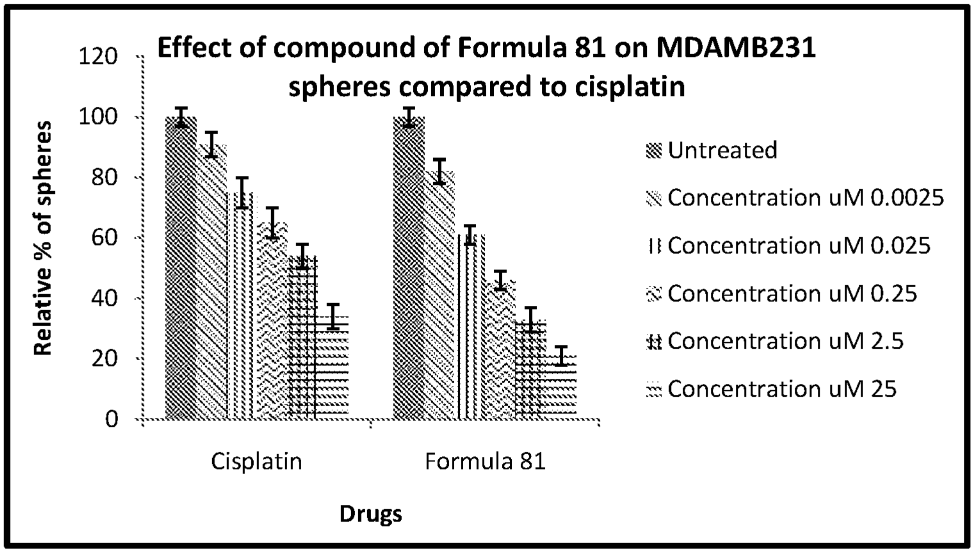
FIG. 49 illustrates the sphere analysis of MDAMB231 cell line in the presence of compound of Formula 81 and cisplatin.
Figure 50:
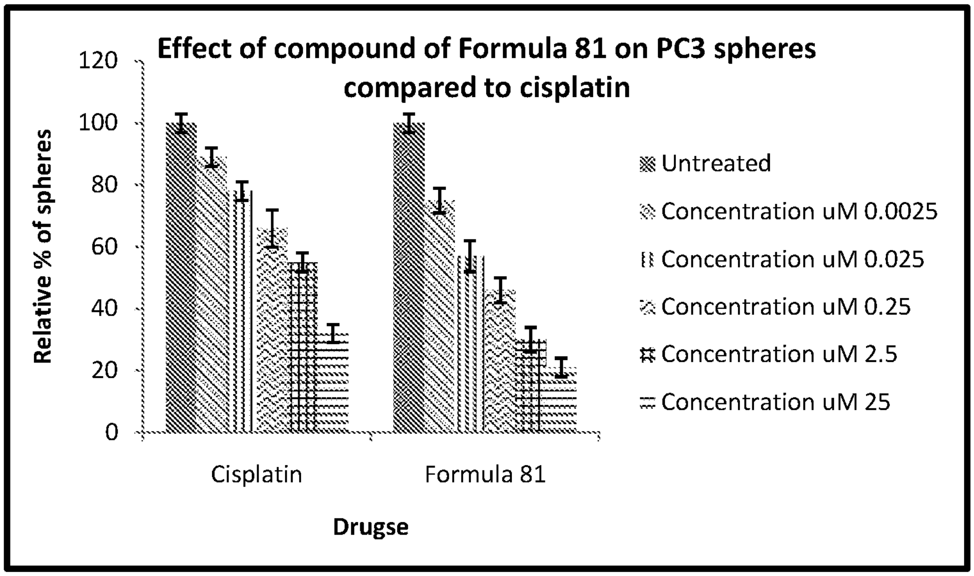
FIG. 50 illustrates the sphere analysis of PC3 cell line in the presence of compound of Formula 81 and cisplatin.

The present invention relates to compounds of Formula I for treating various conditions, particularly for inhibition of uncontrolled cell growth or proliferation or unregulated cell growth. Particularly, the compounds are effective against cancer stem cells. The structure of compound of Formula I is:

Formula I

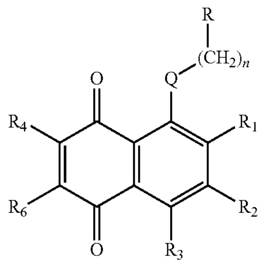

wherein, n is 1-10;

Q is O, S, —NY', wherein Y' is selected from —H, alkyl;

$R_1$, $R_2$, $R_3$ and $R_4$ each independently is selected from —H, alkoxy, alkyl, substituted or unsubstituted aromatic group, substituted or unsubstituted aromatic group with a fused ring formed by heterocycloalkyl group, $—NH_2$, $—NO_2$, $—NHCOCH_3$, —CN, —O—, halogen, $—OCF_3$, heterocycloalkyl group, $—O—(CH_2)_n$-heterocycloalkyl group;

R is selected from substituted or unsubstituted heterocycloalkyl, substituted or unsubstituted cycloalkyl, $—NR_{10}R_{11}$, $—NR_{10}R_{11}\cdot HCl$ or acid salt, $—OR_{10}R_{11}$, $—CONR_{10}R_{11}$, $—NR_{10}R_{11}CONR_{10}R_{11}$, $—NR_{10}R_{11}SOONR_{10}R_{11}$, —COOH, wherein $R_{10}$ and $R_{11}$ each independently is selected from —H, alkyl, substituted or unsubstituted aryl, heteroaryl, alkyl amine, substituted aryl amine, substituted or unsubstituted cycloalkyl group, $—CH_2—CH_2—O$-alkyl, or $R_{10}$ and $R_{11}$ together form a substituted or unsubstituted cycloalkyl or heterocycloalkyl or $R_{10}$ and Ru together form a substituted or unsubstituted cycloalkyl or heterocycloalkyl ring with —N included in the ring;

$R_{10}$ is

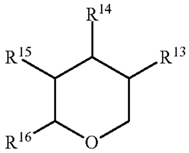

wherein, $R_{13}$ is selected from —OH, $—NH_2$, $—NHCOCH_3$, alkyl, acetyl, $C_3$-$C_8$ acyl group, X selected from F, Cl, Br;

$R_{14}$ is selected from alkoxy, —OMe, —OH, $NH_2$, $—NHCOCH_3$, alkyl, acetyl, $C_3$-$C_8$ acyl group, X selected from F, Cl, Br;

$R_{15}$ is selected from alkoxy, —OMe, —OH, —H, Br, $NH_2$, alkyl, acetyl, $C_3$-$C_8$ acyl group, X selected from F, Cl, Br;

$R_{16}$ is selected from —H, —$CH_2OH$, —OH, alkyl, alkoxy;

$R_6$ is selected from group R defined above, —H,

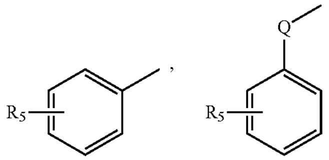

$R_5$ is located at any position and is present as a single or multiple group and is selected from —$CH_2$—O—$CH_2$, —COOH, alkyl, alkoxy, $NHCOCH_3$, —H, —OR, —NR, —X selected from F, Cl, Br, or $R_5$ forms a fused ring having —O—$CH_2$—O— group.

An embodiment of the present invention discloses compounds of Formula II represented as:

Formula II

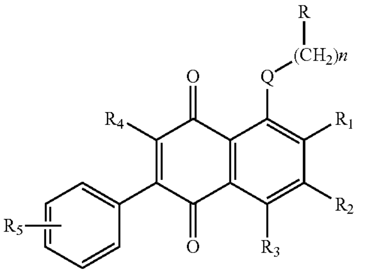

In an embodiment of the present invention, compound of Formula III is represented as:

Formula III

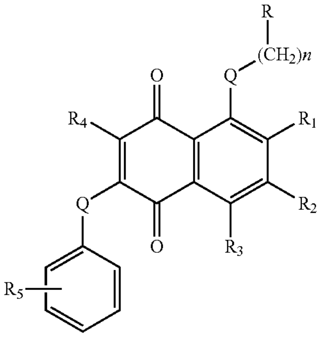

In an embodiment of the present invention, compound of Formula IV is represented as:

Formula IV

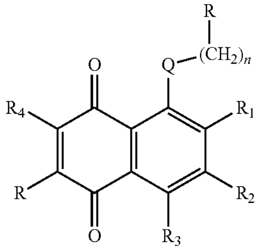

In an embodiment of the present invention, the compounds include:

$R_1$, $R_2$, $R_3$ each independently is selected from —H;

$R_4$ is selected —H, alkoxy, alkyl, substituted or unsubstituted aromatic group, —$NH_2$, —$NO_2$, —$NHCOCH_3$, —CN, —O—, halogen, —$OCF_3$,

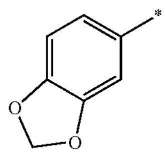

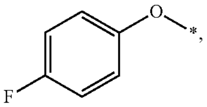

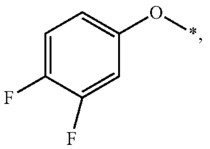

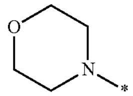

$R_6$ is selected from —H

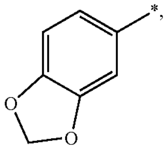

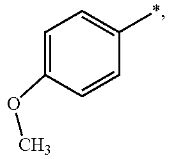

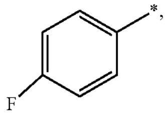

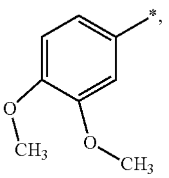

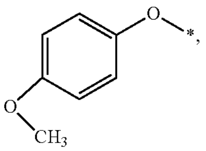

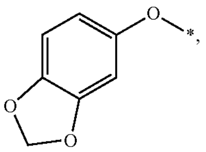

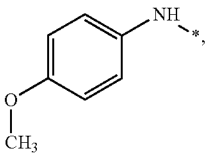

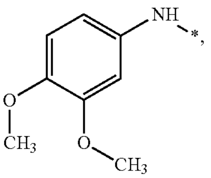

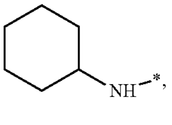

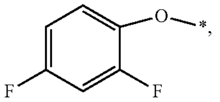

-continued

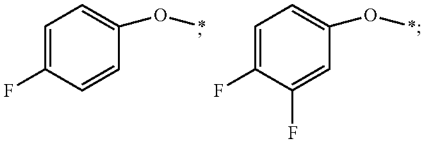

Q is selected from —O, —NH;

R is selected from —COOH,

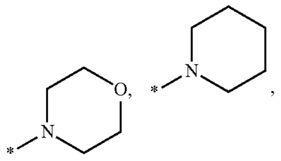

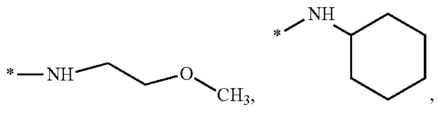

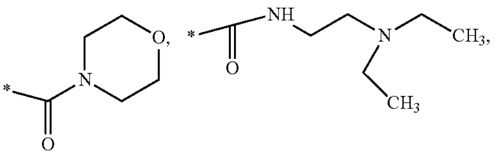

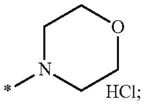

n is 1-6; and

* represents point of attachment.

In an embodiment of the present invention, the compounds comprise of the following: the group -Q-$(CH_2)_n$—R is absent, $R_1$, $R_2$, $R_3$ each independently is selected from —H, $R_6$ is —H, $R_4$ is selected from

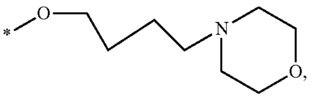 [SMILES: *OCCCCN1CCOCC1]

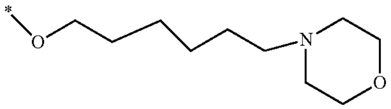 [SMILES: *OCCCCCCN1CCOCC1]

* represents point of attachment.

The compounds encompassed by Formulae I to IV are as follows:

Formula 1

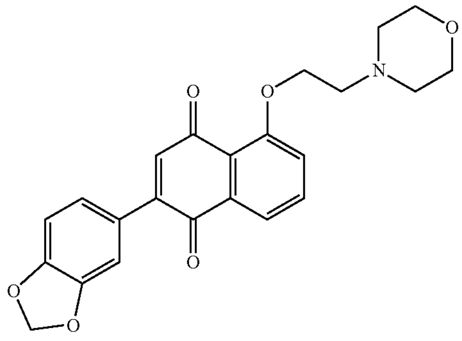

Formula 2

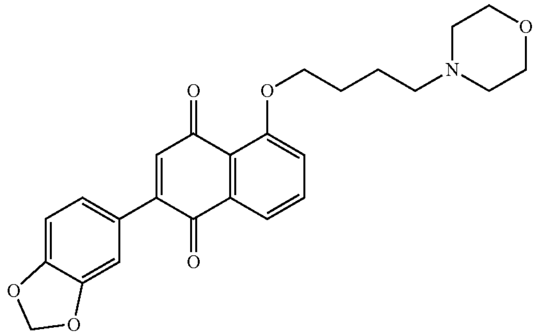

Formula 4

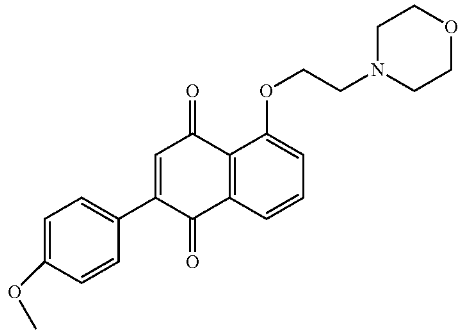

Formula 5

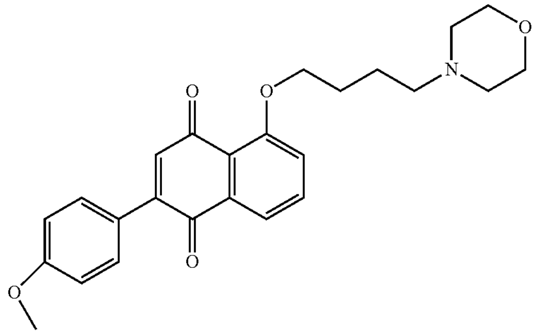

Formula 6
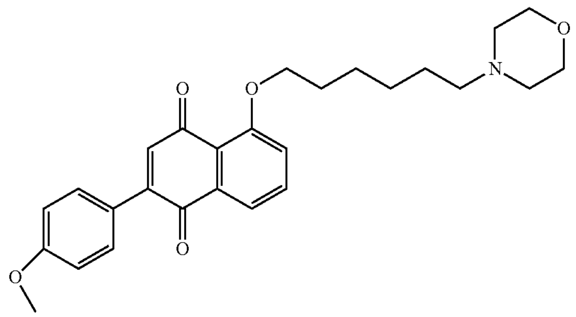
Formula 7
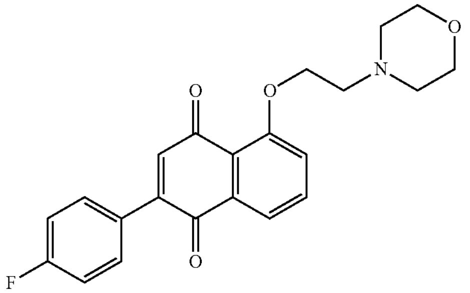
Formula 8
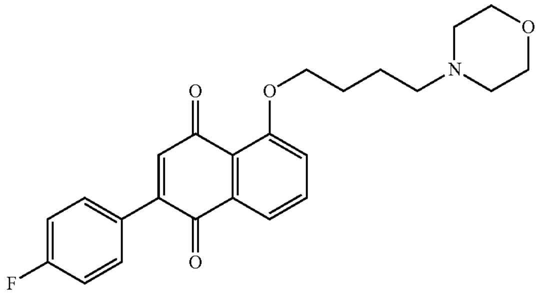
Formula 9
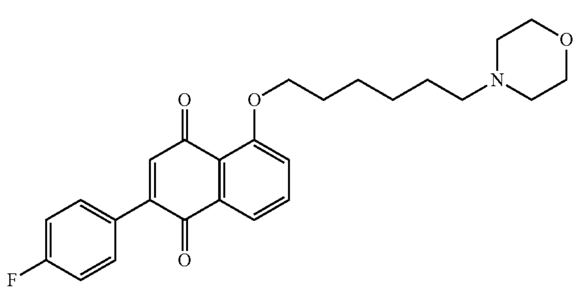
Formula 10
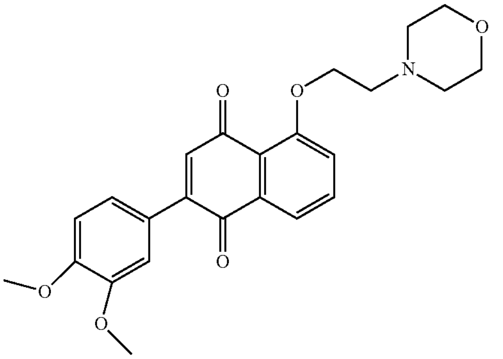
Formula 11
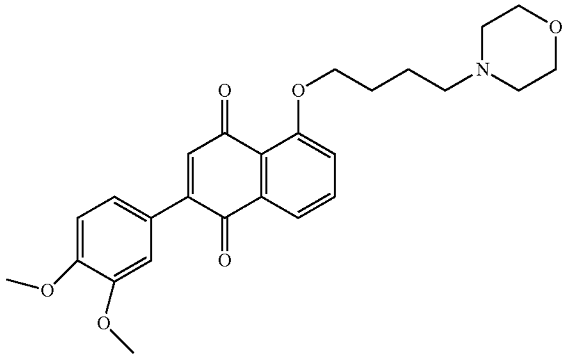
Formula 12
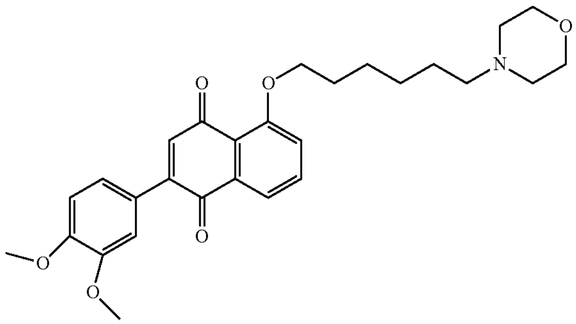
Formula 17
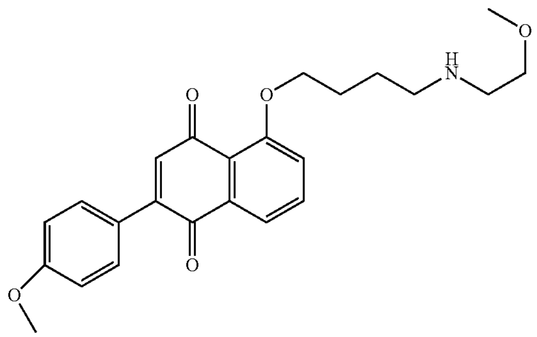
Formula 20
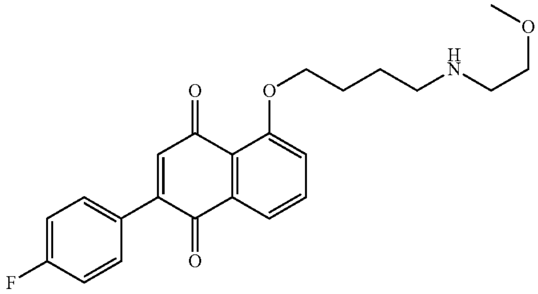

-continued
Formula 23
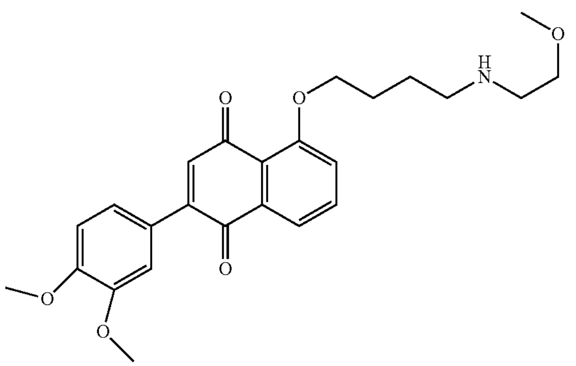
Formula 32
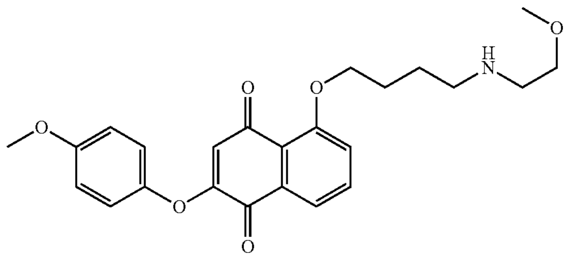
Formula 33
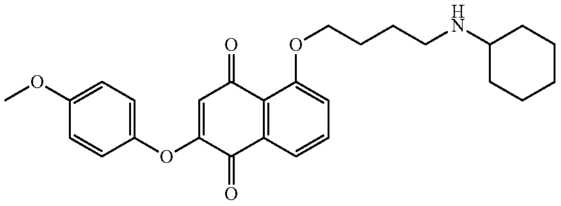
Formula 35
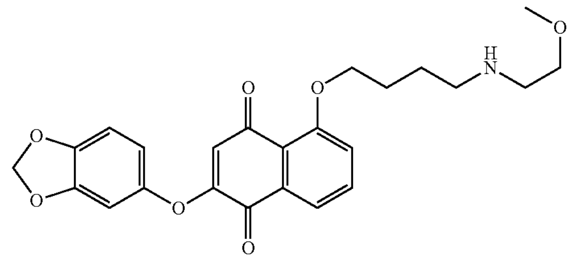
Formula 36
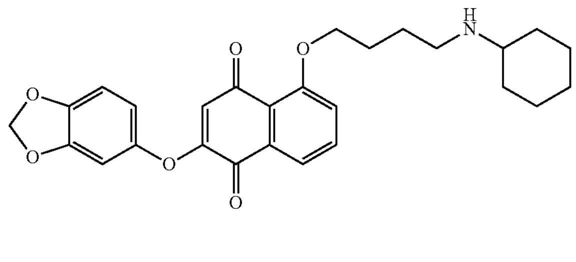
-continued
Formula 37
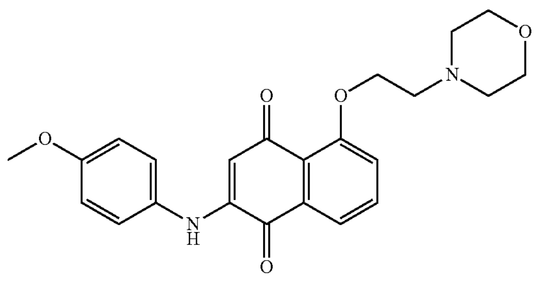
Formula 40
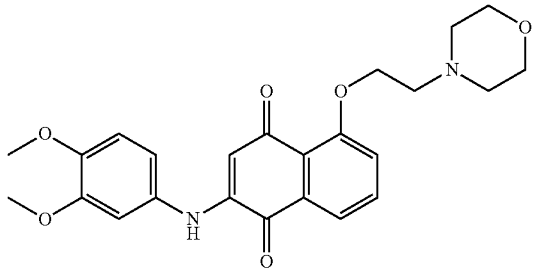
Formula 41
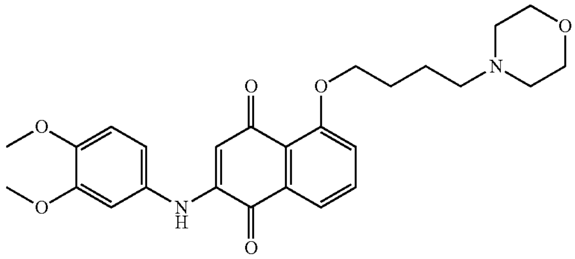
Formula 43
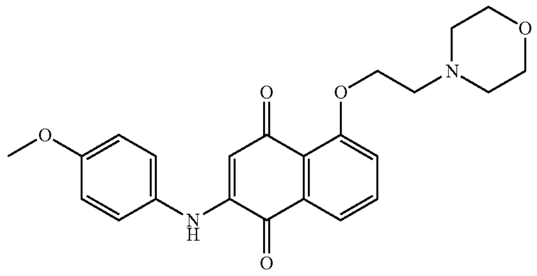
Formula 44
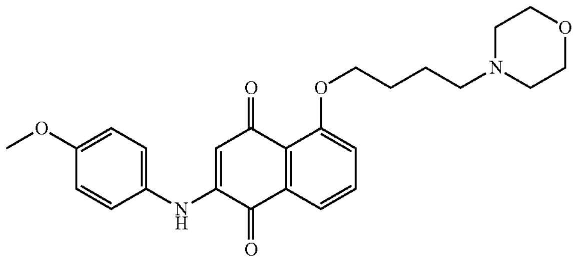

-continued
Formula 46
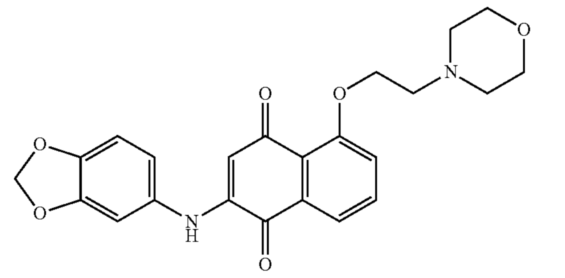
Formula 47
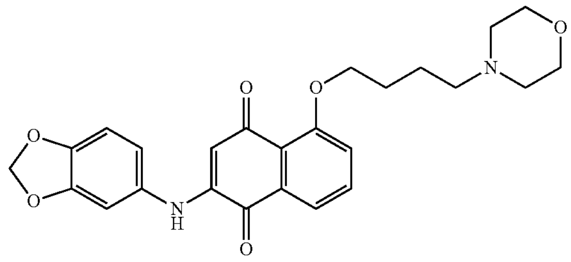
Formula 52
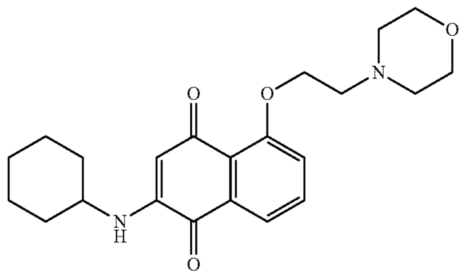
Formula 67
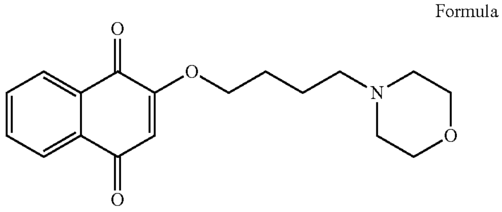
Formula 68
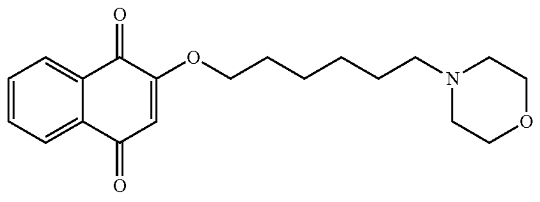
-continued
Formula 69
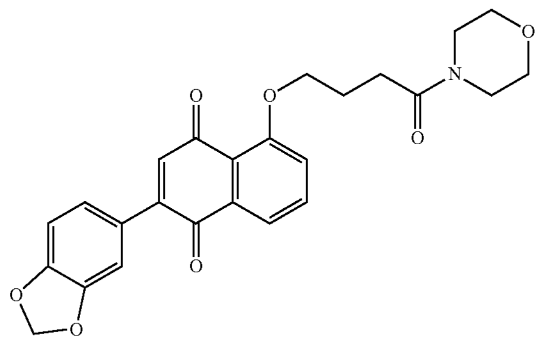
Formula 70
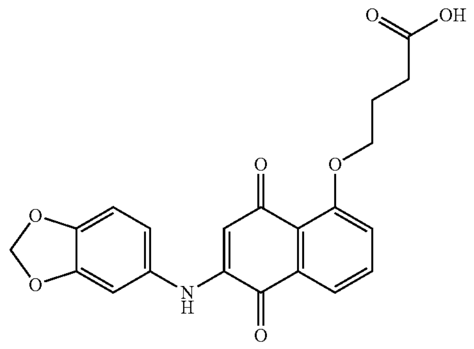
Formula 71
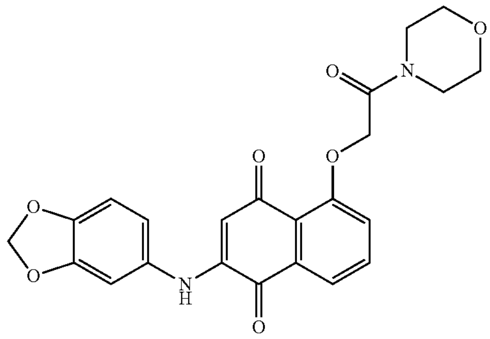
Formula 72
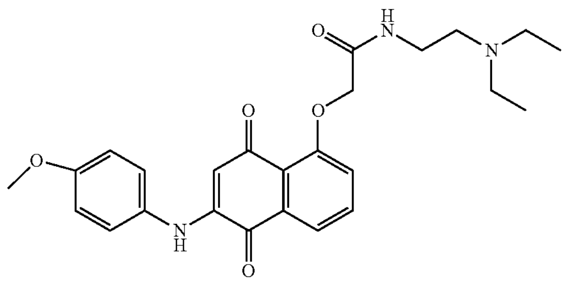

-continued
Formula 73
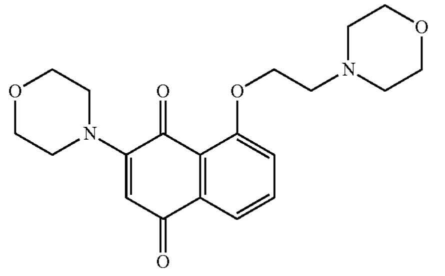
Formula 74
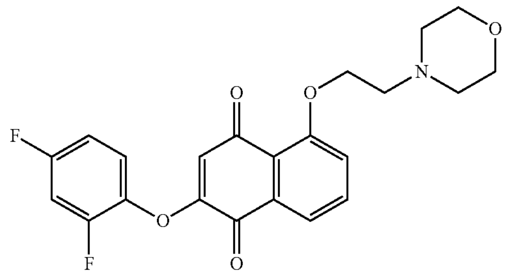
Formula 75
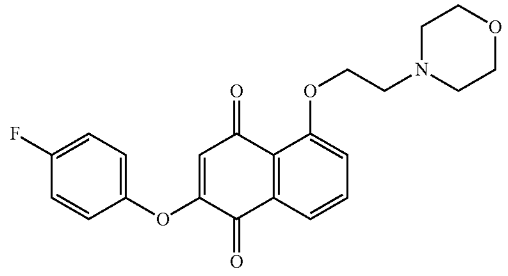
Formula 76
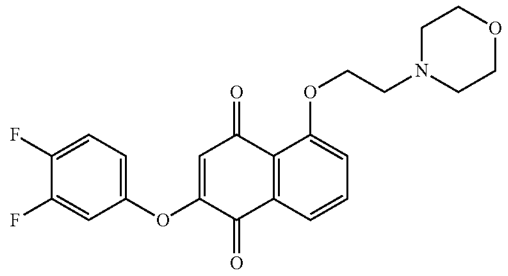
Formula 77
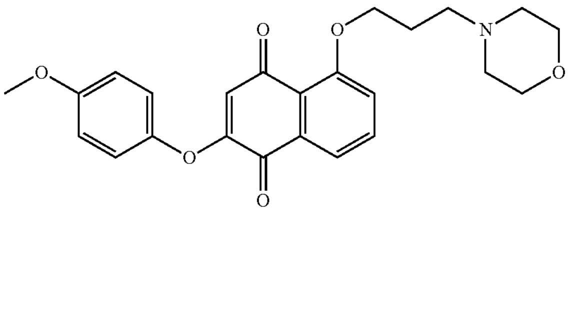
-continued
Formula 78
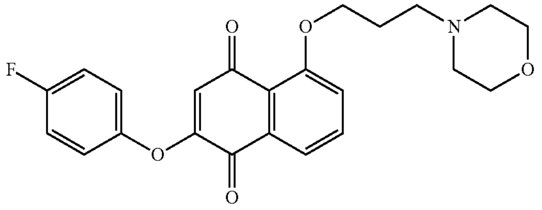
Formula 79
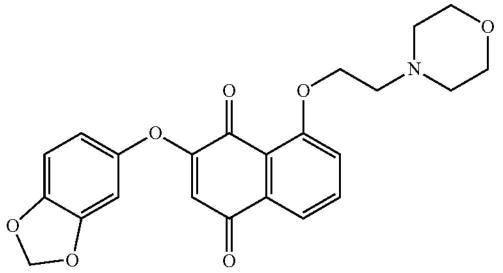
Formula 80
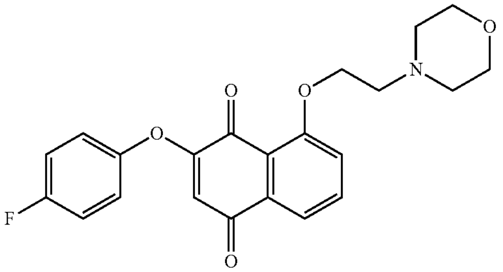
Formula 81
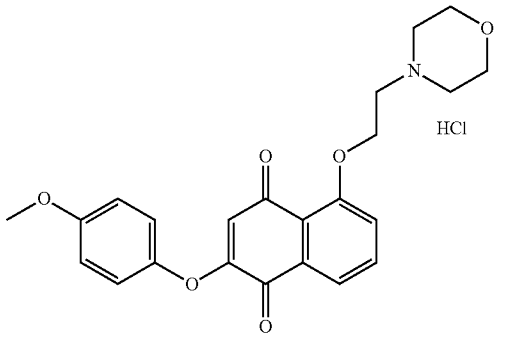
Formula 82
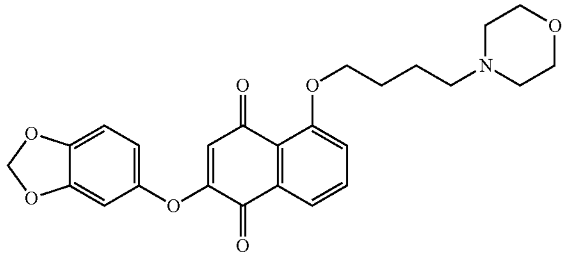

-continued

Formula 83

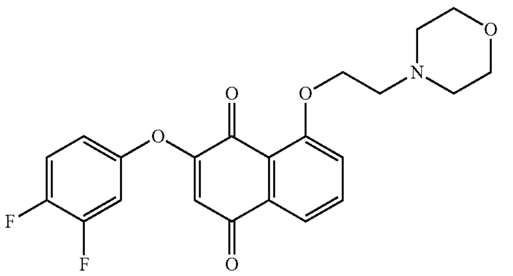

Formula 84

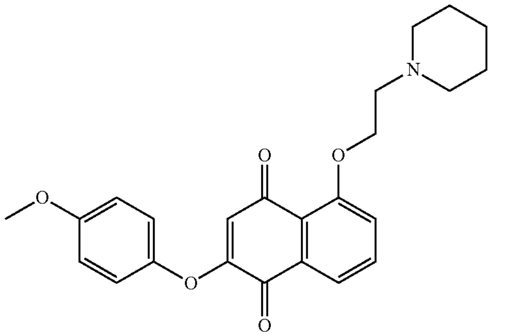

Formula 85

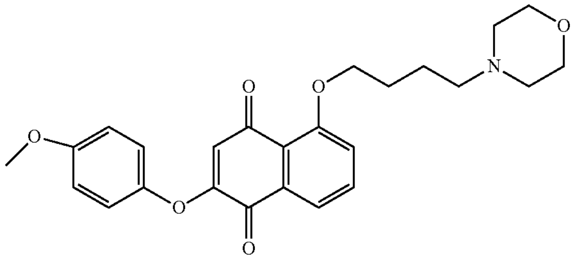

The present invention also encompasses a pharmaceutical composition comprising compound of Formula I to IV or any of the above compounds, at least one pharmaceutically acceptable excipient and optionally at least one active agent.

The active agent is selected from, but not limited to, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™ Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™ Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™ Elspar®, Emcyt®, Epirubicin, Epoetin Alfa, Erbitux, Erlotinib, *Erwinia* L-asparaginase, Estramustine, Ethyol, Etophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™ Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

The pharmaceutically acceptable excipient includes carrier, adjuvant, vehicle or mixtures thereof.

glands, muscle, heart, and stomach cancer, particularly the compounds are used for the treatment of breast and prostate cancer.

The compounds were found to have lower activity on normal cells (lymphocytes) compared to activity on cancer cells.

The compounds were found to have wound healing effect in breast and prostate cancers.

The compounds were found to inhibit Aldehyde dehydrogenase (ALDH)—a Cancer Stem Cell (CSC) marker.

In an embodiment, the compounds can be used in the treatment of malaria, dengue.

The process of synthesis of the compounds are described below.

EXAMPLES

The examples illustrated herein below define the invention but are not limiting thereof.

Scheme 1

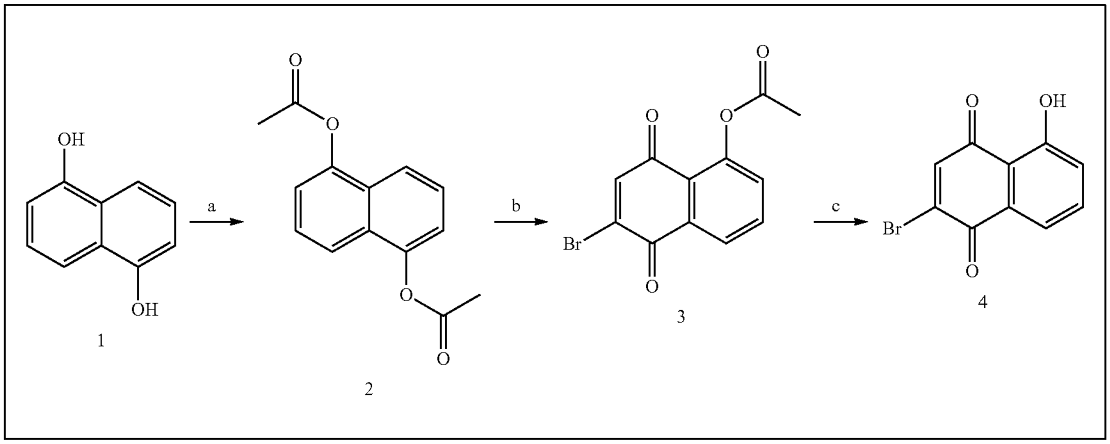

The compounds of the present invention are used in the treatment or inhibition of uncontrolled cell growth such as cancer. The compounds effectively target cancer cells including cancer stem cells.

The present invention also relates to a method of treatment or inhibition of uncontrolled cell growth such as cancer. The compounds have been found to target cancer cells including cancer stem cells. The method comprises administering an effective amount of one or more of compound of Formula I to IV to a patient.

The invention also relates to a method of treatment or inhibition of uncontrolled cell growth such as cancer by administering an effective amount of a pharmaceutical composition comprising one or more of compound of Formula I to IV or any of the above compounds to a patient.

The compounds of the present invention can also be provided along with standard therapies available for the treatment of cancer.

The compounds of the present invention are used for the treatment or inhibition of at least one of breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous Reagents and conditions: a. Acetic anhydride, Pyridine, RT, 12 hrs, b. NBS, AcOH, $H_2O$, 65° C., 2 hrs, c. 5N $H_2SO_4$, retarder, 90° C., 2 hrs

Synthesis of Compound 2 (1,5 Diacetate Naphthalene)

In a clean and dry 3 necked RB was charged with 1,5 dihydroxy naphthalene (20 g, 0.1249 mol) in pyridine (100 ml) and reaction mixture was stirred for 15 min at room temperature (RT). Afterwards, temperature dropped into 0° C. Weighed quantity of Acetic Anhydride (57.28 gm, 0.5620 mol) added dropwise into RM at 0° C. and reaction mixture was stirred for 12 hr and monitored using TLC. Reaction Mixture was slowly poured into ice chilled water (1000 ml) and stirred. Reaction mixture was stirred using overhead stirrer by 45 min. Reaction Mixture was filtered and Precipitate was dissolved in MDC (1000 ml). Organic layer was washed with Copper sulphate solution (250 ml*5 times) and Brine solution (200 ml*3 times). Reaction mixture was concentrated under reduced pressure. The obtained crude comp. was purified by simple filtration column chromatography. (Hexane:Ethyl acetate—40:60). Pure comp.=24 gm. % Yield=79%.

$^1$H NMR ($CDCl_3$, 400 MHz): δ=7.77 (dd, J=8.5 Hz, 2H), 7.49 (t, J=8.0 Hz, 2H), 7.28 (d, J=7.5 Hz, 2H), 2.44 (s, 6H).

Synthesis of Compound 3 (2-bromo-1,4-dihydro-1,4-dioxonaphthalen-5-yl acetate)

In a clean and dry 3 necked RB was charged with NBS (58.07 gm, 0.3277 mol) in (500 ml) water and (500 ml) Acetic Acid and reaction mixture for 15 min at 45° C. Compound 1 (20 gm, 0.0819 mol) dissolved in (500 ml) of Acetic Acid and warmed at 45° C. Comp 1 solution added dropwise into reaction mixture of NBS at 45° C. in 30 min. This Reaction mixture stirred for 40 min at 45° C. Temperature increases up to 65° C. and stirred for 1 hr. Reaction mixture was monitored by TLC. After completion, reaction mixture was cooled to RT and reaction mixture was poured in water (1500 ml) and extracted with MDC (250 ml*6 times). Organic layer was washed with saturated sodium Bicarbonate and Brine solution (200 ml*3 times). The combined organic layer was dried over vacuum and concentrated under reduced pressure. Crude comp.=33 gm.

$^1$H NMR ($CDCl_3$, 400 MHz): δ=8.15 (dd, J=1.2, 8.0 Hz, 1H), 7.77 (t, J=8.0 Hz, 1H), 7.42 (dd, J=1.2, 8.0 Hz, 1H), 7.38 (s, 1H), 2.44 (s, 3H).

Synthesis of Compound 4 (2-bromo-5-hydroxynaphthalene-1,4-dione)

In a clean and dry 3 necked RB was charged with Compound 3 dissolved in retarder (715 ml) at 45° C. for 15 min and stirred. Afterwards, 5N Sulphuric Acid (396 ml) slowly added into it. Reaction mixture was refluxed for 2 hr at 90° C. Reaction was monitored by TLC. Reaction mass was evaporated on rotaevapourator up to dry. Reaction mixture was poured in 1000 ml of water and extracted by MDC (250 ml*6 times). Organic layer was washed with brine solution (200 ml*3 times) and dried over sodium sulphate. Organic layer was concentrated under reduced pressure. The obtained crude comp. was purified by simple filtration column chromatography, Hexane:Ethyl acetate—80:20. Pure comp. 9.9 gm. Yield 35. %.

$^1$H NMR ($CDCl_3$, 400 MHz): δ=11.81 (s, 1H), 7.73 (d, J=8.2 Hz, 1H), 7.67 (t, J=8.2 Hz, 1H), 7.32 (d, J=8.2 Hz, 1H), 7.20 (s, 1H).

Synthesis of Compound 5a (5-hydroxy-2-(4-methoxyphenyl)naphthalene-1,4-dione)

To a solution of compound 4 (1.0 g, 39.2 mmol) and 4-Methoxy phenylboronic acid (0.72 g, 47.4 mmol) in THF (108 ml) and Water (12 ml). $Na_2CO_3$ (0.82 g, 78.4 mmol) was added in reaction mixture. $Pd(PPh_3)_4$ (0.226 g, 1.97 mmol) was added under nitrogen atmosphere and stirred for 30 min at RT. The reaction mixture was stirred at RT for 16 hrs, and monitored using TLC. After completion, reaction mixture was cooled to RT and reaction mixture was poured in water (200 ml) and extracted with ethyl acetate (100 ml*3 times). Organic layer was washed with water (100 ml). The combined organic layer was dried over anhydrous sodium sulfate and concentrated under reduced pressure. The obtained crude comp. was purified by column chromatography (Hexane:Ethyl acetate—90:10). Pure comp.=0.45 gm. % Yield=45%.

$^1$H NMR ($CDCl_3$, 400 MHz): δ=12.07 (s, 1H), 7.71 (d, J=8.2 Hz, 1H), 7.69 (d, J=8.2 Hz, 1H), 7.66 (d, J=8.0 Hz, 1H), 7.59 (d, J=2.4 Hz, 1H), 7.29 (d, J=1.2 Hz, 1H), 7.0 (m, 3H), 3.87 (s, 3H).

Synthesis of Compound 5b (2-(4-fluorophenyl)-5-hydroxynaphthalene-1,4-dione)

To a solution of compound 4 (1.0 g, 39.2 mmol) and 4-Fluoro phenylboronic acid (0.66 g, 47.4 mmol) in THF (108 ml) and Water (12 ml). $Na_2CO_3$ (0.82 g, 78.4 mmol) was added in reaction mixture. $Pd(PPh_3)_4$ (0.226 g, 1.97 mmol) was added under nitrogen atmosphere and stirred for 30 min at RT. The reaction mixture was stirred at RT for 16 hrs, and monitored using TLC. After completion, reaction mixture was cooled to RT and reaction mixture was poured in water (200 ml) and extracted with ethyl acetate (100 ml*3 times). Organic layer was washed with water (100 ml). The combined organic layer was dried over anhydrous sodium sulfate and concentrated under reduced pressure. The obtained crude comp. was purified by column chromatography (Hexane:Ethyl acetate—90:10). Pure comp.=0.40 gm. % Yield=41%.

Scheme 2

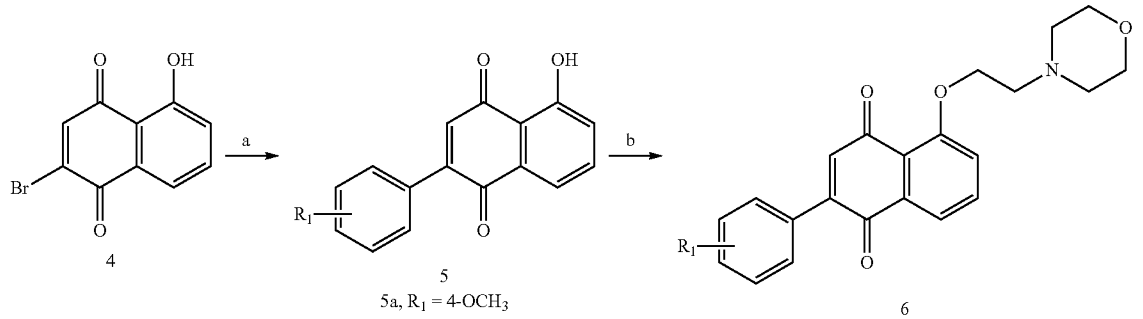

4

5

5a, $R_1$ = 4-$OCH_3$
5b, $R_1$ = 4-F
5c, $R_1$ = 3,4 Methylene dioxy

6

Formula 7, $R_1$ = 4-F
Formula 1, $R_1$ = 3,4 Methylene dioxy

Reagents and conditions: a. Substituted phenyl boronic acid, $Pd(PPh_3)_4$, $Na_2CO_3$, THF, Water, RT, 12 hrs, b. 4-(2-chloroethyl)morpholine hydrochloride, $K_2CO_3$, DMF, 100° C., 3 hrs $^1H$ NMR ($CDCl_3$, 400 MHz): δ=11.99 (s, 1H), 7.72 (d, J=6.0 Hz, 1H), 7.68 (d, J=6.0 Hz, 1H), 7.60 (m, 2H), 7.31 (d, J=6.8 Hz, 1H), 7.19 (m, 2H), 7.02 (s, 1H).

Synthesis of Compound 5c (2-(benzo[d][1,3]dioxol-6-yl)-5-hydroxynaphthalene-1,4-dione)

To a solution of compound 4 (1.0 g, 39.2 mmol) and 3,4(methylenedioxy) phenylboronic acid (0.65 g, 39.2 mmol) in THF (90 ml) and Water (10 ml). $Na_2CO_3$ (0.83 g, 78.4 mmol) was added in reaction mixture. $Pd(PPh_3)_4$ (0.226 g, 1.96 mmol) was added under nitrogen atmosphere and stirred for 30 min at RT. The reaction mixture was stirred at RT for 16 hrs, and monitored using TLC. After completion, reaction mixture was cooled to RT and reaction mixture was poured in water (200 ml) and extracted with ethyl acetate (100 ml*3 times). Organic layer was washed with water (100 ml). The combined organic layer was dried over anhydrous sodium sulfate and concentrated under reduced pressure. The obtained crude comp. was purified by column chromatography (Hexane:Ethyl acetate—90:10). Pure comp.=0.72 gm. % Yield=64%.

$^1H$ NMR ($CDCl_3$, 400 MHz): δ=12.03 (s, 1H), 7.71 (d, J=8.2 Hz, 2H), 7.69 (d, J=8.2 Hz, 1H), 7.30 (d, J=8.2 Hz, 1H), 7.14 (m, 2H), 6.98 (s, 1H), 6.91 (d, J=8.0 Hz, 1H), 6.04 (s, 2H).

Synthesis of Compound of Formula 7 (5-(2-morpholinoethoxy)-2-(4-fluorophenyl) naphthalene-1,4-dione)

Two necked RBF (100 mL) was charged with compound 5b (0.25 gm, 9.36 mmol) and DMF (20 ml). $K_2CO_3$ (0.26 g, 18.7 mmol) and KI (0.015 gm, 0.93 mmol) was added in reaction mixture and stirred at RT for 15 min. 4-(2-chloroethyl)morpholine hydrochloride (0.209 gm, 11.23 mmol) was added in reaction mixture. Reaction mixture was heated at 100° C. for 4 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=206 mg. % Yield=58%.

$^1H$ NMR ($CDCl_3$, 400 MHz): δ=7.84 (d, J=6.0 Hz, 1H), 7.71 (d, J=6.0 Hz, 1H), 7.58 (m, 2H), 7.33 (d, J=6.8 Hz, 1H), 7.17 (m, 2H), 6.93 (s, 1H), 4.31 (t, J=4.4 Hz, 2H), 3.75 (m, 4H), 2.98 (t, J=4.8 Hz, 2H), 2.72 (m, 4H).

Synthesis of Compound of Formula 1 (5-(2-morpholinoethoxy)-2-(benzo[d][1,3]dioxol-6-yl)naphthalene-1,4-dione)

Two necked RBF (100 mL) was charged with compound 5c (0.2 gm, 8.40 mmol) and DMF (20 ml). $K_2CO_3$ (0.23 g, 16.8 mmol) and KI (0.013 gm, 0.84 mmol) was added in reaction mixture and stirred at RT for 15 min. 4-(2-chloroethyl)morpholine hydrochloride (0.187 gm, 10.08 mmol) was added in reaction mixture. Reaction mixture was heated at 100° C. for 4 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=40 mg. % Yield=16%.

$^1H$ NMR ($CDCl_3$, 400 MHz): δ=7.83 (d, J=8.0 Hz, 1H), 7.69 (d, J=8.2 Hz, 1H), 7.31 (d, J=8.2 Hz, 1H), 7.11 (m, 2H), 6.90 (m, 2H), 6.02 (s, 2H), 4.32 (t, J=4.4 Hz, 2H), 3.78 (m, 4H), 3.04 (t, J=4.8 Hz, 2H), 2.82 (m, 4H).

Scheme 3

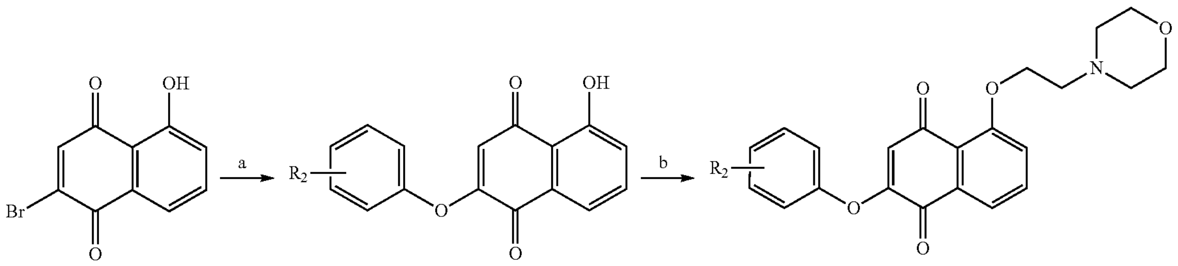

4

7

7a, $R_2$ = 4-$OCH_3$

7b, $R_2$ = 4-F

7c, $R_2$ = 3,4 Methylene dioxy

8

Formula 43, $R_2$ = 4 -$OCH_3$

Formula 75, $R_2$ = 4-F

Formula 46, $R_2$ = 3,4 Methylene dioxy

Reagents and conditions: a. $K_2CO_3$, DMF, RT, 4 hrs, b. 4-(2-chloroethyl)morpholine hydrochloride, $K_2CO_3$, DMF, 100° C., 4 hrs

Synthesis of Compound 7a (2-(4-methoxyphenoxy)-5-hydroxynaphthalene-1,4-dione)

Two necked RBF (250 mL) was charged with 4-Methoxy phenol (0.972 gm, 78.4 mmol) and DMF (50 ml). $K_2CO_3$ (1.08 g, 78.4 mmol) was added in reaction mixture and stirred at RT for 15 min. Compound 4 (2.0 gm, 78.4 mmol) was added in reaction mixture. Reaction mixture was stirred at RT for 3 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—95:5). Pure comp.=0.538 gm. % Yield=24%.

$^1$H NMR ($CDCl_3$, 400 MHz): δ=12.07 (s, 1H), 7.86 (d, J=8.0 Hz, 1H), 7.80 (d, J=0.8 Hz, 1H), 7.65 (d, J=0.8 Hz, 1H), 7.20 (d, J=9.2 Hz, 2H), 7.07 (d, J=9.2 Hz, 2H), 5.60 (s, 1H).

Synthesis of Compound 7b (2-(4-fluorophenoxy)-5-hydroxynaphthalene-1,4-dione)

Two necked RBF (100 mL) was charged with 4-Fluoro phenol (0.443 gm, 39.5 mmol) and DMF (50 ml). $K_2CO_3$ (0.54 g, 39.5 mmol) was added in reaction mixture and stirred at RT for 15 min. Compound 4 (1.0 gm, 39.5 mmol) was added in reaction mixture. Reaction mixture was stirred at RT for 3 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—95:5). Pure comp.=1.05 gm. % Yield=78%.

$^1$H NMR ($CDCl_3$, 400 MHz): δ=12.07 (s, 1H), 7.74 (d, J=1.2 Hz, 1H), 7.62 (m, 1H), 7.31 (dd, J=1.2 Hz & 7.6 Hz, 1H), 7.17 (m, 4H), 5.87 (s, 1H).

Synthesis of Compound 7c (2-(benzo[d][1,3]dioxol-5-yloxy)-5-hydroxynaphthalene-1,4-dione)

Two necked RBF (100 mL) was charged with sesamol (1.08 gm, 78.4 mmol) and DMF (50 ml). $K_2CO_3$ (0.54 g, 78.4 mmol) was added in reaction mixture and stirred at RT for 15 min. Compound 4 (2.0 gm, 78.4 mmol) was added in reaction mixture. Reaction mixture was stirred at RT for 4 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—95:5). Pure comp.=0.676 gm. % Yield=25%.

$^1$H NMR ($CDCl_3$, 400 MHz): δ=12.11 (s, 1H), 7.74 (d, J=0.8 Hz, 1H), 7.72 (dd, J=1.2 Hz, 8.4 Hz, 1H), 7.30 (d, J=0.8 Hz, 1H), 6.85 (d, J=8 Hz, 1H), 6.62 (dd, J=2.4 Hz, 7.6 Hz, 1H), 6.58 (d, J=2.4 Hz, 1H), 6.05 (s, 2H).

Synthesis of Compound Formula 43 (5-(2-morpholinoethoxy)-2-(4-methoxyphenoxy) naphthalene-1,4-dione)

Two necked RBF (100 mL) was charged with compound 7a (0.32 gm, 10.94 mmol) and DMF (20 ml). $K_2CO_3$ (0.30 g, 21.9 mmol) was added in reaction mixture and stirred at RT for 15 min. 4-(2-chloroethyl)morpholine hydrochloride (0.41 gm, 21.9 mmol) was added in reaction mixture. Reaction mixture was heated at 100° C. for 6 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=69 mg. % Yield=21%.

$^1$H NMR ($CDCl_3$, 400 MHz): δ=7.88 (d, J=6.8 Hz, 1H), 7.68 (d, J=8.4 Hz, 1H), 7.34 (d, J=8.4 Hz, 1H), 7.17 (m, 4H), 5.82 (s, 1H), 4.27 (t, J=5.6 Hz, 2H), 3.83 (s, 3H), 3.72 (m, 4H), 2.92 (t, J=5.6 Hz, 2H), 2.68 (m, 4H).

Synthesis of Compound Formula 75 (5-(2-morpholinoethoxy)-2-(4-fluorophenoxy) naphthalene-1,4-dione)

Two necked RBF (100 mL) was charged with compound 7b (0.32 gm, 10.94 mmol) and DMF (20 ml). $K_2CO_3$ (0.30 g, 21.9 mmol) was added in reaction mixture and stirred at RT for 15 min. 4-(2-chloroethyl) morpholine hydrochloride (0.41 gm, 21.9 mmol) was added in reaction mixture. Reaction mixture was heated at 100° C. for 6 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=69 mg. % Yield=21%.

$^1$H NMR ($CDCl_3$, 400 MHz): δ=7.78 (d, J=1.2 Hz, 1H), 7.62 (m, 1H), 7.31 (dd, J=1.2 Hz & 7.6 Hz, 1H), 7.17 (m, 4H), 5.82 (s, 1H), 4.27 (t, J=5.6 Hz, 2H), 3.72 (m, 4H), 2.92 (t, J=5.6 Hz, 2H), 2.68 (m, 4H).

Synthesis of Compound Formula 46 (5-(2-morpholinoethoxy)-2-(benzo[d][1,3]dioxol-5-yloxy) naphthalene-1,4-dione)

Two necked RBF (100 mL) was charged with compound 7c (0.5 gm, 17.66 mmol) and DMF (20 ml). $K_2CO_3$ (0.49 g, 35.3 mmol) was added in reaction mixture and stirred at RT for 15 min. 4-(2-chloroethyl)morpholine hydrochloride (0.395 gm, 21.2 mmol) was added in reaction mixture. Reaction mixture was heated at 100° C. for 2 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=294 mg. % Yield=42%.

$^1$H NMR ($CDCl_3$, 400 MHz): δ=7.74 (d, J=0.8 Hz, 1H), 7.72 (dd, J=1.2 Hz, 8.4 Hz, 1H), 7.30 (d, J=0.8 Hz, 1H), 6.85 (d, J=8 Hz, 1H), 6.62 (dd, J=2.4 Hz, 7.6 Hz, 1H), 6.58 (d, J=2.4 Hz, 1H), 6.05 (s, 2H), 5.91 (s, 1H), 4.27 (t, J=5.6 Hz, 2H), 3.72 (m, 4H), 2.92 (t, J=5.6 Hz, 2H), 2.68 (m, 4H).

Scheme 4

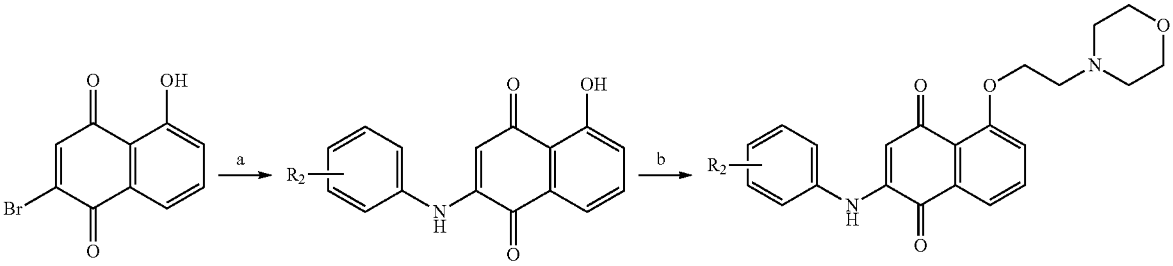

4

9

9a, $R_3$ = 4-$OCH_3$

9b, $R_3$ = 3-$OCH_3$, 4-$OCH_3$

10

Formula 37, $R_3$ = 4 -$OCH_3$

Formula 40, $R_3$ = 3-$OCH_3$, 4-$OCH_3$

Reagents and conditions: a. $K_2CO_3$, DMF, RT, 4 hrs, b. 4-(2-chloroethyl)morpholine hydrochloride, $K_2CO_3$, DMF, 100° C., 4 hrs Synthesis of Compound 9a (2-(4-methoxyphenylamino)-5-hydroxynaphthalene-1,4-dione)

Two necked RBF (100 mL) was charged with 4-Methoxy aniline (0.145 gm, 11.7 mmol) and DMF (20 ml). $K_2CO_3$ (0.217 g, 15.6 mmol) was added in reaction mixture and stirred at RT for 15 min. Compound 4 (0.2 gm, 7.84 mmol) was added in reaction mixture. Reaction mixture was stirred at RT for 3 hrs. Reaction was monitored with TLC. After completion, reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—70:30). Pure comp.=0.078 gm. % Yield=34%.

$^1$H NMR ($CDCl_3$, 400 MHz): δ=12.93 (s, 1H), 7.67 (d, J=0.8 Hz, 1H), 7.65 (m, 1H), 7.59 (d, J=8 Hz, 1H), 7.28 (d, J=8.8 Hz, 2H), 6.97 (d, J=8.8 Hz, 2H), 6.11 (s, 1H), 3.84 (s, 3H).

Synthesis of Compound 9b (2-(3,4-dimethoxyphenylamino)-5-hydroxynaphthalene-1,4-dione)

Two necked RBF (250 mL) was charged with 3, 4-Dimethoxy aniline (0.72 gm, 47 mmol) and DMF (50 ml). $K_2CO_3$ (1.08 g, 78.2 mmol) was added in reaction mixture and stirred at RT for 15 min. Compound 4 (1.0 gm, 39.2 mmol) was added in reaction mixture. Reaction mixture was stirred at RT for 12 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—80:20). Pure comp.=0.53 gm. % Yield=41%.

$^1$H NMR ($CDCl_3$, 400 MHz): δ=12.92 (s, 1H), 7.67 (d, J=0.8 Hz, 1H), 7.65 (m, 1H), 7.59 (d, J=8 Hz, 1H), 7.28 (d, J=0.8 Hz, 1H), 6.91 (d, J=8.8 Hz, 1H), 6.76 (d, J=2.4 Hz, 1H), 6.11 (s, 1H), 3.91 (s, 6H).

Synthesis of Compound Formula 37 (5-(2-morpholinoethoxy)-2-(4-methoxyphenylamino) naphthalene-1,4-dione Two necked RBF (100 mL) was charged with compound 9a (0.3 gm, 11.76 mmol) and DMF (30 ml). $K_2CO_3$ (0.324 g, 23.5 mmol) was added in reaction mixture and stirred at RT for 15 min. 4-(2-chloroethyl)morpholine hydrochloride (0.437 gm, 23.5 mmol) was added in reaction mixture. Reaction mixture was heated at 100° C. for 4 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=98 mg. % Yield=21%.

$^1$H NMR ($CDCl_3$, 400 MHz): δ=12.74 (s, 1H), 7.45 (m, 2H), 7.21 (m, 3H), 7.05 (m, 2H), 5.74 (s, 1H), 4.06 (t, J=6.8 Hz, 2H), 3.91 (s, 3H), 3.64 (m, 4H), 2.69 (m, 2H), 2.49 (m, 4H).

Synthesis of Compound Formula 40 (5-(2-morpholinoethoxy)-2-(3,4-dimethoxyphenylamino) naphthalene-1,4-dione Two necked RBF (100 mL) was charged with compound 9b (0.3 gm, 9.14 mmol) and DMF (30 ml). $K_2CO_3$ (0.251 g, 18.3 mmol) was added in reaction mixture and stirred at RT for 15 min. 4-(2-chloroethyl)morpholine hydrochloride (0.34 gm, 18.2 mmol) was added in reaction mixture. Reaction mixture was heated at 100° C. for 4 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=35 mg. % Yield=8%.

$^1$H NMR ($CDCl_3$, 400 MHz): δ=12.74 (s, 1H), 7.48 (m, 2H), 7.21 (d, J=2 Hz, 1H), 6.89 (d, J=8.4 Hz, 1H), 6.73 (m, 2H), 5.52 (s, 1H), 4.06 (d, J=6.8 Hz, 2H), 3.91 (s, 6H), 3.62 (m, 4H), 2.68 (d, J=7.2 Hz, 2H), 2.48 (m, 4H).

Scheme 5

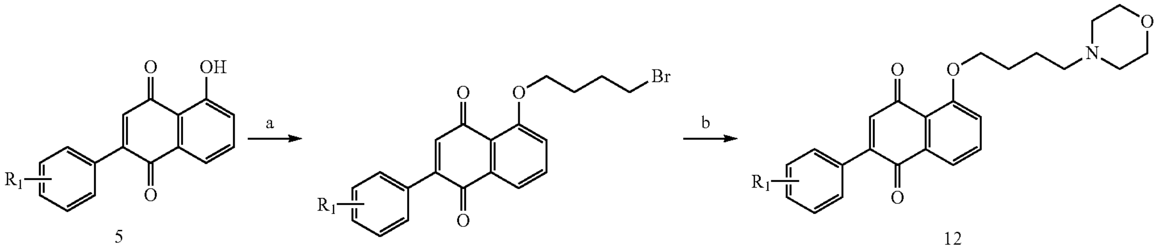

5
5c, $R_1$ = 3,4 Methylene dioxy 11
11c, $R_1$ = 3,4 Methylene dioxy

12
Formula 2, $R_1$ = 3,4 Methylene dioxy

Reagents and conditions: a. Dibromobutane, TBAB, NaOH, $H_2O$, 60° C., 4 hrs b. Morpholine, $K_2CO_3$, DMF, RT 12 hrs

Synthesis of Compound 11c (5-(4-bromobutoxy)-2-(benzo[d][1,3]dioxol-6-yl)naphthalene-1,4-dione)

Dibromobutane (2.2 gm, 103.5 mmol)) was added drop-wise to a solution of Compound 5c (0.35 gm, 10.35 mmol), NaOH (0.082 gm, 20.7 mmol), TBAB (33 mg, 1.35 mmol) and water (30 ml). Reaction mixture was stirred at 60° C. for 4 hrs. Reaction was monitored with TLC. After completion of reaction, reaction was poured in ice cold water and extract with ethyl acetate (100 ml*3 times). Organic layer was washed with water (100 ml). The combined organic layer was dried over anhydrous sodium sulfate and concentrated under reduced pressure. The obtained crude comp. was purified by column chromatography (Hexane:Ethyl acetate—80:20). Pure comp.=96 mg. % Yield=19%.

Synthesis of Compound Formula 2 (5-(4-morpholinobutoxy)-2-(benzo[d][1,3]dioxol-6-yl)naphthalene-1,4-dione)

Morpholine (0.159 gm, 18.2 mmol) was dissolved in DMF (20 ml) and $K_2CO_3$ (0.505 gm, 36.4 mmol) at rt. Compound 11c (0.087 gm, 18.0 mmol) was added in reaction mixture at rt. Reaction mixture was stirred at rt for 16 hrs. Reaction was monitored with TLC. After completion of reaction, reaction was poured in ice cold water and extract with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=45 mg. % Yield=51%.

$^1H$ NMR ($CDCl_3$, 400 MHz): δ=7.83 (d, J=8.0 Hz, 1H), 7.69 (d, J=8.2 Hz, 1H), 7.31 (d, J=8.2 Hz, 1H), 7.11 (m, 2H), 6.90 (m, 2H), 6.02 (s, 2H), 4.32 (t, J=4.4 Hz, 2H), 3.78 (m, 4H), 3.04 (t, J=4.8 Hz, 2H), 2.82 (m, 4H), 1.94 (m, 2H), 1.82 (m, 2H).

Scheme 6

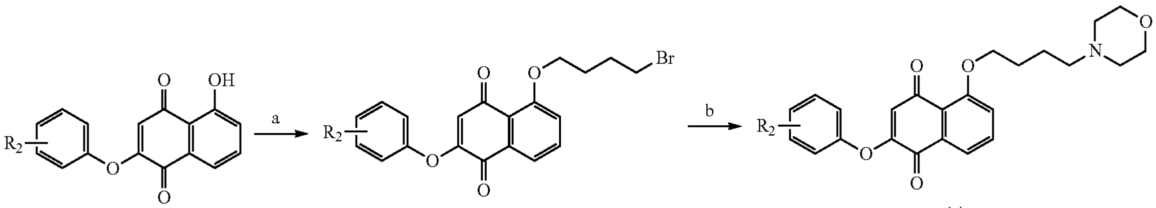

7
7a, $R_2$ = 4-$OCH_3$
7c, $R_2$ = 3,4 Methylene dioxy 13
13a, $R_2$ = 4-$OCH_3$
13c, $R_2$ = 3,4 Methylene dioxy 14
Formula 44, $R_2$ = 4-$OCH_3$
Formula 47, $R_2$ = 3,4 Methylene dioxy Reagents and conditions: a. Dibromobutane, TBAB, NaOH, $H_2O$, 60° C., 4 hrs b. Morpholine, $K_2CO_3$, DMF, RT 12 hrs Synthesis of Compound 13a (5-(4-bromobutoxy)-2-(4-methoxyphenoxy)naphthalene-1,4-dione)

Dibromobutane (14.53 gm, 67.5 mmol)) was added dropwise to a solution of Compound 7a (2.0 gm, 6.75 mmol), NaOH (0.54 gm, 13.5 mmol), TBAB (218 mg, 0.67 mmol) and water (50 ml). Reaction mixture was stirred at 60° C. for 3 hrs. Reaction was monitored with TLC. After completion of reaction, reaction was poured in ice cold water and extract with ethyl acetate (100 ml*4 times). Organic layer was washed with water (100 ml). The combined organic layer was dried over anhydrous sodium sulfate and concentrated under reduced pressure. The obtained crude comp. was purified by column chromatography (Hexane:Ethyl acetate—80:20). Pure comp.=1.79 gm. % Yield=61%.

Synthesis of Compound 13c (5-(4-bromobutoxy)-2-(benzo[d][1,3]dioxol-5-yloxy)naphthalene-1,4-dione Dibromobutane (0.5 gm, 16.1 mmol)) was added dropwise to a solution of Compound 7c (0.35 gm, 10.35 mmol), NaOH (0.129 gm, 32.2 mmol), TBAB (52 mg, 1.61 mmol) and water (20 ml). Reaction mixture was stirred at 60° C. for 3 hrs. Reaction was monitored with TLC. After completion of reaction, reaction was poured in ice cold water and extract with ethyl acetate (100 ml*3 times). Organic layer was washed with water (100 ml). The combined organic layer was dried over anhydrous sodium sulfate and concentrated under reduced pressure. The obtained crude comp. was purified by column chromatography (Hexane:Ethyl acetate—80:20). Pure comp.=0.4 gm. % Yield=55%.

Synthesis of Compound Formula 44 (2-(4-methoxyphenoxy)-5-(4-morpholinobutoxy) naphthalene-1,4-dione)

Morpholine (0.121 gm, 1.16 mmol) was dissolved in DMF (20 ml) and $K_2CO_3$ (0.320 gm, 2.32 mmol) at rt. Compound 13a (0.5 gm, 1.16 mmol) was added in reaction mixture at rt. Reaction mixture was stirred at rt for 16 hrs. Reaction was monitored with TLC. After completion of reaction, reaction was poured in ice cold water and extract with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=235 mg. % Yield=48%.

Synthesis of Compound Formula 47(5-(4-morpholinobutoxy)-2-(benzo[d][1,3]dioxol-5-yloxy) naphthalene-1,4-dione)

Morpholine (0.082 gm, 9.43 mmol) was dissolved in DMF (20 ml) and $K_2CO_3$ (0.217 gm, 15.7 mmol) at RT. Compound 13c (0.35 gm, 7.86 mmol) was added in reaction mixture at RT. Reaction mixture was stirred at RT for 16 hrs. Reaction was monitored with TLC. After completion of reaction, reaction was poured in ice cold water and extract with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=25 mg. % Yield=7%.

$^1H$ NMR ($CDCl_3$, 400 MHz): δ=7.85 (d, J=0.8 Hz, 1H), 7.66 (dd, J=1.2 Hz, 8.4 Hz, 1H), 7.32 (d, J=0.8 Hz, 1H), 6.83 (d, J=8 Hz, 1H), 6.61 (dd, J=2.4 Hz, 7.6 Hz, 2H), 6.03 (s, 2H), 5.88 (s, 1H), 4.16 (t, J=5.6 Hz, 2H), 3.71 (m, 4H), 2.45 (m, 6H), 1.91 (m, 2H), 1.85 (m, 2H)

Scheme 7

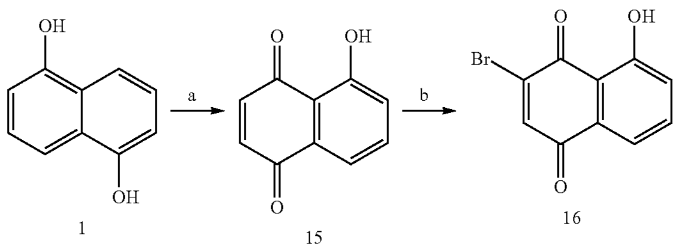

1

15

16

Reagents and conditions: a. CuCl, ACN, $O_2$, RT, 10 hrs, b. Bromine, AcOH, RT, 30 min Synthesis of 5-hydroxy-1,4-napthoquinone (15)

In a 450 ml autoclave reactor, acetonitrile (30 ml), CuCl (0.78 g, 39.4 mmol) was added portions at room temperature. A solution of 1, 5 dihydroxynaptalene (1 g, 31.3 mmol) in acetonitrile (200 ml) was added in reaction mixture at RT. 3 kg/cm$^2$ Oxygen pressure was applied to the reaction mixture. Oxygen atmosphere maintained under vigorous stirring. Reaction mixture was stirred at RT for 10 hours. The solution was concentrated in vacuum and the crude product was purified by column chromatography (Hexane: EtOAc, 80:20). Pure comp.=0.45 gm. % Yield=37%, M.p. 157° C.; H NMR (300 MHz, $CDCl_3$): δ=11.91 (s, 1H), 7.69-7.60 (m, 2H), 7.29 (dd, J=7.3, 2.5 Hz, 1H), 6.96 ppm (s, 2H).

Synthesis of 3-Bromo-5-hydroxy-(1,4)napthoquinone (16)

5-hydroxy-1,4-napthoquinone (15) (1 g, 57.1 mmol) was suspended in 15 ml of glacial Acetic acid. Bromine (1.00 eq. 0.3 ml, 57.1 mmol) was added in RM at room temperature under exclusion of light. The reaction mass was stirred for 20 min under exclusion of light and subsequently poured into ice (100 gm). The mixture was vigorous stirred for 30 min and precipitated was filtered as orange solid in vacuum and washed with little ice water. The mixture was immediately taken in single neck RBF and ethanol (8 ml) was added in it. Reaction mixture was stirred with pre-heated oil bath for 10 min under reflux. The crude product obtained as red solid from the reaction solution, was filtered in vacuum and washed with 5 ml cold ethanol. Crude product was purified by column chromatography (Hexane: EtOAc, 80:20). Pure comp.=0.7 gm. % Yield=47%.

M.p. 168° C.; $^1$H NMR (300 MHz, $CDCl_3$): δ=11.73 (s, 1H), 7.68 (t, J=7.4 Hz, 1H), 7.64 (dd, J=7.4, 2.0 Hz, 1H), 7.50 (s, 1H), 7.31 ppm (dd, J=7.5, 2.0 Hz, 1H)

at RT for 3 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—95:5). Pure comp.=1.13 gm. % Yield=51%.

Synthesis of Compound 17c (2-(benzo[d][1,3]dioxol-6-yloxy)-8-hydroxynaphthalene-1,4-dione)

Two necked RBF (100 mL) was charged with sesamol (1.08 gm, 78.4 mmol) and DMF (50 ml). $K_2CO_3$ (0.54 g, 78.4 mmol) was added in reaction mixture and stirred at RT Scheme 8

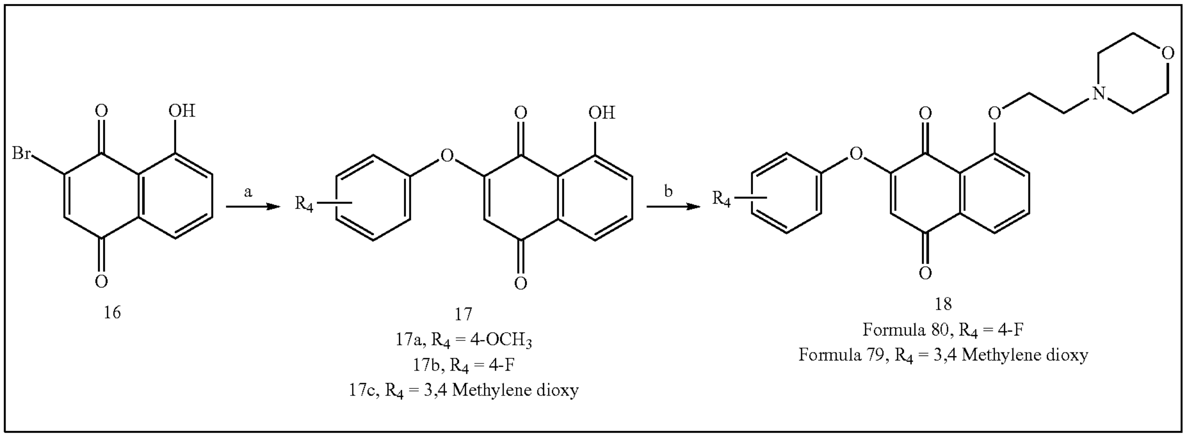

Reagents and conditions: a. $K_2CO_3$, DMF, RT, 4 hrs, b. 4-(2-chloroethyl)morpholine hydrochloride, $K_2CO_3$, DMF, 100° C., 4 hrs Synthesis of Compound 17a (2-(4-methoxyphenoxy)-8-hydroxynaphthalene-1,4-Dione)

Two necked RBF (250 mL) was charged with 4-Methoxy phenol (0.972 gm, 78.4 mmol) and DMF (50 ml). $K_2CO_3$ (1.08 g, 78.4 mmol) was added in reaction mixture and stirred at RT for 15 min. Compound 16 (2.0 gm, 78.4 mmol) was added in reaction mixture. Reaction mixture was stirred at RT for 3 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—95:5). Pure comp.=1.0 gm. % Yield=43%.

Synthesis of Compound 17b (2-(4-fluorophenoxy)-8-hydroxynaphthalene-1,4-dione)

Two necked RBF (100 mL) was charged with 4-Fluoro phenol (0.879 gm, 78.4 mmol) and DMF (50 ml). $K_2CO_3$ (1.08 g, 78.4 mmol) was added in reaction mixture and stirred at RT for 15 min. Compound 16 (2.0 gm, 78.4 mmol) was added in reaction mixture. Reaction mixture was stirred for 15 min. Compound 4 (2.0 gm, 78.4 mmol) was added in reaction mixture. Reaction mixture was stirred at RT for 4 hrs. Reaction was monitored with TLC. After completion, reaction mixture was poured in water (200 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Pet ether: Ethyl acetate—95:5). Pure comp.=0.676 gm. % Yield=25%.

Synthesis of Compound Formula 80(8-(2-morpholinoethoxy)-2-(4fluorophenoxy)naphthalene-1,4-dione)

Two necked RBF (100 mL) was charged with compound 17b (0.5 gm, 17.66 mmol) and DMF (20 ml). $K_2CO_3$ (0.488 g, 35.33 mmol) was added in reaction mixture and stirred at RT for 15 min. 4-(2-chloroethyl)morpholine hydrochloride (0.394 gm, 21.2 mmol) was added in reaction mixture. Reaction mixture was heated at 100° C. for 3 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=35 mg. % Yield=33%.

$^1$H NMR ($CDCl_3$, 400 MHz): δ=7.71 (d, J=1.2 Hz, 1H), 7.68 (m, 1H), 7.31 (dd, J=1.2 Hz & 7.6 Hz, 1H), 7.17 (m, 4H), 5.84 (s, 1H), 4.31 (t, J=5.6 Hz, 2H), 3.76 (m, 4H), 2.98 (t, J=5.6 Hz, 2H), 2.72 (m, 4H).

Synthesis of Compound Formula 79 (8-(2-morpholinoethoxy)-2-(benzo[d][1,3]dioxol-6-yloxy) naphthalene-1,4-dione)

Two necked RBF (100 mL) was charged with compound 7c (0.5 gm, 17.66 mmol) and DMF (20 ml). $K_2CO_3$ (0.49 g, 35.3 mmol) was added in reaction mixture and stirred at RT for 15 min. 4-(2-chloroethyl)morpholine hydrochloride (0.395 gm, 21.2 mmol) was added in reaction mixture. Reaction mixture was heated at 100° C. for 2 hrs. Reaction was monitored with TLC. After completion, reaction mixture was cooled to RT and reaction mixture was poured in water (100 ml) and extracted with ethyl acetate (100 ml*3 times). Organic layer was washed with water (100 ml*3). The combined organic layer was dried over anhydrous sodium sulfate and concentrated under reduced pressure. The obtained crude comp. was purified by column chromatography (Ethyl acetate:Methanol—95:5). Pure comp.=294 mg. % Yield=42%.

$^1$H NMR ($CDCl_3$, 400 MHz): δ=7.74 (d, J=0.8 Hz, 1H), 7.68 (dd, J=1.2 Hz, 8.4 Hz, 1H), 7.29 (d, J=0.8 Hz, 1H), 6.83 (d, J=8 Hz, 1H), 6.60 (dd, J=2.4 Hz, 7.6 Hz, 1H), 6.56 (d, J=2.4 Hz, 1H), 6.03 (s, 2H), 5.91 (s, 1H), 4.30 (t, J=5.6 Hz, 2H), 3.76 (m, 4H), 2.98 (t, J=5.6 Hz, 2H), 2.72 (m, 4H).

Test Data

The following tests were conducted to determine the efficiency and non-toxicity of the compounds.

Cancer Cell assays

1. In Vitro Antiproliferative Assay (MTT Assay)

MTT assay is a simple and sensitive assay where, metabolic reducing activity of the cells is measured. The increase of this activity in time is taken as a parameter of cell growth. If treatment with a drug impairs this increase, the action is a consequence of growth inhibition, cell killing or both. The compounds of the present invention and standard cytotoxic drug (e.g. Cisplatin) were tested at different concentrations (1, 0.1, 0.01, 0.001 mM) using breast and prostate cancer cell lines. All cell lines were cultured in a 37° C. incubator with a 5% $CO_2$ environment. Compounds were dissolved in DMSO with a concentration of 0.1M (stock solution). Cells were seeded into 96-well plates at suitable plating efficiency.

Following plating efficiencies were standardized for MTT assay:

TABLE 1

| Cell lines | Name of the cell line | Plating efficiency (No. of cells/well or per 200 μl) |
|---|---|---|
| Breast | MDAMB231 | 10000 |
| Prostate | PC3 | 10000 |

In the MTT procedure, the cells were plated in 96 well plates as per predetermined plating efficiency (Table1). The plates were then incubated for 24 hrs in 5% $CO_2$ atmosphere at 37° C. Appropriate concentrations of the drugs were then added to the plate and further incubation was carried out for 48 hrs (in 5% $CO_2$ atmosphere at 37° C.). The assay plate was then centrifuged twice at 3000 rpm for 3 mins and supernatant was then discarded. 100 ul of MTT solution (0.5 mg/ml) was then added to each well of the plate and it was further incubated for 4 hrs (in 5% $CO_2$ atmosphere at 37° C.) Following 4 hr incubation, the plate was then centrifuged twice, and supernatant was aspirated off very carefully. 200 ul of DMSO was then added to each well to solubilize. MTT crystals and mixed well by shaking the plate. XY graph of log percent viability was then plotted against log drug concentration. IC50 (Drug concentration inhibiting the 50% of cell population) was then calculated by regression analysis.

Results of MTT Assay of the Compounds on Breast Cancer (MDAMB231cell Line) and Prostate Cancer (PC3 Cell Line).

TABLE 2

| Compounds | IC50 in μM MDAMB231 | IC50 in μM PC3 |
|---|---|---|
| Cisplatin | 30.97 | 35.89 |
| Formula 1 | 0.656 | 0.579 |
| Formula 2 | 0.566 | 0.344 |
| Formula 7 | 0.451 | 0.246 |
| Formula 37 | 4.61 | 4.44 |
| Formula 40 | 0.951 | 1.68 |
| Formula 41 | 3.06 | 2.73 |
| Formula 43 | 1.01 | 0.50 |
| Formula 46 | 1.37 | 1.35 |
| Formula 47 | 0.97 | 0.582 |
| Formula 52 | 3.13 | 4.32 |
| Formula 67 | 3.09 | 4.11 |
| Formula 68 | 3.18 | 4.73 |
| Formula 69 | 2.75 | 2.12 |
| Formula 70 | 3.02 | 2.23 |
| Formula 71 | 1.35 | 3.55 |
| Formula 72 | 1.01 | 0.743 |
| Formula 73 | 2.18 | 3.05 |
| Formula 74 | 0.109 | 0.225 |
| Formula 75 | 0.566 | 0.306 |
| Formula 76 | 2.48 | 0.324 |
| Formula 77 | 2.22 | 0.269 |
| Formula 78 | 5.5 | 3.46 |
| Formula 79 | 0.502 | 0.527 |
| Formula 80 | 0.352 | 0.482 |
| Formula 81 | 0.631 | 2.19 |

| Compounds | IC50 in nM MDAMB231/MCF7 | IC50 in nM PC3 |
|---|---|---|
| Formula 82 | 970/480 | 582 |
| Formula 83 | 860/660 | 721 |
| Formula 84 | 562 | 492 |
| Formula 85 | 4140 | 2360 |

Above Table indicates that the compounds exhibit very high potency on breast and prostate cancer cell lines in MTT Assay compared to standard therapeutic drug Cisplatin.

FIG. 1 to FIG. 50 show the activity of the compounds of Formulae 1, 2, 7, 37, 40, 41, 43, 46, 47, 52, 67, 68, 69, 70, 71, 72, 73, 74, 75, 76, 77, 78, 79, 80 and 81 respectively on breast and prostate cancer cell lines in comparison with cisplatin. It was found that the compounds exhibited higher anticancer activity in comparison with cisplatin.

2. Soft Agar Assay

The Soft Agar Colony-formation Assay is an anchorage-independent growth assay in soft agar, which is one of the most stringent assays for detecting malignant transformation of cells. For this assay, malignant cells are cultured with appropriate controls in soft agar medium for 1-2 weeks. Following this incubation period, formed colonies can either be analyzed morphologically using cell stain and quantifying the number of colonies formed. The results of the assay are comparable to those obtained after injecting tumorigenic cells into nude mice and is regarded as the "gold standard" for testing the tumorigenicity of cells in vitro (one of the important features of cancer stem cells, (CSCs).

Briefly, for Soft Agar Assay a mixture of 50 ul of 2× medium (taken appropriately as per cell line) and 50 ul of 1.2% Bacto Agar were plated on to each well of 96 well micro titer assay plate. 10 ul of cells (of specific plating efficiency pre standardized for respective cell line) were mixed with 20 ul of 2× medium and 30 ul of 0.8% of Bacto Agar and 1.6 ul of drug (of appropriate concentration) in a vial and transferred to the solidified pre layers of the assay plates. The cells were then allowed to grow and form colonies at 37° C. and 5% CO2 for 1 week. An intermittent feeding with 50 ul of appropriate 2× medium was performed after 3 days of experimental set up. 16 ul of Alamar Blue (1.5 mg/ml) was then added to all the wells to quantify the developed colonies. The plates were incubated for 24 hrs at 37° C. Absorbance was then measured at 630 nm. XY graph of log Percent viability was then plotted against log drug concentration. IC50 (Drug concentration inhibiting the 50% of cell population) was then calculated by regression analysis.

Following plating efficiencies were standardized for Soft Agar Assay:

TABLE 3

| Cell lines | Name of the cell line | Plating efficiency (No. of cells/well) |
|---|---|---|
| Breast | MDAMB231 | 7500 |
| Prostate | PC3 | 5000 |

Results of Soft Agar Assay of the Compounds on Breast Cancer (MDAMB231cell Line) and Prostate Cancer (PC3 Cell Line).

TABLE 4

| | IC50 in micromolar | |
|---|---|---|
| Compounds | Breast Cancer MDAMB231 | Prostate cancer PC3 |
| Cisplatin | 35.16 | 34.43 |
| Formula 2 | 2.08 | 2.65 |
| Formula 40 | 0.353 | 0.422 |
| Formula 41 | 1.63 | 2.67 |
| Formula 43 | 0.662 | 0.415 |
| Formula 52 | 3.88 | 3.27 |
| Formula 67 | 3.17 | 2.21 |
| Formula 68 | 2.37 | 2.53 |
| Formula 71 | 1.79 | 3.31 |
| Formula 72 | 3.72 | 0.60 |
| Formula 73 | 3.77 | 2.68 |

Above Table indicates that the compounds are exhibiting very high potency on breast and prostate cancer cell lines in Soft Agar Assay compared to standard therapeutic drug Cisplatin.

Figure 51:
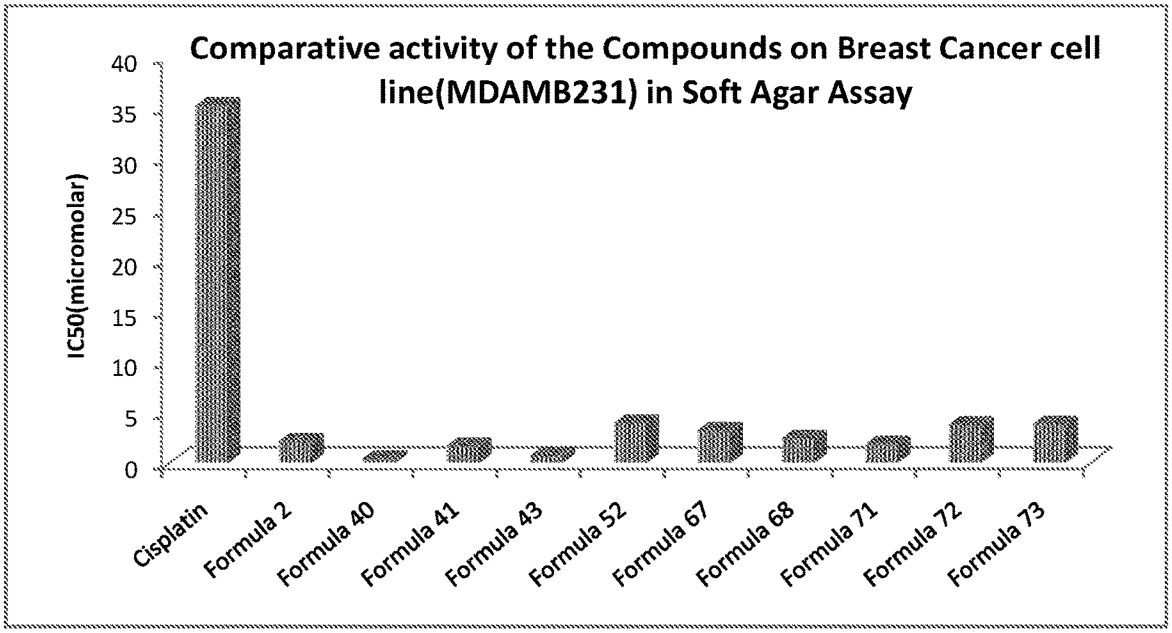
FIG. 51 illustrates the activity of compounds of Formulae 2, 40, 41, 43, 52, 67, 68, 71, 72, 73 and cisplatin on breast cancer MDAMB231 cell line in soft agar assay.

FIG. 51 shows the activity of the compounds of Formulae 2, 40, 41, 43, 52, 67, 68, 71, 72 and 73 respectively on breast cancer cell line in comparison with cisplatin. It was found that the compounds exhibit higher anticancer activity in comparison with cisplatin.

Figure 52:
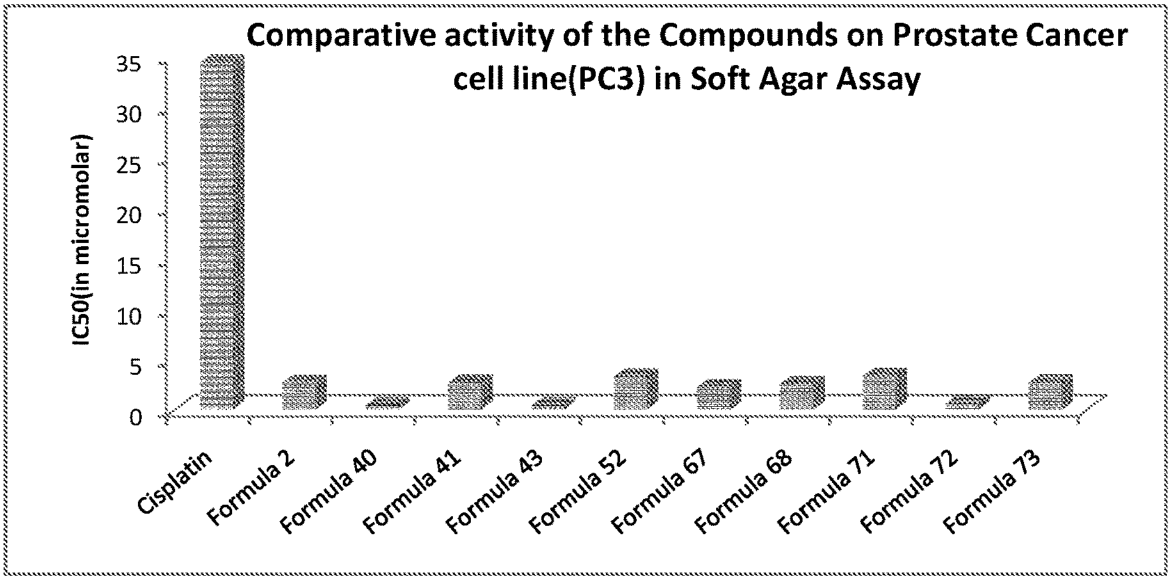
FIG. 52 illustrates the activity of compounds of Formulae 2, 40, 41, 43, 52, 67, 68, 71, 72, 73 and cisplatin on prostate cancer PC3 cell line in soft agar assay.

FIG. 52 shows the activity of the compounds of Formulae 2, 40, 41, 43, 52, 67, 68, 71, 72 and 73 respectively on prostate cancer cell line in comparison with cisplatin. It was found that the compounds exhibit higher anticancer activity in comparison with cisplatin.

3. Stem Cell Assays

In Vitro Sphere-forming Assay: Sphere assay measures the ability of cancer stem cells (CSCs) to form spheres in specially designed serum-free medium. This assay was used to measure the killing efficiency of the test compounds as compared to the standard chemotherapeutic drug, Cisplatin.

Materials and Reagents: 50× B27 Supplement (Life Technologies, Invitrogen, Catlog No.: 17502-044), Fibroblast Growth Factor (FGF) (Sigma-Aldrich, Catlog No.: F029125), Epidermal Growth Factor (EGF) (Sigma-Aldrich, Catlog No.: E9644), Insulin (Sigma, Catlog No.: 19278), Dulbecco's Modified Eagle Medium/F12 (HiMedia Catlog No.: AL139-6), Dulbecco's Phosphate Buffered Saline (HiMedia Catlog No.: TL1006), Trypan Blue (TC193), Prostate Epithelial Media (LONZA, Catlog No.: CC-3166) MEGM (LONZA, Catlog No.: CC-3051), Heparin (Sigma, Catlog No.: H3393), Penstrep (HiMedia, Catlog No.: A002)

Mammosphere Media Preparation (For 100 mL): 1 g methyl cellulose autoclaved with magnetic stirrer, 100 ml plain media (MEBM) was added and dissolved under magnetic stirring. After complete dissolution FGF-80 μL, EGF-40 μL, Penstrep-1 mL, Heparin-400 μL was added.

Prostosphere Media Preparation (For 100 mL):1 g methyl cellulose autoclaved with magnetic stirrer, 100 mL plain media (Prostate Epithelial Basal Medium) was added and dissolved, under magnetic stirring. After complete dissolution, Insulin-40 μL, B27-2 mL, EGF-80 μL, Penstrep-1 ml was added.

Procedure—The cells were trypsinised and made into single-cell suspension by passing through cell strainers (100 μl and 40 μl, respectively), The cells were diluted at a concentration of 2000 cells/100 μL and suspended in either Mammosphere (for breast cell lines) or Prostosphere (for prostate cell lines). 100 μL of this suspension was added into each well of 96-well suspension plates and incubated at 37° C., 5% $CO_2$ for 24 hrs. Appropriate concentrations of the drugs (2 μL) were added into respective wells with 100 μL of stem cell culture medium. Plates were incubated at 37° C., 50 $CO_2$ for 72 hrs. After incubation, 2.5 μL of the respective drug concentration and 50 μL of stem cell culture medium were added into each well and the plates were further incubated at 37° C., 50% $CO_2$ for 72 hrs. 3 μL of the respective drug concentration was added with 50 μL of stem cell culture medium again after incubation and plates were reincubated for 72 hrs at 37° C., 50 $CO_2$. Number of primary spheres formed for each concentration were counted. The spheres were converted to 0 viability of spheres compared to untreated (Growth Control with DMSO, GCD). A comparative graph of 00 viability of spheres was plotted against the drug concentration and compared with standard therapeutic drug Cisplatin.

Results of In-Vitro Sphere Forming Assay of the Compounds on Breast Cancer (MIDAMB231 Cell Line) and Prostate Cancer (PC3 Cell Line) at a Plating Efficiency of 2000 Cells/Well (n=6±S.D).

TABLE 5

3D sphere count of MDAMB231 in Mammosphere media at plating efficiency of 2000 cells/well (n = 6 ± S.D)

| Drug Concentration in uM | 250 | 25 | 2.5 | 0.25 | 0.025 | 0.0025 | GC (Growth Control) | GCD (Growth Control With DMSO) |
|---|---|---|---|---|---|---|---|---|
| Cisplatin | 28(±3) | 42(±3) | 51(±3) | 63(±4) | 71(±3) | — | 79(±3) | 77(±2) |
| Formula 1 | 10(±2) | 24(±4) | 34(±4) | 48(±4) | 64(±5) | — | 79(±3) | 77(±2) |
| Cisplatin | 28(±3) | 42(±3) | 51(±3) | 63(±4) | 71(±3) | — | 79(±3) | 77(±2) |
| Formula 2 | 11(±3) | 23(±3) | 36(±3) | 51(±3) | 65(±5) | — | 79(±3) | 77(±2) |
| Cisplatin | 26(±3) | 43(±3) | 53(±3) | 60(±3) | 69(±3) | — | 74(±4) | 71(±3) |
| Formula 7 | 11(±3) | 22(±3) | 31(±3) | 43(±3) | 59(±3) | — | 74(±4) | 71(±3) |
| Cisplatin | 34(±4) | 54(±4) | 65(±5) | 75(±5) | 91(±4) | — | 103(±2) | 100(±3) |
| Formula 37 | 23(±3) | 39(±3) | 56(±4) | 66(±5) | 82(±4) | — | 103(±2) | 100(±3) |
| Cisplatin | — | 22(±4) | 43(±3) | 56(±3) | 64(±3) | 72(±4) | 81(±3) | 77(±4) |
| Formula 40 | — | 8(±2) | 21(±3) | 32(±4) | 43(±3) | 60(±3) | 81(±3) | 77(±4) |
| Cisplatin | — | 22(±4) | 43(±3) | 56(±3) | 64(±3) | 72(±4) | 81(±3) | 77(±4) |
| Formula 41 | — | 15(±3) | 26(±3) | 40(±3) | 54(±4) | 66(±4) | 81(±3) | 77(±4) |
| Cisplatin | — | 34(±4) | 54(±4) | 65(±5) | 75(±5) | 91(±4) | 103(±2) | 100(±3) |
| Formula 43 | — | 21(±3) | 33(±4) | 46(±3) | 61(±3) | 82(±4) | 103(±2) | 100(±3) |
| Cisplatin | — | 34(±3) | 46(±3) | 58(±4) | 71(±3) | 85(±3) | 94(±4) | 90(±4) |
| Formula 46 | — | 18(±3) | 29(±3) | 44(±4) | 54(±4) | 67(±5) | 94(±4) | 90(±4) |
| Cisplatin | — | 35(±4) | 53(±3) | 62(±3) | 73(±3) | 83(±3) | 94(±3) | 90(±3) |
| Formula 47 | — | 16(±3) | 25(±5) | 39(±3) | 53(±3) | 71(±2) | 94(±3) | 90(±3) |
| Cisplatin | — | 28(±3) | 42(±3) | 51(±3) | 63(±4) | 71(±3) | 79(±3) | 77(±2) |
| Formula 52 | — | 24(±3) | 34(±4) | 43(±3) | 55(±7) | 69(±3) | 79(±3) | 77(±2) |
| Cisplatin | — | 33(±2) | 40(±2) | 51(±2) | 63(±4) | 73(±4) | 88(±3) | 83(±3) |
| Formula 67 | — | 31(±2) | 40(±5) | 47(±5) | 58(±3) | 67(±2) | 88(±3) | 83(±3) |
| Cisplatin | — | 33(±2) | 40(±2) | 51(±2) | 63(±4) | 73(±4) | 88(±3) | 83(±3) |
| Formula 68 | — | 27(±2) | 33(±2) | 39(±3) | 47(±2) | 54(±2) | 88(±3) | 83(±3) |
| Cisplatin | — | 27(±3) | 50(±4) | 59(±5) | 69(±3) | 77(±3) | 85(±3) | 82(±4) |
| Formula 69 | — | 16(±2) | 29(±3) | 47(±3) | 58(±3) | 71(±3) | 85(±3) | 82(±4) |
| Cisplatin | — | 27(±3) | 50(±4) | 59(±5) | 69(±3) | 77(±3) | 85(±3) | 82(±4) |
| Formula 70 | — | 20(±2) | 34(±3) | 51(±3) | 61(±3) | 71(±3) | 85(±3) | 82(±4) |
| Cisplatin | — | 27(±3) | 50(±4) | 59(±5) | 69(±3) | 77(±3) | 85(±3) | 82(±4) |
| Formula 71 | — | 11(±2) | 28(±3) | 44(±4) | 53(±4) | 65(±5) | 85(±3) | 82(±4) |
| Cisplatin | — | 26(±3) | 43(±3) | 53(±3) | 60(±3) | 69(±3) | 74(±4) | 71(±3) |
| Formula 72 | — | 14(±3) | 24(±2) | 34(±3) | 48(±3) | 60(±3) | 74(±4) | 71(±3) |
| Cisplatin | — | 26(±3) | 43(±3) | 53(±3) | 60(±3) | 69(±3) | 74(±4) | 71(±3) |
| Formula 73 | — | 14(±3) | 25(±3) | 36(±4) | 50(±3) | 62(±4) | 74(±4) | 71(±3) |
| Cisplatin | — | 30(±4) | 50(±3) | 58(±3) | 65(±3) | 76(±7) | 86(±3) | 81(±3) |
| Formula 74 | — | 10(±2) | 22(±4) | 29(±3) | 39(±3) | 60(±3) | 86(±3) | 81(±3) |
| Cisplatin | — | 29(±3) | 48(±3) | 57(±4) | 67(±3) | 74(±4) | 83(±3) | 80(±4) |
| Formula 75 | — | 14(±3) | 26(±3) | 36(±4) | 45(±3) | 64(±3) | 83(±3) | 80(±4) |
| Cisplatin | — | 34(±4) | 53(±4) | 61(±3) | 72(±4) | 84(±4) | 94(±4) | 90(±4) |
| Formula 76 | — | 26(±4) | 36(±3) | 51(±3) | 61(±2) | 74(±3) | 94(±4) | 90(±4) |
| Cisplatin | — | 34(±4) | 53(±4) | 61(±3) | 72(±4) | 84(±4) | 94(±4) | 90(±4) |
| Formula 77 | — | 27(±3) | 36(±4) | 48(±3) | 63(±5) | 74(±4) | 94(±4) | 90(±4) |
| Cisplatin | — | 34(±4) | 53(±4) | 61(±3) | 72(±4) | 84(±4) | 94(±4) | 90(±4) |
| Formula 78 | — | 32(±3) | 42(±4) | 52(±4) | 65(±5) | 79(±3) | 94(±4) | 90(±4) |
| Cisplatin | — | 34(±3) | 46(±3) | 58(±4) | 71(±3) | 85(±3) | 94(±4) | 90(±4) |
| Formula 79 | — | 17(±3) | 24(±3) | 35(±3) | 51(±3) | 69(±3) | 94(±4) | 90(±4) |
| Cisplatin | — | 34(±3) | 46(±3) | 58(±4) | 71(±3) | 85(±3) | 94(±4) | 90(±4) |
| Formula 80 | — | 14(±4) | 21(±3) | 35(±4) | 48(±3) | 68(±4) | 94(±4) | 90(±4) |
| Cisplatin | — | 34(±4) | 54(±4) | 65(±5) | 75(±5) | 91(±4) | 103(±2) | 100(±3) |
| Compound 81 | — | 21(±3) | 33(±4) | 46(±3) | 61(±3) | 82(±4) | 103(±2) | 100(±3) |

The above results indicate that the above compounds are more effective in inhibiting spheres of MDAMB231 compared to cisplatin.

FIG. 1, FIG. 3, FIG. 5, FIG. 7, FIG. 9, FIG. 11, FIG. 13, FIG. 15, FIG. 17, FIG. 19, FIG. 21, FIG. 23, FIG. 25, FIG. 27, FIG. 29, FIG. 31, FIG. 33, FIG. 35, FIG. 37, FIG. 39, FIG. 41, FIG. 43, FIG. 45, FIG. 47, and FIG. 49 refer to compounds of Formulae 1, 2, 7, 37, 40, 41, 43, 46, 47, 52 and 67-81 for MDAMB231 cell line respectively.

FIG. 1, FIG. 3, FIG. 5, FIG. 7, FIG. 9, FIG. 11, FIG. 13, FIG. 15, FIG. 17, FIG. 19, FIG. 21, FIG. 23, FIG. 25, FIG. 27, FIG. 29, FIG. 31, FIG. 33, FIG. 35, FIG. 37, FIG. 39, FIG. 41, FIG. 43, FIG. 45, FIG. 47, and FIG. 49 illustrate the percentage viability of spheres obtained from conversion of the number of spheres formed and compared with growth control with DMSO (GCD), wherein GCD is considered as 100% viability. The sphere count results for respective drug concentration indicated in Table 6 have been converted to percentage viability of spheres for graphical representation. The figures and Table 6 indicate that there is a decrease in percentage viability of spheres of MDAMB231 in the presence of compounds of Formulae 1, 2, 7, 37, 40, 41, 43, 46, 47, 52 and 67-81 in comparison to cisplatin.

TABLE 6

% Viability of spheres (MDAMB231)

| Drug Concentration in uM | Untreated (GCD) | 250 | 25 | 2.5 | 0.25 | 0.025 | 0.0025 |
|---|---|---|---|---|---|---|---|
| Cisplatin | 100(±3) | 36(±3) | 54(±3) | 66(±4) | 82(±3) | 92(±2) | — |
| Formula 1 | 100(±2) | 13(±4) | 31(±4) | 44(±4) | 62(±5) | 83(±2) | — |
| Cisplatin | 100(±3) | 36(±3) | 54(±3) | 66(±4) | 82(±3) | 92(±2) | — |
| Formula 2 | 100(±3) | 14(±3) | 30(±3) | 46(±3) | 66(±5) | 84(±2) | — |
| Cisplatin | 100(±3) | 36(±3) | 60(±3) | 74(±3) | 84(±3) | 97(±3) | — |
| Formula 7 | 100(±3) | 15(±3) | 31(±3) | 43(±3) | 60(±3) | 83(±3) | — |
| Cisplatin | 100(±4) | 34 (±4) | 54(±5) | 65(±5) | 75(±4) | 91(±3) | — |
| Formula 37 | 100(±3) | 23 (±3) | 39(±4) | 56(±5) | 66(±4) | 82(±3) | — |
| Cisplatin | 100(±4) | — | 28(±3) | 56(±3) | 73(±3) | 83(±4) | 93(±4) |
| Formula 40 | 100(±4) | — | 10(±2) | 27(±3) | 41±4) | 56(±3) | 78(±3) |
| Cisplatin | 100(±4) | — | 28(±4) | 56(±3) | 73(±3) | 83(±3) | 93(±4) |
| Formula 41 | 100(±4) | — | 19(±3) | 34(±3) | 52(±3) | 70(±4) | 86(±4) |
| Cisplatin | 100(±3) | — | 34(±4) | 54(±4) | 65(±5) | 75(±5) | 91(±4) |
| Formula 43 | 100(±3) | — | 21(±3) | 33(±4) | 46(±3) | 61(±3) | 82(±4) |
| Cisplatin | 100(±4) | — | 37(±3) | 51(±3) | 64(±4) | 78(±3) | 94(±3) |
| Formula 46 | 100(±4) | — | 20(±3) | 32(±3) | 49(±4) | 60(±4) | 74(±5) |
| Cisplatin | 100(±3) | — | 39(±4) | 59(±3) | 69(±3) | 81(±3) | 92(±3) |
| Formula 47 | 100(±3) | — | 17(±3) | 27(±5) | 43(±3) | 59(±3) | 78(±2) |
| Cisplatin | 100(±3) | — | 39(±3) | 49(±4) | 62(±4) | 75(±3) | 87(±3) |
| Formula 52 | 100(±2) | — | 26(±3) | 38(±4) | 45(±3) | 50(±7) | 62(±3) |
| Cisplatin | 100(±3) | — | 39(±2) | 48(±2) | 61(±2) | 75(±4) | 88(±4) |
| Formula 67 | 100(±3) | — | 37(±2) | 48(±5) | 56(±5) | 69(±3) | 80(±2) |
| Cisplatin | 100(±3) | — | 39(±2) | 48(±2) | 61(±2) | 75(±4) | 88(±4) |
| Formula 68 | 100(±3) | — | 32(±2) | 39(±2) | 47(±3) | 53(±2) | 62(±2) |
| Cisplatin | 100(±4) | — | 33(±3) | 61(±4) | 72(±5) | 84(±3) | 94(±3) |
| Formula 69 | 100(±4) | — | 19(±2) | 35(±3) | 57(±3) | 70(±3) | 86(±3) |
| Cisplatin | 100(±4) | — | 33(±3) | 61(±4) | 72(±5) | 84(±3) | 94(±3) |
| Formula 70 | 100(±4) | — | 24(±2) | 41(±4) | 62(±4) | 74(±4) | 86(±4) |
| Cisplatin | 100(±4) | — | 33(±3) | 61(±4) | 72(±5) | 84(±3) | 94(±3) |
| Formula 71 | 100(±4) | — | 13(±2) | 34(±3) | 53(±4) | 64(±4) | 79(±5) |
| Cisplatin | 100(±3) | — | 36(±3) | 60(±3) | 74(±3) | 84(±3) | 97(±3) |
| Formula 72 | 100(±3) | — | 19(±3) | 33(±2) | 48(±3) | 67(±3) | 84(±3) |
| Cisplatin | 100(±3) | — | 36(±3) | 60(±3) | 74(±3) | 84(±3) | 97(±3) |
| Formula 73 | 100(±3) | — | 19(±3) | 35(±3) | 50(±4) | 70(±3) | 87(±4) |
| Cisplatin | 100(±3) | — | 37(±4) | 61(±3) | 71(±3) | 80(±3) | 93(±7) |
| Formula 74 | 100(±3) | — | 12(±2) | 27(±4) | 35(±3) | 48(±3) | 73(±3) |
| Cisplatin | 100(±4) | — | 36(±3) | 60(±3) | 71(±4) | 83(±3) | 92(±4) |
| Formula 75 | 100(±4) | — | 17(±3) | 32(±3) | 45(±4) | 56(±3) | 80(±3) |
| Cisplatin | 100(±4) | — | 37(±4) | 59(±4) | 67(±3) | 80(±4) | 93(±4) |
| Formula 76 | 100(±4) | — | 29(±4) | 40(±3) | 56(±3) | 67(±2) | 82(±3) |
| Cisplatin | 100(±4) | — | 37(±4) | 59(±4) | 67(±3) | 80(±4) | 93(±4) |
| Formula 77 | 100(±4) | — | 30(±3) | 40(±4) | 53(±3) | 70(±5) | 82(±4) |
| Cisplatin | 100(±4) | — | 37(±4) | 59(±4) | 67(±3) | 80(±4) | 93(±4) |
| Formula 78 | 100(±4) | — | 35(±3) | 46(±4) | 57(±4) | 67(±5) | 87(±3) |
| Cisplatin | 100(±4) | — | 37(±3) | 51(±3) | 64(±4) | 78(±3) | 94(±3) |
| Formula 79 | 100(±4) | — | 19(±3) | 26(±3) | 39(±3) | 56(±3) | 76(±3) |
| Cisplatin | 100(±4) | — | 37(±3) | 51(±3) | 64(±4) | 78(±3) | 94(±3) |
| Formula 80 | 100(±4) | — | 15(±4) | 23(±3) | 39(±4) | 53(±3) | 75(±4) |
| Cisplatin | 100(±3) | — | 34(±4) | 54(±4) | 65(±5) | 75(±5) | 91(±4) |
| Formula 81 | 100(±3) | — | 21(±3) | 33(±4) | 46(±3) | 61(±3) | 82(±4) |

TABLE 7

3D sphere count of PC3 in Prostosphere media at plating efficiency of 2000 cells/well (n = 6 ± S.D).

| Drug Concentration in uM | 250 | 25 | 2.5 | 0.25 | 0.025 | 0.0025 | GC(Growth Control) | GCD(Growth Control With DMSO) |
|---|---|---|---|---|---|---|---|---|
| Cisplatin | 35(±3) | 46(±3) | 56(±3) | 69(±3) | 77(±3) | — | 86(±2) | 81(±4) |
| Formula 1 | 13(±3) | 25(±3) | 37(±3) | 51(±3) | 65(±3) | — | 86(±2) | 81(±4) |
| Cisplatin | 35(±3) | 46(±3) | 56(±3) | 69(±3) | 77(±3) | — | 86(±2) | 81(±4) |
| Formula 2 | 8(±2) | 17(±3) | 32(±4) | 53(±3) | 63(±4) | — | 86(±2) | 81(±4) |
| Cisplatin | 33(±3) | 50(±4) | 59(±3) | 69(±3) | 76(±4) | — | 82(±4) | 80(±4) |
| Formula 7 | 9(±2) | 17(±3) | 28(±2) | 40(±3) | 57(±3) | — | 82(±4) | 80(±4) |
| Cisplatin | 32(±3) | 55(±3) | 66(±6) | 78(±3) | 89(±3) | — | 103(±3) | 100(±3) |
| Formula 37 | 20(±4) | 37(±4) | 56(±4) | 69(±3) | 89(±3) | — | 103(±3) | 100(±3) |
| Cisplatin | — | 27(±3) | 45(±5) | 65(±5) | 73(±4) | 79(±3) | 91(±3) | 87(±3) |
| Formula 40 | — | 15(±3) | 30(±3) | 41(±3) | 57(±3) | 70(±5) | 91(±3) | 87(±3) |
| Cisplatin | — | 27(±3) | 45(±5) | 65(±5) | 73(±4) | 79(±3) | 91(±3) | 87(±3) |

TABLE 7-continued

| 3D sphere count of PC3 in Prostosphere media at plating efficiency of 2000 cells/well (n = 6 ± S.D). | | | | | | | | |
|---|---|---|---|---|---|---|---|---|
| Drug Concentration in uM | 250 | 25 | 2.5 | 0.25 | 0.025 | 0.0025 | GC(Growth Control) | GCD(Growth Control With DMSO) |
| Formula 41 | — | 24(±4) | 40(±4) | 47(±5) | 63(±3) | 74(±4) | 91(±3) | 87(±3) |
| Cisplatin | — | 32(±3) | 55(±3) | 66(±6) | 78(±3) | 89(±3) | 103(±3) | 100(±3) |
| Formula 43 | — | 21(±3) | 30(±4) | 46(±4) | 57(±5) | 75(±4) | 103(±3) | 100(±3) |
| Cisplatin | — | 31(±3) | 41(±3) | 51(±3) | 61(±3) | 73(±3) | 85(±3) | 80(±3) |
| Formula 46 | — | 18(±3) | 29(±3) | 41(±3) | 54(±4) | 66(±3) | 85(±3) | 80(±3) |
| Cisplatin | — | 33(±3) | 49(±3) | 61(±4) | 71(±3) | 76(±3) | 85(±3) | 80(±3) |
| Formula 47 | — | 15(±3) | 23(±3) | 35(±3) | 46(±4) | 62(±4) | 85(±3) | 80(±3) |
| Cisplatin | — | 35(±3) | 46(±3) | 56(±3) | 69(±3) | 77(±3) | 86(±2) | 81(±4) |
| Formula 52 | — | 25(±3) | 40(±4) | 51(±3) | 63(±4) | 71(±3) | 86(±2) | 81(±4) |
| Cisplatin | — | 34(±2) | 44(±4) | 58(±5) | 69(±6) | 74(±4) | 91(±3) | 87(±1) |
| Formula 67 | — | 32(±3) | 39(±2) | 45(±3) | 56(±3) | 61(±5) | 91(±3) | 87(±1) |
| Cisplatin | — | 34(±2) | 44(±4) | 58(±5) | 69(±6) | 74(±4) | 91(±3) | 87(±1) |
| Formula 68 | — | 21(±2) | 27(±2) | 36(±3) | 48(±3) | 54(±4) | 91(±3) | 87(±1) |
| Cisplatin | — | 27(±2) | 51(±3) | 62(±3) | 72(±4) | 80(±2) | 88(±2) | 82(±2) |
| Formula 69 | — | 17(±3) | 29(±2) | 40(±2) | 53(±3) | 76(±3) | 88(±2) | 82(±2) |
| Cisplatin | — | 27(±2) | 51(±3) | 62(±3) | 72(±4) | 80(±2) | 88(±2) | 82(±2) |
| Formula 70 | — | 25(±3) | 34(±4) | 41(±3) | 55(±2) | 78(±2) | 88(±2) | 82(±2) |
| Cisplatin | — | 27(±3) | 50(±4) | 59(±5) | 69(±3) | 77(±3) | 85(±3) | 82(±4) |
| Formula 71 | — | 11(±2) | 28(±3) | 44(±4) | 53(±4) | 65(±5) | 85(±3) | 82(±4) |
| Cisplatin | — | 33(±3) | 50(±4) | 59(±3) | 69(±3) | 76(±4) | 82(±4) | 80(±4) |
| Formula 72 | — | 13(±3) | 29(±2) | 37(±3) | 51(±3) | 65(±3) | 82(±4) | 80(±4) |
| Cisplatin | — | 33(±3) | 50(±4) | 59(±3) | 69(±3) | 76(±4) | 82(±4) | 80(±4) |
| Formula 73 | — | 19(±3) | 29(±3) | 40(±3) | 55(±3) | 69(±2) | 82(±4) | 80(±4) |
| Cisplatin | — | 36(±3) | 53(±3) | 64(±3) | 73(±3) | 84(±4) | 92(±2) | 88(±3) |
| Formula 74 | — | 15(±3) | 24(±4) | 36(±4) | 45(±2) | 64(±6) | 92(±2) | 88(±3) |
| Cisplatin | — | 36(±3) | 53(±3) | 64(±3) | 73(±3) | 84(±4) | 92(±2) | 88(±3) |
| Formula 75 | — | 16(±2) | 27(±3) | 38(±3) | 46(±4) | 66(±4) | 92(±2) | 88(±3) |
| Cisplatin | — | 32(±4) | 47(±3) | 59(±3) | 68(±3) | 75(±5) | 85(±3) | 80(±4) |
| Formula 76 | — | 23(±3) | 31(±3) | 44(±4) | 58(±4) | 69(±3) | 85(±3) | 80(±4) |
| Cisplatin | — | 32(±4) | 47(±3) | 59(±3) | 68(±3) | 75(±5) | 85(±3) | 80(±4) |
| Formula 77 | — | 21(±3) | 29(±6) | 41(±3) | 55(±3) | 64(±3) | 85(±3) | 80(±4) |
| Cisplatin | — | 32(±4) | 47(±3) | 59(±3) | 68(±3) | 75(±5) | 85(±3) | 80(±4) |
| Formula 78 | — | 24(±4) | 33(±3) | 43(±3) | 55(±3) | 65(±4) | 85(±3) | 80(±4) |
| Cisplatin | — | 32(±4) | 47(±3) | 59(±3) | 68(±3) | 75(±5) | 85(±3) | 80(±4) |
| Formula 79 | — | 24(±4) | 33(±3) | 43(±3) | 55(±3) | 65(±4) | 85(±3) | 80(±4) |
| Cisplatin | — | 31(±3) | 41(±3) | 51(±3) | 61(±3) | 73(±3) | 85(±3) | 80(±3) |
| Formula 80 | — | 14(±3) | 22(±4) | 30(±2) | 45(±3) | 59(±3) | 85(±3) | 80(±3) |
| Cisplatin | — | 32(±3) | 55(±3) | 66(±6) | 78(±3) | 89(±3) | 103(±3) | 100(±3) |
| Formula 81 | — | 21(±3) | 30(±4) | 46(±4) | 57(±5) | 75(±4) | 103(±3) | 100(±3) |

The above results indicate that compounds of Formulae 1, 2, 7, 37, 40, 41, 43, 46, 47, 52 and 67-81 are more effective in inhibiting spheres of PC3 compared to cisplatin.

FIG. 2, FIG. 4, FIG. 6, FIG. 8, FIG. 10, FIG. 12, FIG. 14, FIG. 16, FIG. 18, FIG. 20, FIG. 22, FIG. 24, FIG. 26, FIG. 28, FIG. 30, FIG. 32, FIG. 34, FIG. 36, FIG. 38, FIG. 40, FIG. 42, FIG. 44, FIG. 46, FIG. 48, and FIG. 50 refer to compounds of Formulae 1, 2, 7, 37, 40, 41, 43, 46, 47, 52 and 67-81 respectively.

FIG. 2, FIG. 4, FIG. 6, FIG. 8, FIG. 10, FIG. 12, FIG. 14, FIG. 16, FIG. 18, FIG. 20, FIG. 22, FIG. 24, FIG. 26, FIG. 28, FIG. 30, FIG. 32, FIG. 34, FIG. 36, FIG. 38, FIG. 40, FIG. 42, FIG. 44, FIG. 46, FIG. 48, and FIG. 50 illustrate the percentage viability of spheres obtained from conversion of the number of spheres formed and compared with growth control with DMSO (GCD), wherein GCD is considered as 100% viability. The sphere count results for respective drug concentration indicated in Table 8 have been converted to percentage viability of spheres for graphical representation. The figures and Table 8 indicate that there is a decrease in percentage viability of spheres of PC3 in the presence of compounds of Formulae, 2, 7, 37, 40, 41, 43, 46, 47, 52 and 67-81 in comparison to cisplatin.

TABLE 8

| % Viability of spheres (PC3) | | | | | | | |
|---|---|---|---|---|---|---|---|
| Drug Conc. (in uM) | Untreated (GCD) | 250 | 25 | 2.5 | 0.25 | 0.025 | 0.0025 |
| Cisplatin | 100(±4) | 43(±3) | 56(±3) | 69(±3) | 85(±3) | 94(±3) | — |
| Formula 1 | 100(±4) | 16(±3) | 30(±3) | 45(±3) | 62(±3) | 80(±3) | — |
| Cisplatin | 100(±4) | 43(±3) | 56(±3) | 69(±3) | 85(±3) | 94(±3) | — |
| Formula 2 | 100(±4) | 10(±2) | 21(±3) | 39(±4) | 65(±3) | 77(±4) | — |
| Cisplatin | 100(±4) | 41(±3) | 62(±4) | 73(±3) | 86(±3) | 95(±4) | — |
| Formula 7 | 100(±4) | 11(±2) | 21(±3) | 35(±2) | 50(±3) | 71(±3) | — |
| Cisplatin | 100(±3) | 32(±3) | 55(±3) | 66(±6) | 78(±3) | 89(±3) | — |
| Formula 37 | 100(±3) | 20(±4) | 37(±4) | 56(±4) | 69(±3) | 89(±3) | — |

TABLE 8-continued

| % Viability of spheres (PC3) | | | | | | | |
|---|---|---|---|---|---|---|---|
| Drug Conc. (in uM) | Untreated (GCD) | 250 | 25 | 2.5 | 0.25 | 0.025 | 0.0025 |
| Cisplatin | 100(±3) | — | 31(±3) | 51(±5) | 74(±5) | 84(±4) | 91(±3) |
| Formula 40 | 100(±3) | — | 17(±3) | 34(±3) | 47(±3) | 65(±3) | 80(±5) |
| Cisplatin | 100(±3) | — | 31(±3) | 51(±5) | 74(±5) | 84(±4) | 91(±3) |
| Formula 41 | 100(±3) | — | 27(±4) | 46(±4) | 54(±5) | 72(±3) | 85(±4) |
| Cisplatin | 100(±3) | — | 32(±3) | 55(±3) | 66(±6) | 78(±3) | 89(±3) |
| Formula 43 | 100(±3) | — | 21(±3) | 30(±4) | 46(±4) | 57(±5) | 75(±4) |
| Cisplatin | 100(±3) | — | 38(±3) | 51(±3) | 63(±3) | 76(±3) | 91(±3) |
| Formula 46 | 100(±3) | — | 22(±3) | 36(±3) | 51(±3) | 67(±4) | 82(±3) |
| Cisplatin | 100(±3) | — | 41(±3) | 61(±3) | 76(±4) | 88(±3) | 95(±3) |
| Formula 47 | 100(±3) | — | 18(±3) | 28(±3) | 43(±3) | 57(±4) | 77(±4) |
| Cisplatin | 100(±4) | — | 43(±3) | 56(±3) | 69(±3) | 85(±3) | 94(±3) |
| Formula 52 | 100(±4) | — | 30(±3) | 49(±4) | 62(±3) | 77(±4) | 87(±3) |
| Cisplatin | 100(±1) | — | 39(±2) | 50(±4) | 66(±5) | 79(±6) | 85(±4) |
| Formula 67 | 100(±1) | — | 36(±3) | 44(±2) | 51(±3) | 64(±3) | 70(±5) |
| Cisplatin | 100(±1) | — | 39(±2) | 50(±4) | 66(±5) | 79(±6) | 85(±4) |
| Formula 68 | 100(±1) | — | 24(±2) | 31(±2) | 41(±3) | 55(±3) | 62(±4) |
| Cisplatin | 100(±2) | — | 33(±2) | 62(±3) | 76(±3) | 88(±4) | 98(±2) |
| Formula 69 | 100(±2) | — | 21(±3) | 35(±2) | 49(±2) | 65(±3) | 93(±3) |
| Cisplatin | 100(±2) | — | 33(±2) | 62(±3) | 76(±3) | 88(±4) | 98(±2) |
| Formula 70 | 100(±2) | — | 31(±3) | 41(±4) | 50(±3) | 67(±2) | 95(±2) |
| Cisplatin | 100(±2) | — | 33(±2) | 62(±3) | 76(±3) | 88(±4) | 98(±2) |
| Formula 71 | 100(±2) | — | 20(±3) | 37(±2) | 52(±3) | 65(±3) | 95(±4) |
| Cisplatin | 100(±4) | — | 41(±3) | 62(±4) | 73(±3) | 86(±3) | 95(±4) |
| Formula 72 | 100(±4) | — | 16(±3) | 36(±2) | 46(±3) | 63(±3) | 81(±3) |
| Cisplatin | 100(±4) | — | 41(±3) | 62(±4) | 73(±3) | 86(±3) | 95(±4) |
| Formula 73 | 100(±4) | — | 23(±3) | 36(±3) | 50(±3) | 68(±3) | 86(±2) |
| Cisplatin | 100(±3) | — | 40(±3) | 60(±3) | 72(±3) | 82(±3) | 95(±4) |
| Formula 74 | 100(±3) | — | 17(±3) | 27(±4) | 41(±4) | 56(±2) | 73(±6) |
| Cisplatin | 100(±3) | — | 40(±3) | 60(±3) | 72(±3) | 82(±3) | 95(±4) |
| Formula 75 | 100(±3) | — | 20(±2) | 33(±3) | 47(±3) | 57(±4) | 82(±4) |
| Cisplatin | 100(±4) | — | 40(±4) | 58(±3) | 73(±3) | 85(±3) | 93(±5) |
| Formula 76 | 100(±4) | — | 28(±3) | 38(±3) | 55(±4) | 72(±4) | 86(±3) |
| Cisplatin | 100(±4) | — | 40(±4) | 58(±3) | 73(±3) | 85(±3) | 93(±5) |
| Formula 77 | 100(±4) | — | 26(±3) | 36(±6) | 51(±3) | 68(±3) | 80(±3) |
| Cisplatin | 100(±4) | — | 40(±4) | 58(±3) | 73(±3) | 85(±3) | 93(±5) |
| Formula 78 | 100(±4) | — | 30(±4) | 41(±3) | 53(±3) | 68(±3) | 81(±4) |
| Cisplatin | 100(±3) | — | 38(±3) | 51(±3) | 63(±3) | 76(±3) | 91(±3) |
| Formula 79 | 100(±3) | — | 20(±3) | 30(±3) | 43(±5) | 57(±6) | 78(±3) |
| Cisplatin | 100(±3) | — | 38(±3) | 51(±3) | 63(±3) | 76(±3) | 91(±3) |
| Formula 80 | 100(±3) | — | 17(±3) | 27(±4) | 37(±2) | 56(±3) | 73(±3) |
| Cisplatin | 100(±3) | — | 32(±3) | 55(±3) | 66(±6) | 78(±3) | 89(±3) |
| Formula 81 | 100(±3) | — | 21(±3) | 30(±4) | 46(±4) | 57(±5) | 75(±4) |

4. Activity on Lymphocytes

Lymphocyte Assay

Human lymphocytes were isolated from the peripheral blood. A pure population of lymphocytes was obtained based on differential centrifugation, in which diluted defibrinated blood was layered on a solution of sodium diatrizoate and polysucrose (HiSep LSM 1077) and centrifuged at low speeds for 30 mins.

Procedure: The separation of lymphocytes from fresh defibrinated blood was performed by the procedure described below:

1. Diluted defibrinated fresh blood was overlaid gradually on (HiSeP LSM1077) and centrifuged at low speed for 30 mins.
2. The lymphocyte layer (the buffy coat) was carefully removed in a new collection tube.
3. The buffy coat was given another wash, by the diluent buffer Dulbecco's phosphate buffered saline (D.P.B.S)
4. The supernatant was discarded and the pellet was resuspended in D.P.B.S.
5. The viability of cells was checked by Haemocytometer.
6. Cells with purity and viability of more than 95% were taken for the experiment.
7. Purified lymphocytes were diluted at a concentration of 0.7 million/ml with sterile D.P.B.S and MTT procedure was performed exactly as described earlier.

TABLE 9

| Lymphocyte Results: IC50 in μM | | | |
|---|---|---|---|
| Compounds | BREAST CANCER MDAMB231 (IC50 in μM) | PROSTATE CANCER PC3 (IC50 in μM) | Activity on Lymphocytes (IC50 in μM) |
| Formula 1 | 0.656 | 0.579 | 1.49 |
| Formula 2 | 0.566 | 0.344 | 11.49 |
| Formula 40 | 0.951 | 1.68 | 13.18 |
| Formula 41 | 3.06 | 2.73 | No activity |
| Formula 43 | 1.01 | 0.50 | 10.76 |
| Formula 52 | 3.13 | 4.32 | No activity |
| Formula 67 | 3.09 | 4.11 | 5.15 |
| Formula 68 | 3.18 | 4.73 | 5.58 |
| Formula 69 | 2.75 | 2.12 | 12.1 |
| Formula 70 | 3.02 | 2.23 | 5.41 |
| Formula 71 | 1.35 | 3.55 | 25.23 |
| Formula 72 | 1.01 | 0.743 | 32.96 |
| Formula 73 | 2.18 | 3.05 | No activity |

Figure 53:
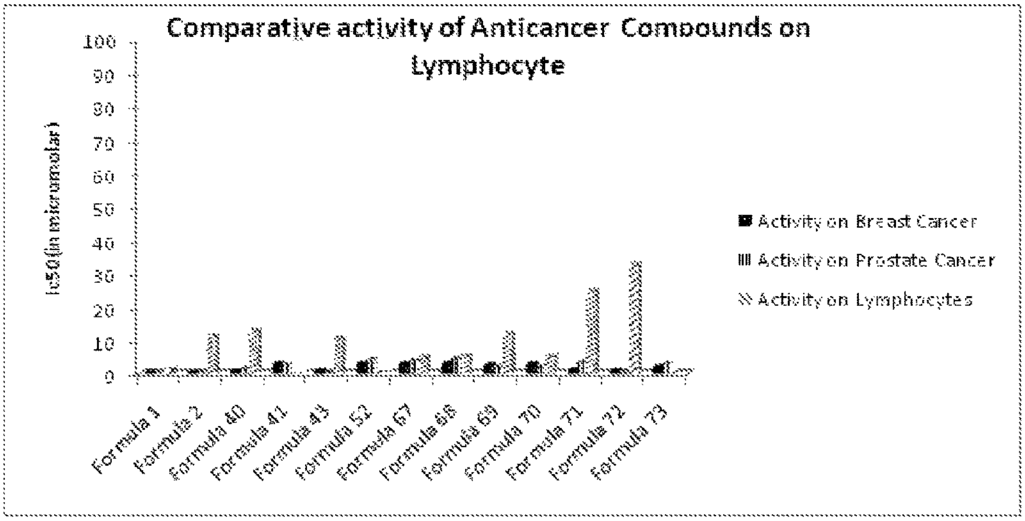
FIG. 53 illustrates the activity of compounds of Formulae 1, 2, 40, 41, 43, 52, 67, 68, 69, 70, 71, 72, 73 on lymphocytes.

Above table and FIG. 53 indicates that the activity of the compounds is higher on cancer cells compared to normal cells indicating the safety of these compounds.

5. Wound Healing Effect

Wound Healing Assay: (WHA)

Wound Healing Assay (WHA) determines the ability of cancer stem cells to heal the wound formed in a confluent monolayer. The assay was used to measure the ability of a test drug to inhibit cancer stem cells wound healing capacity compared to standard chemotherapeutic drug such as Cisplatin.

Procedure: $0.35\times10^6$ cells were plated in each well of 6 Tissue Culture well plates. The plate was incubated for 48 hrs at 37° C., 5% $CO_2$. The cells were observed for their complete confluency and a horizontal scratch was made at the center of each well using sterile 100 μl tip, after giving two washes with D.P.B.S. The width of the scratch was measured at 0 hrs, immediately after the scratch was made. IC10 conc. of the respective compound was added into each well. The plates were incubated at 37° C., 5% CO2 and the width of scratch was measured at various time intervals such as 6, 24 and 48 hours. Average of 3 distances were taken for each time point using IS camera Measure. A plot of average width of scratch in micrometer was plotted against the time interval after treatment. The anti CSC potential was determined by calculating the % inhibition after 48 hrs for each compound compared to Cisplatin.

TABLE 10

Wound Healing Assay (WHA) Results

| Compounds | % inhibition of Wound Healing for Breast Cancer Cell line (MDAMB231) after 48 hrs | % inhibition of Wound Healing for Prostate Cancer Cell line (PC3) after 48 hrs |
|---|---|---|
| Cisplatin | 33.78 | 25.13 |
| Compound 2 | 53.69 | 45.25 |
| Compound 52 | 37.42 | 34.7 |
| Compound 40 | 45.84 | 48.56 |
| Compound43 | 53.3 | 50.47 |

Figure 54:
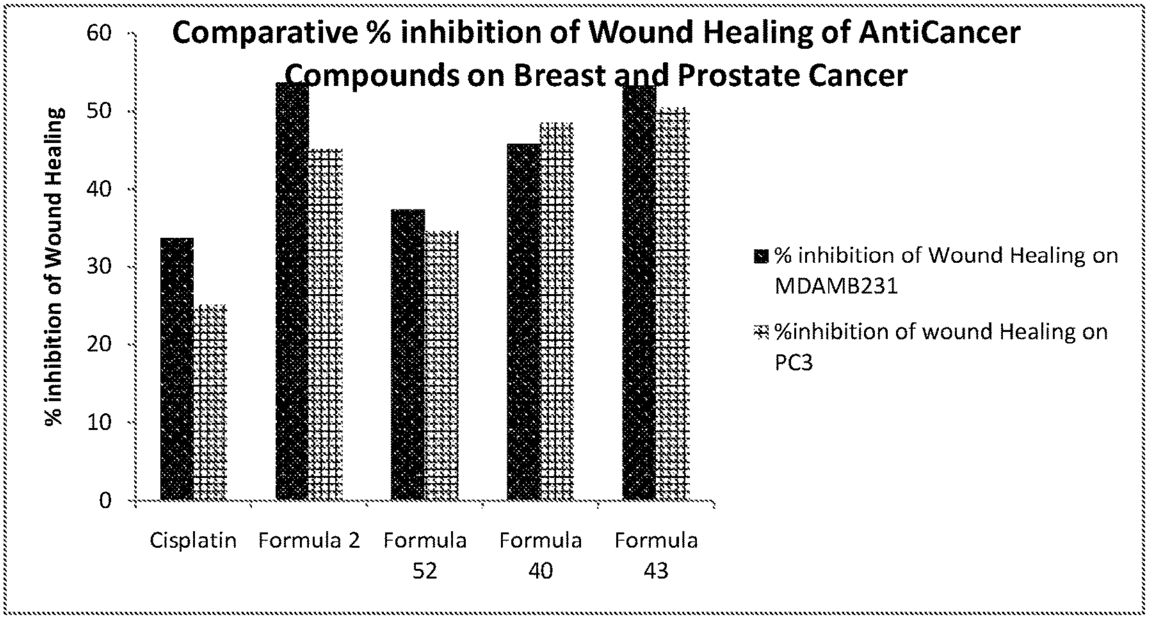
FIG. 54 illustrates wound healing effect of compounds of Formulae 2, 52, 40, 43 and cisplatin on breast and prostate cancer.

Above table and FIG. 54 indicate that the anticancer compounds inhibit the cancer cells wound healing thereby preventing the spread of cancer compared to standard therapeutic drug Cisplatin.

6. Inhibition Effect of the Compounds on a Cancer Marker, Aldehyde Dehydrogenase (ALDH)

Aldehyde Dehydrogenase (ALDH)Assay:

Aldehyde dehydrogenases (ALDH) are a family of enzymes that catalyze the metabolism of exogenous and endogenous aldehydes, preventing the accumulation of potentially reactive and toxic aldehydes and their metabolites. In addition to their role in aldehyde metabolism, ALDH enzymes also play critical roles in other cellular processes such as cell proliferation, differentiation, and survival.

ALDH also serves as a marker for certain stem cell populations including hematopoietic stem cells and certain cancer stem cells.

ALDH concentration was determined by using (Kinesis Dx) ELISA kit by following protocol:

1 Standards (50 μl)/sample (40 μl) were added to the respective wells, (except Blank).

2. (10 μl) Antibody-Biotin conjugate was then added in each sample well (except Blank).

3. (50 μl) of Horse Radish Peroxidase (HRP) Conjugate was then added to each well (except Blank).

4. The plates were incubated for one hour at 37° C. in the incubator.

5. Wash (4 times with wash buffer) and blot residual buffer by firmly tapping the plate on the absorbent paper. Wipe off any liquid from the bottom of the microtiter wells as any residue can interfere in the reading step.

6. Add TMB substrate A (50 μl) and then TMB substrate B (50 μl) to each well including Blank as well.

7. Incubate for 10 mins at 37° C. in dark.

8. Add (50 μl) stop solution. Wells should turn from blue to yellow.

9. Read absorbance at 450 nm.

10 A X-Y graph of concentration vs optical density was plotted. ALDH concentration was calculated by substituting optical density values in the regression analysis equation.

TABLE 11

Aldehyde Dehydrogenase (ALDH) Results

| Compounds | % inhibition of ALDH on Breast Cancer Cell line (MDAMB231) after 48 hrs |
|---|---|
| Cisplatin | 26.45 |
| Compound 2 | 76.09 |
| Compound 52 | 74.69 |
| Compound 40 | 62.73 |

Figure 55:
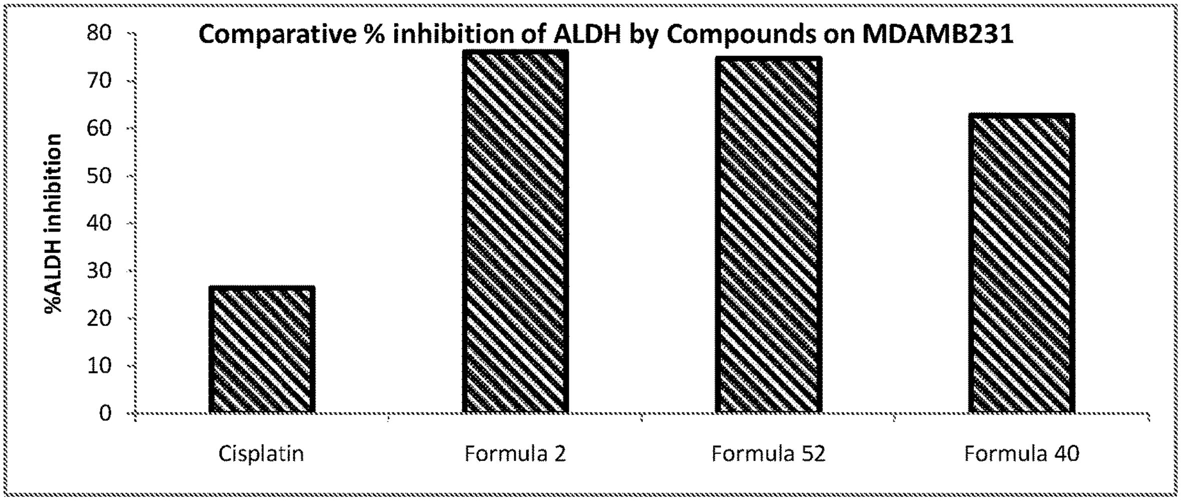
FIG. 55 illustrates the inhibition effect of compounds of Formulae 2, 52, 40 and cisplatin on Aldehyde dehydrogenase (ALDH), a Cancer Stem Cell (CSC) marker.

Above table and FIG. 55 indicate that the compounds inhibit Aldehyde dehydrogenase (ALDH)—a Cancer Stem Cell (CSC) marker compared to standard therapeutic drug, Cisplatin.

The invention claimed is:

1. A compound of Formula I:

Formula I

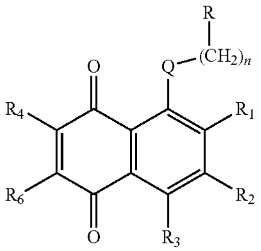

wherein, n is 1-6;

Q is O or $-Q-(CH_2)_n-R$ is absent;

$R_1$, $R_2$, and $R_3$ are each —H;

$R_4$ is selected from —H,

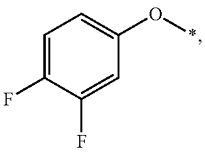,
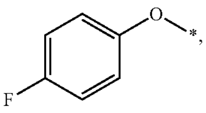,
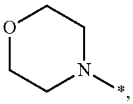,

-continued
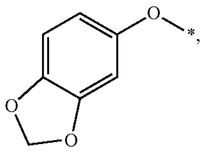
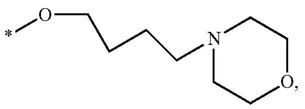 or
R is selected from —COOH,
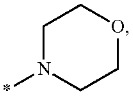
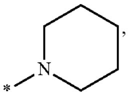
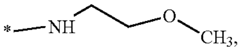
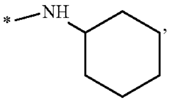
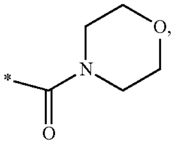
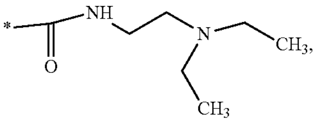 or
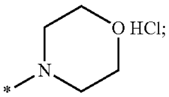
$R_6$ is selected from —H,
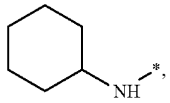
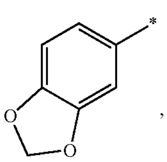
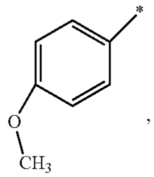
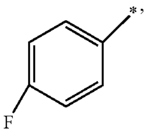
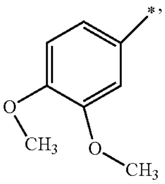
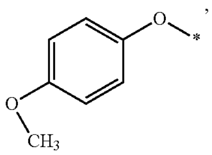
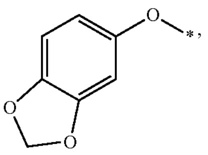
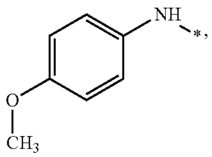
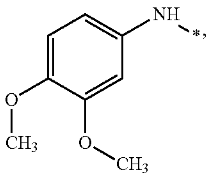
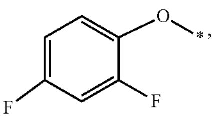
-continued
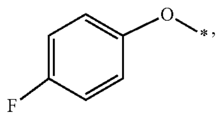 or
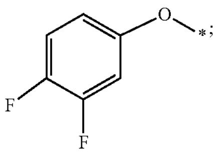
represents point of attachment,
when R=—COOH, n=3 to 6 and $R_6$ is selected from
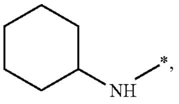
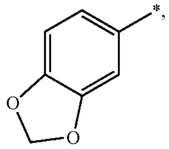
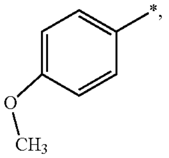
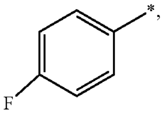
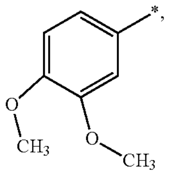
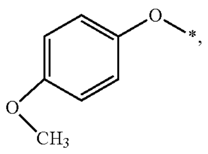
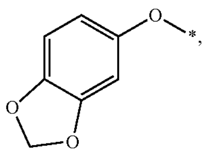
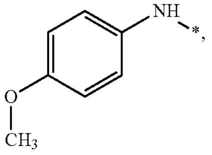
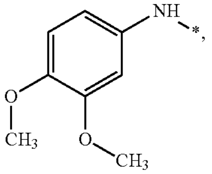
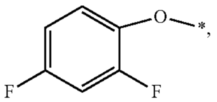
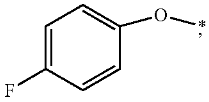 or
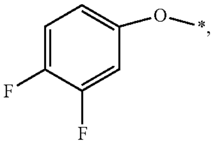
wherein the compound is selected from any one of the following compounds:
Formula 1
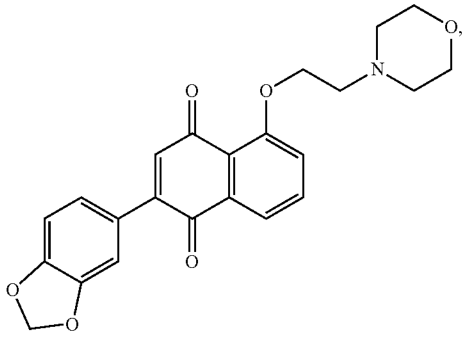

-continued
Formula 2
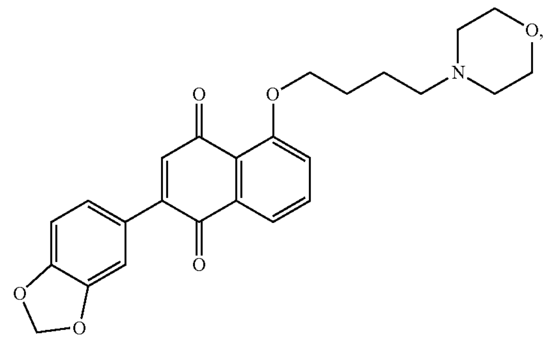
Formula 4
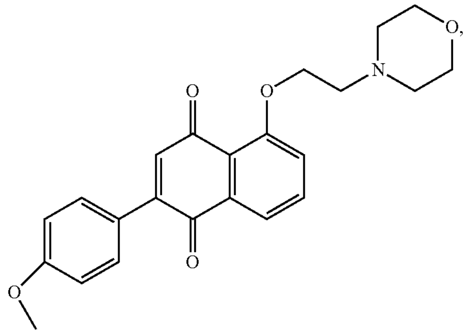
Formula 5
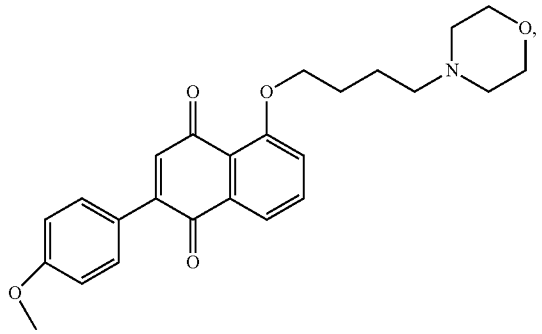
Formula 6
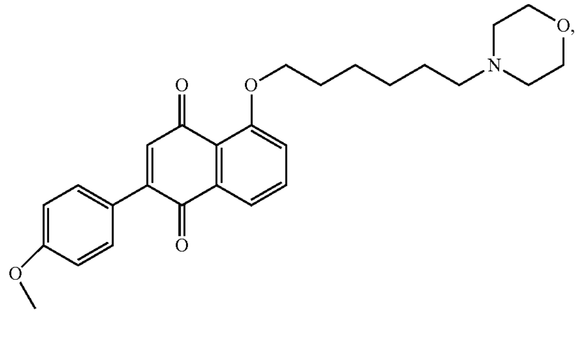
-continued
Formula 7
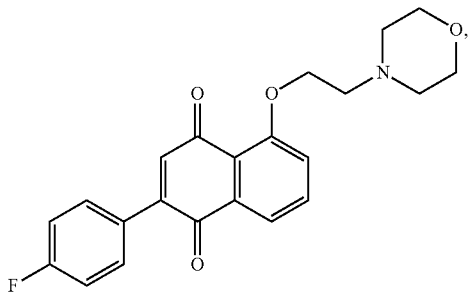
Formula 8
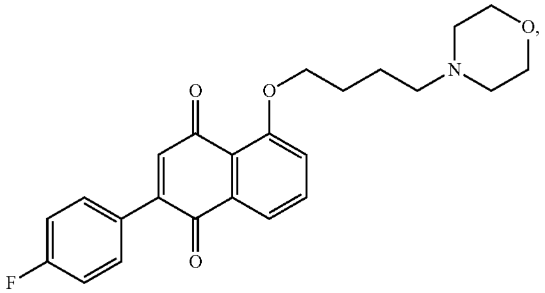
Formula 9
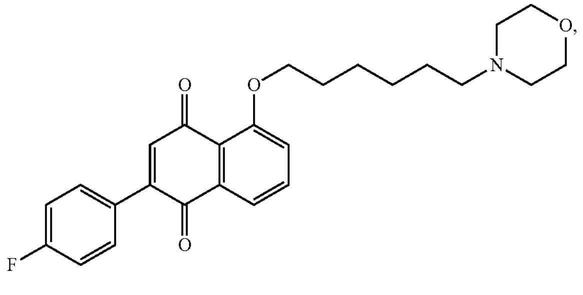
Formula 10
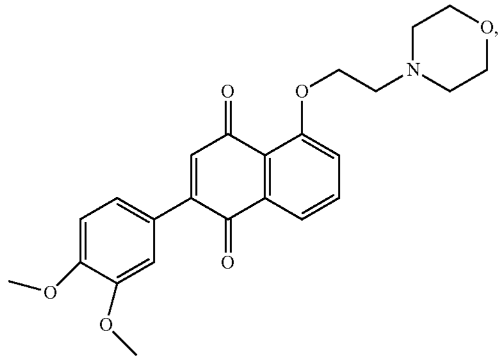

-continued
Formula 11
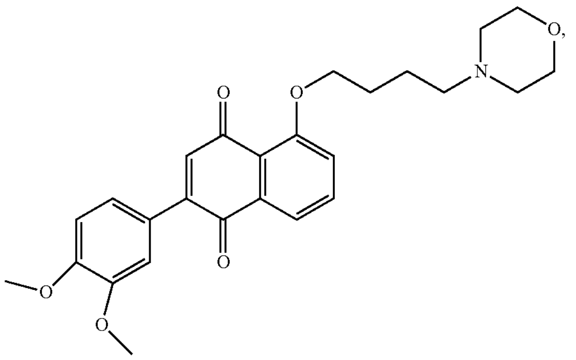
Formula 12
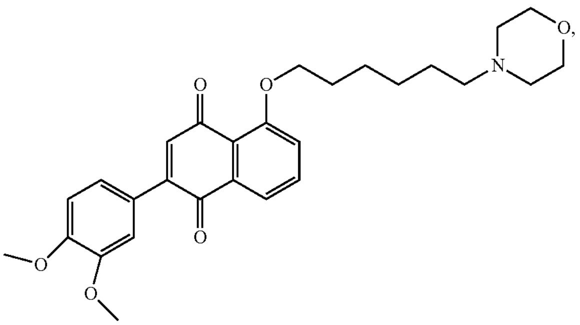
Formula 17
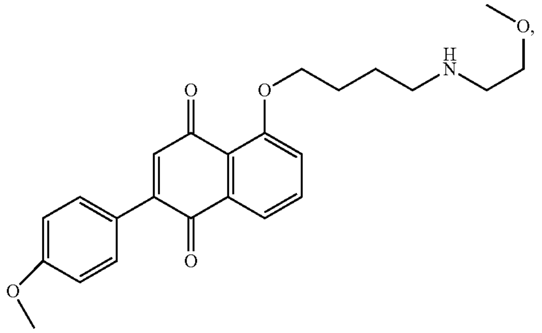
Formula 20
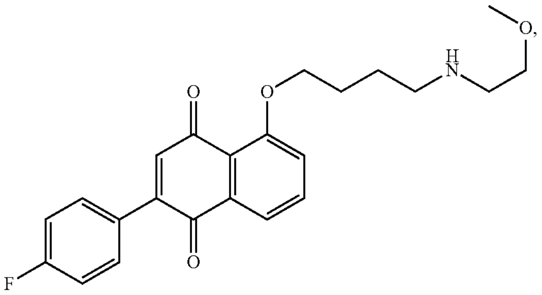
-continued
Formula 23
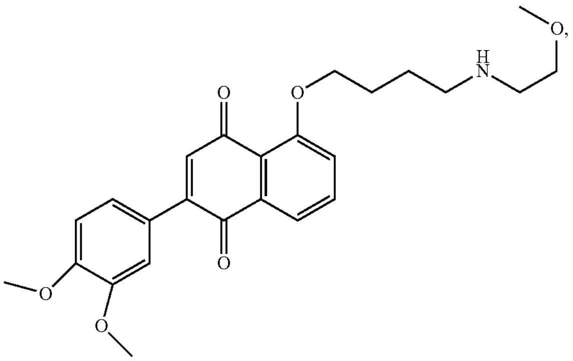
Formula 32
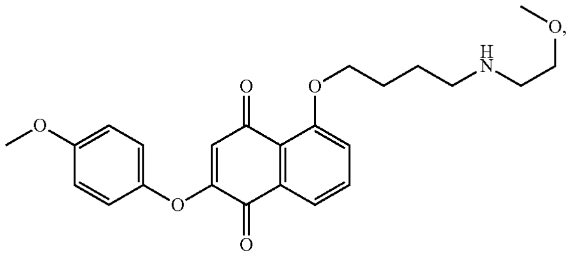
Formula 33
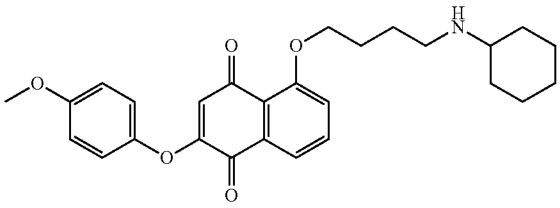
,
Formula 35
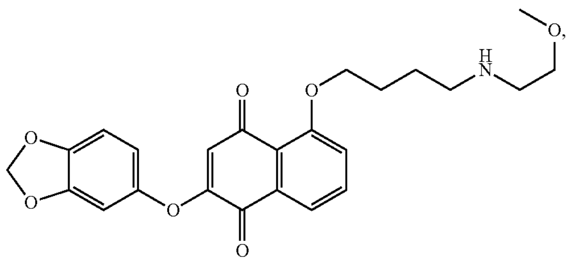
Formula 36
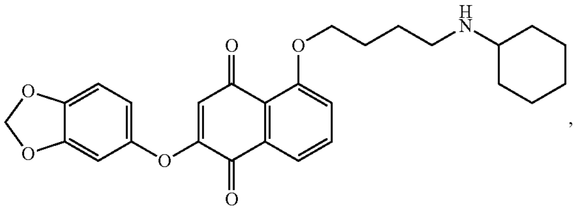
, -continued
Formula 37
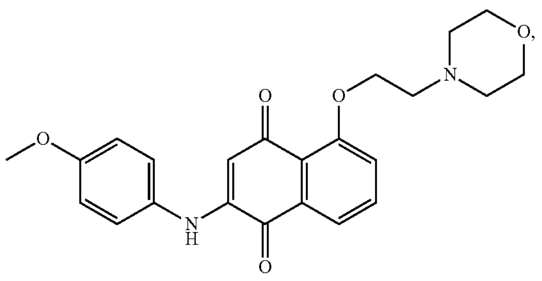
Formula 40
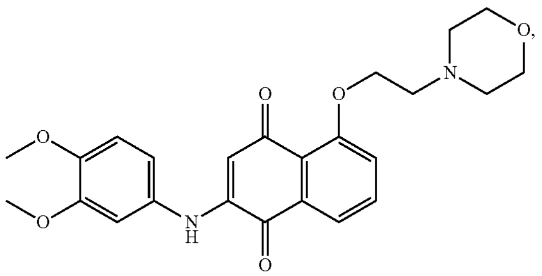
Formula 41
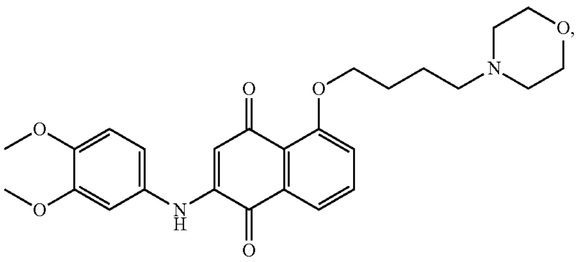
Formula 43
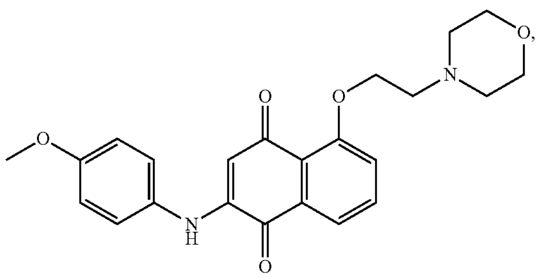
Formula 44
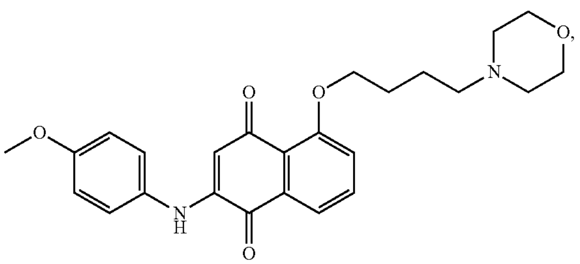
-continued
Formula 46
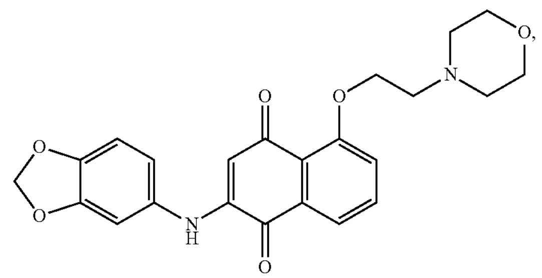
Formula 47
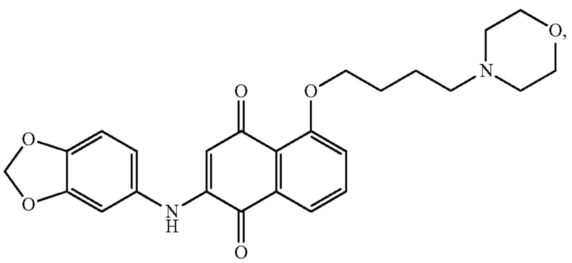
Formula 52
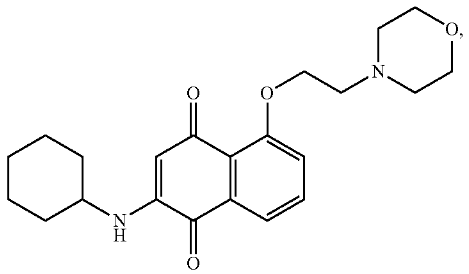
Formula 67
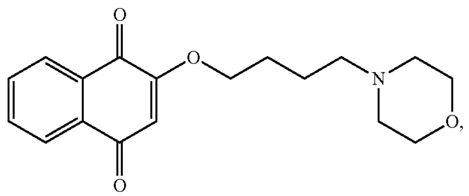
Formula 68
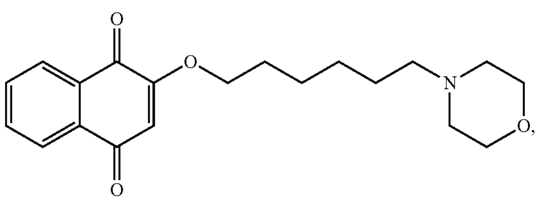

-continued
Formula 69
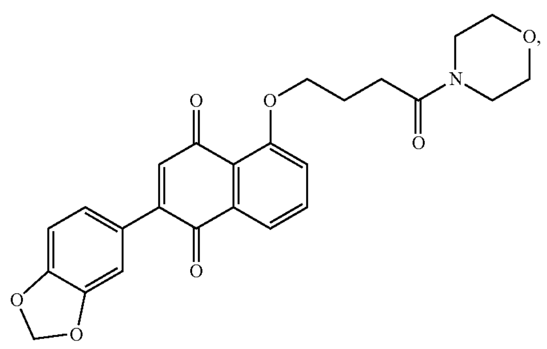
Formula 70
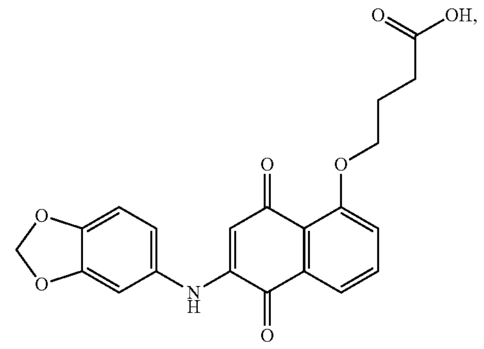
Formula 71
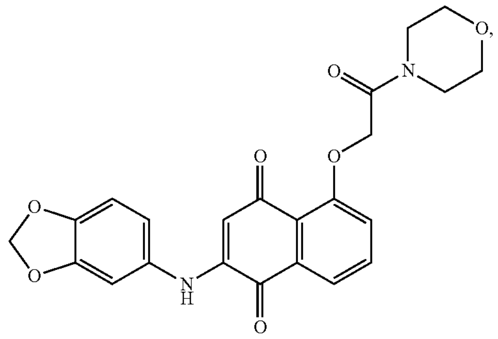
Formula 72
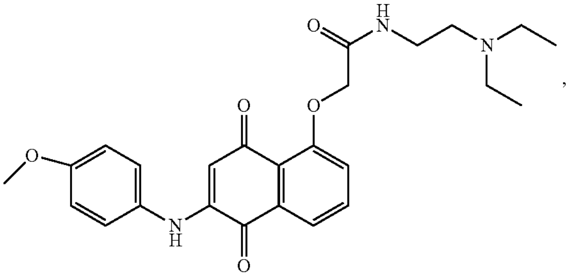
-continued
Formula 73
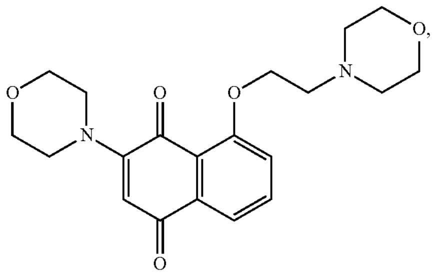
Formula 74
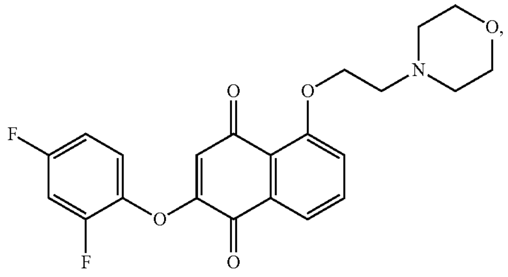
Formula 75
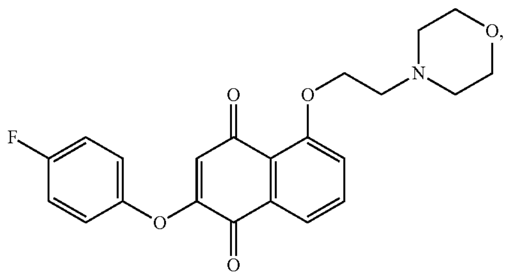
Formula 76
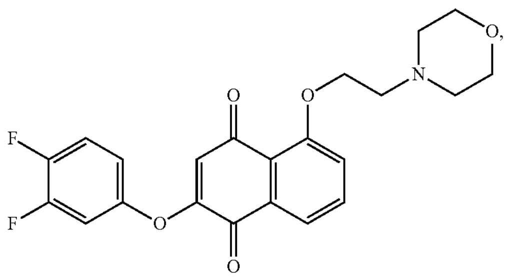
Formula 77
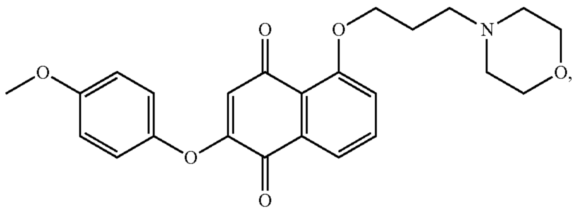

-continued
Formula 78
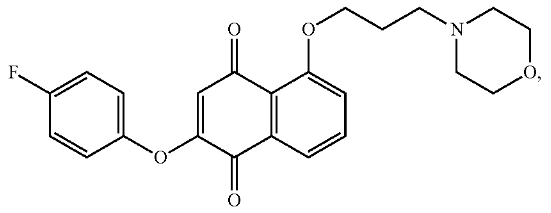
Formula 79
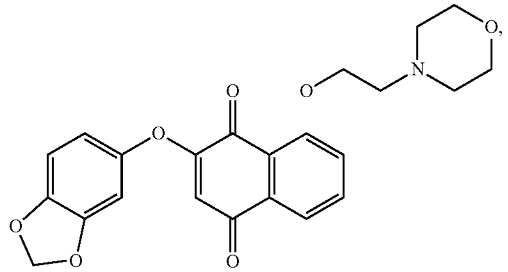
Formula 80
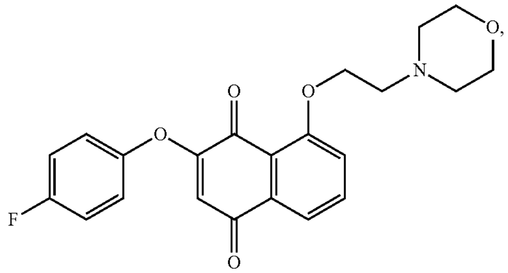
Formula 81
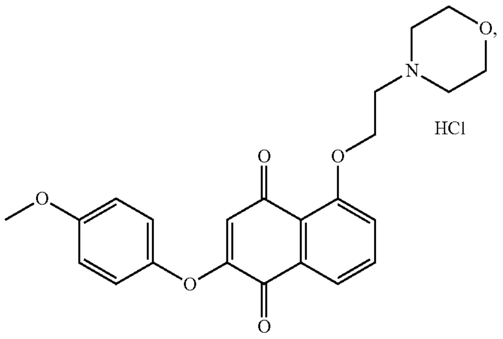
Formula 82
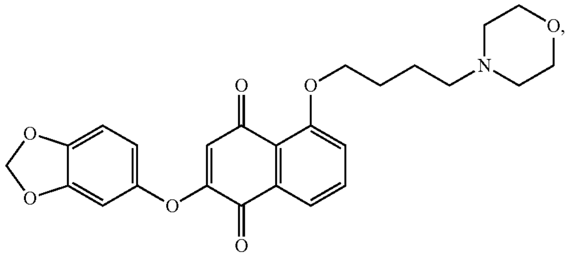
-continued
Formula 83
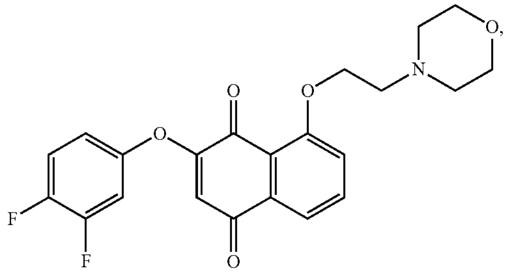
Formula 84
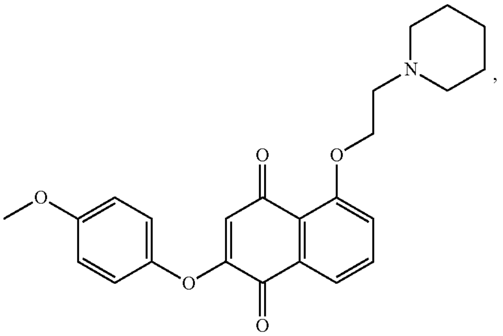
Formula 85
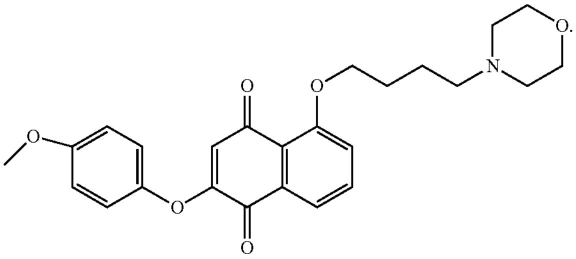
2. The compound as claimed in claim 1, wherein $R_6$ is selected from,
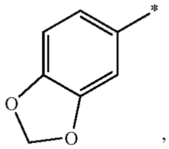
,
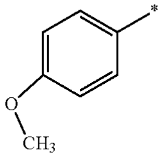
,
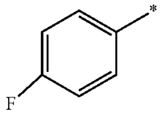
, or
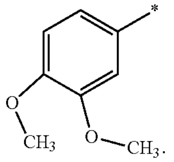
3. The compound as claimed in claim 1, wherein $R_6$ is selected from

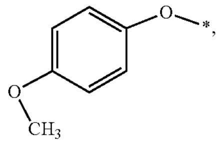, 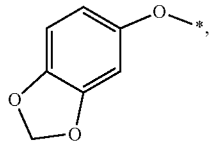,

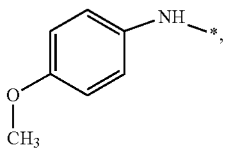, 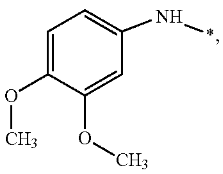,

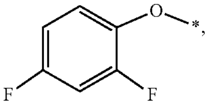, 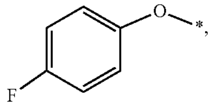, or

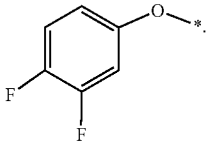.

4. The compound as claimed in claim 1, wherein $R_6$ is

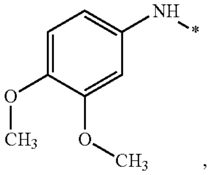, 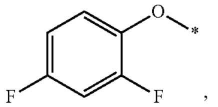, 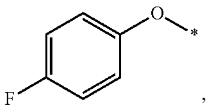, or 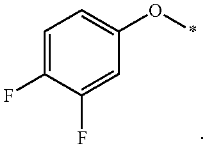.

5. A pharmaceutical composition for use in treatment of unregulated cell growth or cancer in combination with at least one standard therapy for treating cancer comprising the compound according to claim 1.

6. A method of treating or inhibiting uncontrolled cell growth or cancer, the method comprising administering an effective amount of the compound as claimed in claim 1.

7. The method as claimed in claim 6, wherein the cancer is breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach cancer.

8. A pharmaceutical composition comprising a compound of Formula I:

Formula I

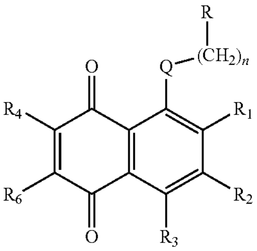

wherein, n is 1-6;

Q is O or $-Q-(CH_2)_n-R$ is absent;

$R_1$, $R_2$, and $R_3$ are each —H;

$R_4$ is selected from —H,

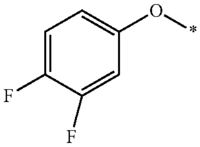, 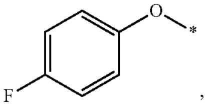,

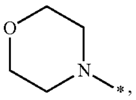, 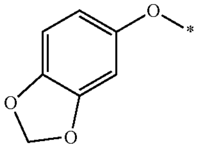,

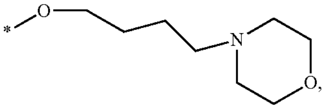, or

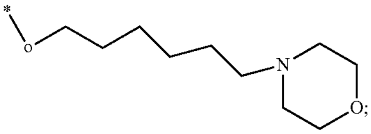;

R is selected from —COOH,

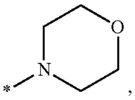, 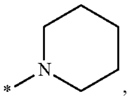,

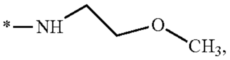, 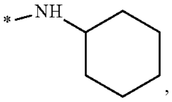,

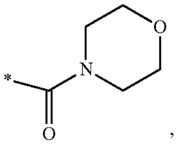, 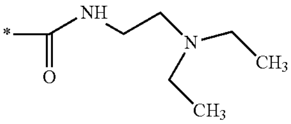, or

-continued

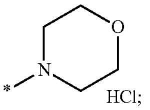

$R_6$ is selected from —H,

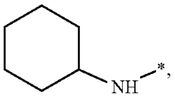
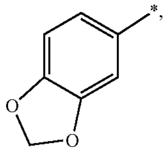
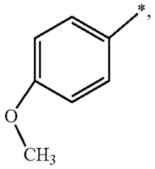
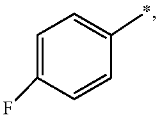
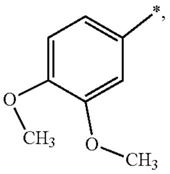
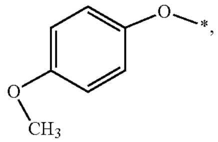
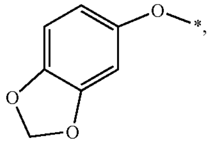
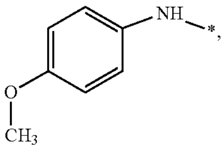
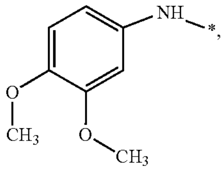
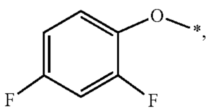
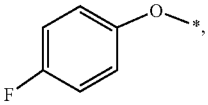 or 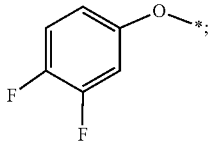

* represents point of attachment, when R=—COOH, n=3 to 6 and $R_6$ is selected from

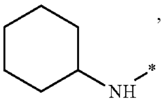
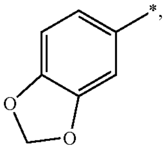
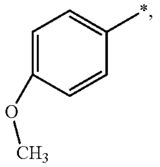
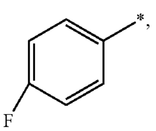
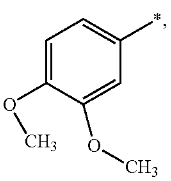
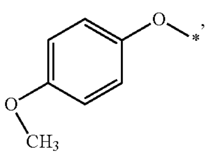

-continued

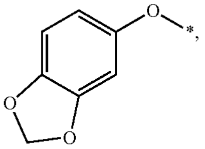
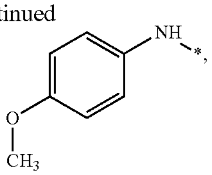
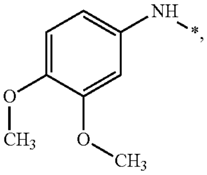
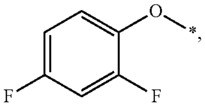
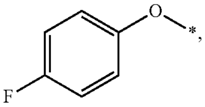 or 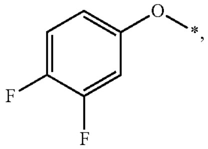

and at least one pharmaceutically acceptable excipient in the presence or absence of one or more active agent.

9. A method of treating or inhibiting uncontrolled cell growth or cancer comprising administering an effective amount of the pharmaceutical composition as claimed in claim 8.

10. A pharmaceutical composition for use in treatment of unregulated cell growth or cancer comprising a compound of Formula I:

Formula I

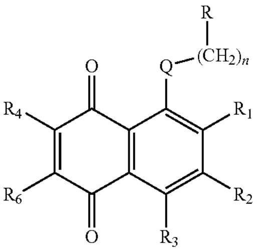

wherein, n is 1-6;

Q is O or $-Q-(CH_2)_n-R$ is absent;

$R_1$, $R_2$, and $R_3$ are each —H;

$R_4$ is selected from —H,

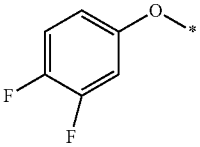 , 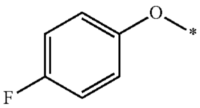 ,

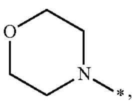
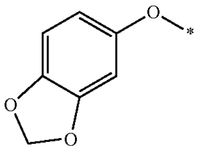 ,

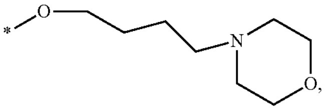 or

-continued
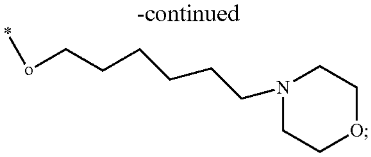
R is selected from —COOH,
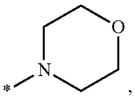,
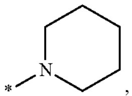,
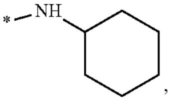,
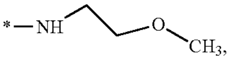
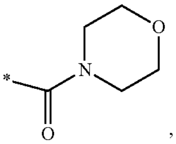,
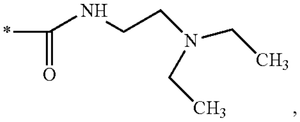, or
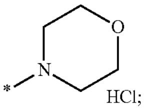
$R_6$ is selected from —H,
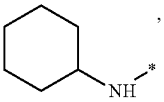,
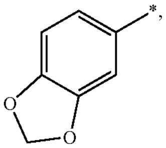
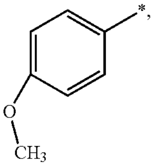
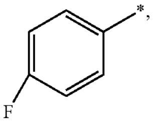
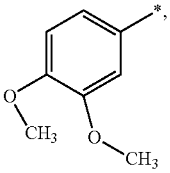
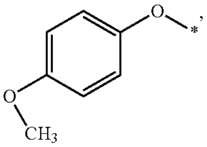
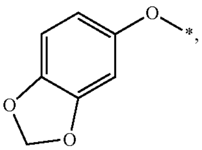
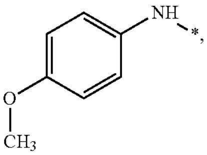
-continued
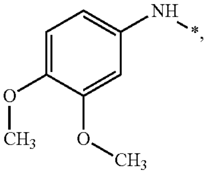
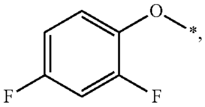
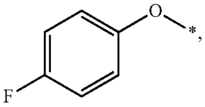, or
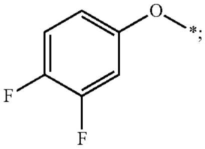
* represents point of attachment, when R=—COOH, n=3 to 6 and $R_6$ is selected from
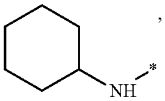,
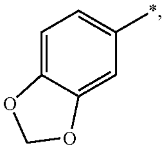
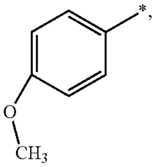
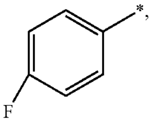
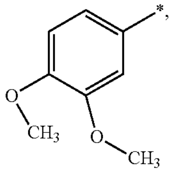
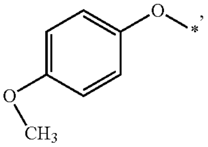
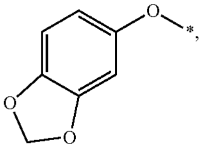
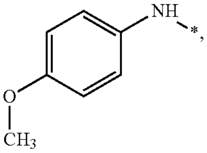
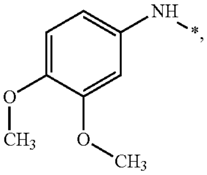
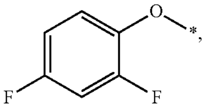
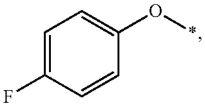, or
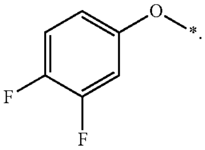
* * * * *